United States Patent
Li et al.

(10) Patent No.: US 12,129,284 B2
(45) Date of Patent: Oct. 29, 2024

(54) COMPOSITIONS AND METHODS FOR THE TREATMENT OF CANCER CHARACTERIZED WITH PCSK9 EXPRESSION

(71) Applicant: DUKE UNIVERSITY, Durham, NC (US)

(72) Inventors: Chuan-Yuan Li, Durham, NC (US); Xinjian Liu, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 303 days.

(21) Appl. No.: 17/252,409

(22) PCT Filed: Jun. 25, 2019

(86) PCT No.: PCT/US2019/038882
§ 371 (c)(1),
(2) Date: Dec. 15, 2020

(87) PCT Pub. No.: WO2020/005869
PCT Pub. Date: Jan. 2, 2020

(65) Prior Publication Data
US 2021/0269493 A1 Sep. 2, 2021

Related U.S. Application Data

(60) Provisional application No. 62/689,288, filed on Jun. 25, 2018, provisional application No. 62/771,293, filed on Nov. 26, 2018.

(51) Int. Cl.
| | |
|---|---|
| *A61K 38/00* | (2006.01) |
| *A61P 35/00* | (2006.01) |
| *C07K 14/47* | (2006.01) |
| *C07K 16/28* | (2006.01) |

(52) U.S. Cl.
CPC .......... *C07K 14/4703* (2013.01); *A61P 35/00* (2018.01); *C07K 16/2818* (2013.01); *C07K 16/2827* (2013.01); *A61K 38/00* (2013.01)

(58) Field of Classification Search
CPC ............ C07K 14/4703; C07K 16/2818; C07K 16/2827; A61K 38/00; A61P 35/00
See application file for complete search history.

(56) References Cited

U.S. PATENT DOCUMENTS

| | | |
|---|---|---|
| 9,109,034 B1 | 8/2015 | Clube |
| 2013/0189278 A1 | 7/2013 | Sitlani et al. |
| 2018/0023071 A1 | 1/2018 | Basak |

FOREIGN PATENT DOCUMENTS

| | | |
|---|---|---|
| CN | 1082392633 B | 8/2021 |
| WO | 2008057457 A2 | 5/2008 |
| WO | 2011027257 A2 | 3/2011 |
| WO | 2014150395 A1 | 9/2014 |
| WO | 2017121319 A1 | 7/2017 |
| WO | 2017215590 A1 | 12/2017 |
| WO | 2018087391 A1 | 5/2018 |

OTHER PUBLICATIONS

ISA/US; International Search Report and Written Opinion for International Patent Application No. PCT/US19/38882 dated Jan. 2, 2020, 11 pages.
Wu, George, et al., "Receptor-mediated in vitro gene transformation by a soluble DNA carrier system", The Journal of Biological Chemistry, vol. 262, No. 10, Apr. 1987, 4 pages.
JPO; Office Action for Japanese Patent Application No. 2020-572854 dated Feb. 4, 2022, 5 pages.
EPO; Extended European Search Report for European Patent Application No. 19827046.4 dated Feb. 22, 2022, 13 pages.
Abbas Momtazi-Borojeni, Amir, et al., "Potential anti-tumor effect of a nanoliposomal antiPCSK9 vaccine in mice bearing colorectal cancer", Archives of Medical Science, vol. 15, No. 3, Jan. 1, 2019, 11 pages.
Abbas Momtazi-Borojeni, Amir, et al., "Effects of immunization against PCSK9 in an experimental model of breast cancer", Archives of Medical Science, vol. 15, No. 3, Jan. 1, 2019, 10 pages.
JPO; Office Action for Japanese Patent Application No. 2020-572854 dated Aug. 1, 2022, 5 pages.
WIPO; International Search Report and Written Opinion for International Patent Application No. PCT/US2019/038882 dated Jan. 7, 2021, 7 pages.
Smith, Kelly L., et al., "Controlled Release", Membrane Handbook, Springer Science+Business Media New York, 1992, 21 pages.
Sefton, Michael V., et al., "Implantable Pumps", CRC Critical Reviews in Biomedical Engineering, vol. 14, No. 3, 1987, 40 pages.
Langer, Robert, "New Methods of Drug Delivery", Science: American Association for the Advancement of Science, vol. 249, Issue 4976, Sep. 28, 1980, 8 pages.
Goodson, J. Max, "Medical Applications of Controlled Release: Chapter 6 Dental Applications", vol. 2, 1984, 13 pages.
Lopez-Berestein, G., et al., Liposomes in the Therapy of Infectious Diseases and Cancer, Elsevier Science Publishers B.V., 1989, 1 page.
China National Intellectual Property Administration; Office Action from Corresponding CN Patent Application No. 201980055115.1, mailed Jun. 18, 2023, 12 pages.

*Primary Examiner* — Jeanette M Lieb
(74) *Attorney, Agent, or Firm* — NK Patent Law

(57) ABSTRACT

A method for treating cancer in an individual comprises administering to the individual a therapeutically effective amount of a PCSK9 inhibitor. The method may further comprise administering to the individual at least one immune checkpoint inhibitor.

21 Claims, 56 Drawing Sheets
Specification includes a Sequence Listing.

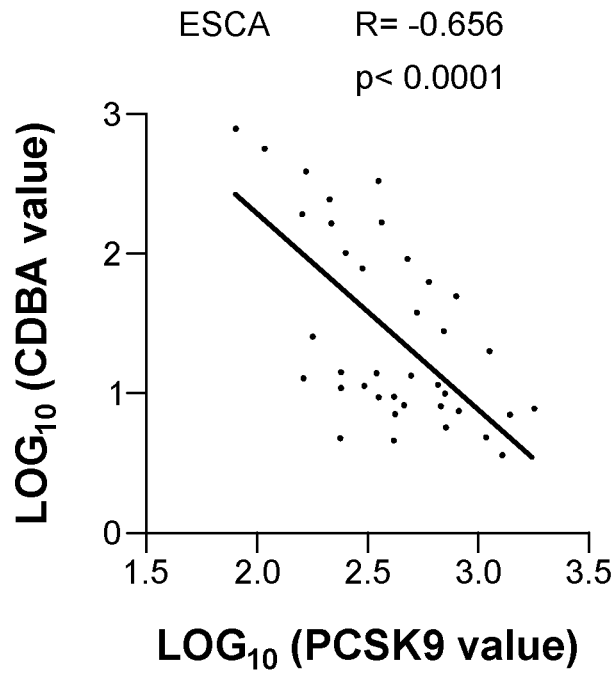
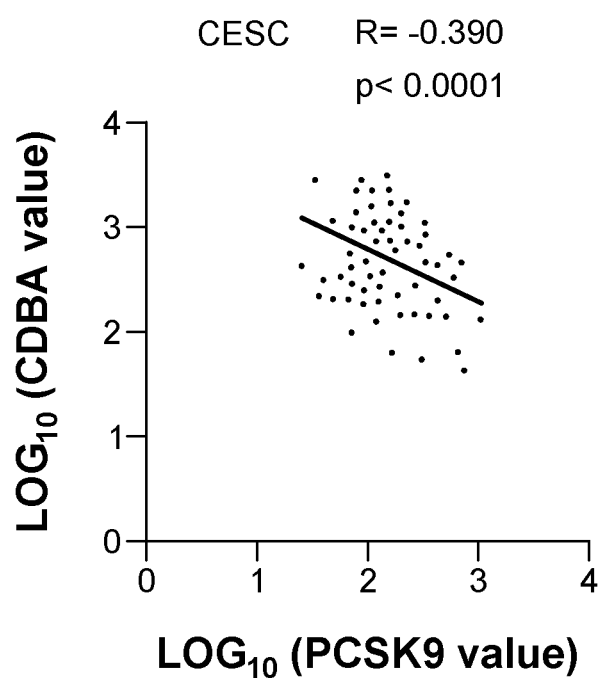
FIG. 8O.1

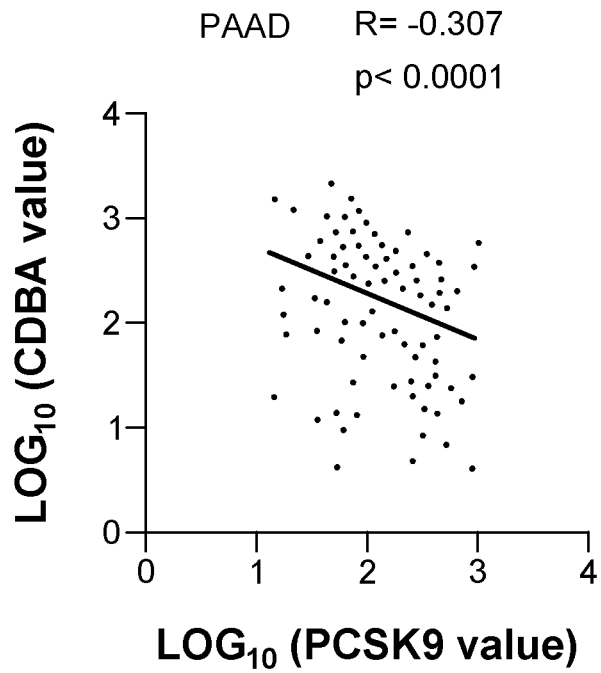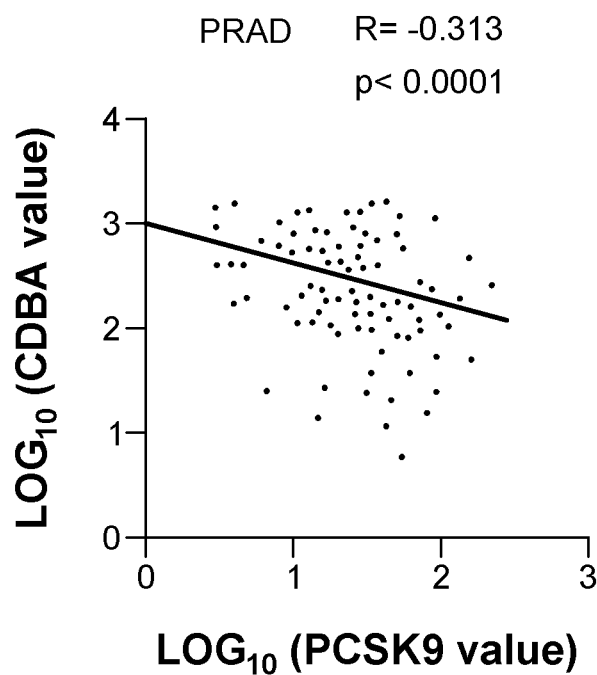
FIG. 8O.II

COMPOSITIONS AND METHODS FOR THE TREATMENT OF CANCER CHARACTERIZED WITH PCSK9 EXPRESSION

RELATED APPLICATIONS

This application is a U.S. National Stage Application of International Patent Application No. PCT/US19/38882, filed on Jun. 25, 2019, which claims priority to U.S. Provisional Patent Application No. 62/689,288 filed on Jun. 25, 2018, and U.S. Provisional Patent Application No. 62/771,293 filed on Nov. 26, 2018, which are incorporated by reference herein in their entireties.

TECHNICAL FIELD

The presently disclosed subject matter is directed to compositions and methods of treating cancer through inhibition of PCSK9 expression.

BACKGROUND

The advent of the immune checkpoint inhibitor therapy is one of the major advances in cancer therapy recently. Inhibition of the immune checkpoints have been demonstrated to be effective in many types of cancer including melanoma, lung cancer, bladder cancer, etc. However, despite their enormous successes, immune checkpoint inhibitors are only effective in 10-30% of cancer patients. Nonetheless, the durable success observed in the subset of patients who respond to immune checkpoint therapy is unprecedented and demonstrated the enormous potential of cancer immunotherapy. Therefore, there is clearly an urgent need to find additional molecular targets that may complement or synergize with existing immune checkpoint inhibitors.

SUMMARY

The Summary is provided to introduce a selection of concepts that are further described below in the Detailed Description. This Summary is not intended to identify key or essential features of the claimed subject matter, nor is it intended to be used as an aid in limiting the scope of the claimed subject matter.

The present disclosure is based, in part, on the discovery by the inventors that PCSK (proprotein convertase subtilisin/kexin type 9 precursor) is a novel target for cancer treatment. PCSK9 is a secreted protein that is known to play a key role in regulating the LDL-R (low density lipoprotein receptor) levels in hepatocytes and other cell types. PCSK9 negatively regulates LDL-R by binding to it and promoting its degradation inside host cells. Previously it was found that mutations within the PCSK9 genes, depending on whether they enhance or attenuate the LDL-R degradation functions of PCSK9, can lead to dramatically increased or decreased LDL blood concentrations. PCSK9 depletion also causes a significant increase in MHC-I expression on the surface of tumor cells, which promotes robust intratumoral infiltration of cytotoxic T-cells.

In one embodiment of the present invention, a method for treating cancer in an individual may include administering to the individual a therapeutically effective amount of a PCSK9 inhibitor.

In another embodiment of the present invention, the PCSK9 inhibitor may be an antagonistic antibody against PCSK9. In preferred embodiments, the antagonistic antibody may be Repatha® (also known as Amgen 145 and evolocumab), Praluent® (also known as REGN 727 [Regeneron] and SAR236553 [Sanofi]), LY3015014 (also known as Frovocimab [Lilly]), RN316 (also known as bococizumab [Pfizer]), J10 [Pfizer], J16 [Pfizer], J17 [Pfizer], 1D05-IgG2 [Merck], 1B20 [Merck], RG7652 [Roche/Genentech], LGT209 [Novartis], or MEDI-4166 [Astrazeneca].

In another embodiment of the present invention, the PCSK9 inhibitor may be a bispecific antibody, wherein one arm of the bispecific antibody is antagonistic against PCSK9 and another arm is antagonistic against at least one immune checkpoint protein.

In another embodiment of the present invention, the at least one immune checkpoint protein may be selected from the group consisting of PD1, PDL1, CTLA4, LAG3, TIM3, TIGIT, TGF-β, and combinations thereof.

In another embodiment of the present invention, the PCSK9 inhibitor may be a bispecific antibody, wherein one arm of the bispecific antibody is antagonistic against PCSK9 and another arm is agonistic to immunostimulatory targets.

In another embodiment of the present invention, the immunostimulatory targets may be selected from the group consisting of 1BB, OX40, and ICOS.

In another embodiment of the present invention, the PCSK9 inhibitor may be a fusion protein. In preferred embodiments, the fusion protein may be Annexin A2 fusion protein or Annexin A2-Fc fusion protein.

In another embodiment of the present invention, the PCSK9 inhibitor may be an adnectin. In preferred embodiments, the adnectin may be BMS0962476 [Bristol Myers Squib].

In another embodiment of the present invention, the PCSK9 inhibitor may be a single domain antibody to PCSK9.

In another embodiment of the present invention, the PCSK9 inhibitor may be an EDF-A domain mimetic peptide.

In another embodiment of the present invention, the PCSK9 inhibitor may be an RNAi against Alnylam/ALN-PCS02.

In another embodiment of the present invention, the PCSK9 inhibitor may be an RNAi against PCSK9 Alnylam/The Medicines Company/ALN-PCSsc/Inclisaran.

In another embodiment of the present invention, the PCSK9 inhibitor may be an antisense oligonucleotide against PCSK9. In preferred embodiments, the antisense oligonucleotide may be ISIS394814, SPC4061 [Santaris-Pharma], or PSC5011 [Santaris-Pharma].

In another embodiment of the present invention, the PCSK9 inhibitor may be a peptide-based vaccine against PCSK9. In preferred embodiments, the peptide-based vaccine may be AT04A [Affiris] or other PCSK9 vaccines such as those described in WIPO Patent Application Publication No. WO 2011/027257.

In another embodiment of the present invention, the PCSK9 inhibitor may be a small molecule inhibitor. In preferred embodiments, the small molecule inhibitor may be SX-PCSK9 [Serometrix] or other small molecule PCSK9 inhibitors such as those described in WIPO Patent Application Publication No. WO 2014/150395.

In another embodiment of the present invention, the method may further include administering to the individual at least one immune checkpoint inhibitor.

In another embodiment of the present invention, the PCSK9 inhibitor may be administered prior to the administration of at least one checkpoint inhibitor.

In another embodiment of the present invention, the PCSK9 inhibitor may be administered after the administration of at least one immune checkpoint inhibitor.

In another embodiment of the present invention, the PCSK9 inhibitor may be administered concurrently with the at least one immune checkpoint inhibitor.

In another embodiment of the present invention, the at least one immune checkpoint inhibitor may be selected from the group consisting of anti-PD1 antibodies, anti-PDL1 antibodies, anti-CTLA4 antibodies, anti-LAG3 antibodies, anti-TIM3 antibodies, anti-TIGIT antibodies, and combinations thereof.

In another embodiment of the present invention, the method may further include administering to the individual an anti-cancer treatment selected from the group consisting of radiotherapy, conventional chemotherapy, or targeted chemotherapy.

In another embodiment of the present invention, the method may further include administering to the individual at least one inhibitor of an angiogenesis factor.

In another embodiment of the present invention, the at least one angiogenesis factor is selected from the group consisting of inhibitors of VEGF, inhibitors of VEGFR1, inhibitors of VEGFR2, inhibitors of TEK, and combinations thereof.

In another embodiment of the present invention, the at least one inhibitor of an angiogenesis factor comprises a small molecule.

In another embodiment of the present invention, the at least one inhibitor of an angiogenesis factor comprise an antibody.

In another embodiment of the present invention, the at least one inhibitor of an angiogenesis factor comprises a fusion protein.

In another embodiment of the present invention, the cancer may be a solid tumor that expresses PCSK9.

In another embodiment of the present invention, the cancer may be a blood-borne cancer that expresses PCSK9.

DETAILED DESCRIPTION

Figure 1:
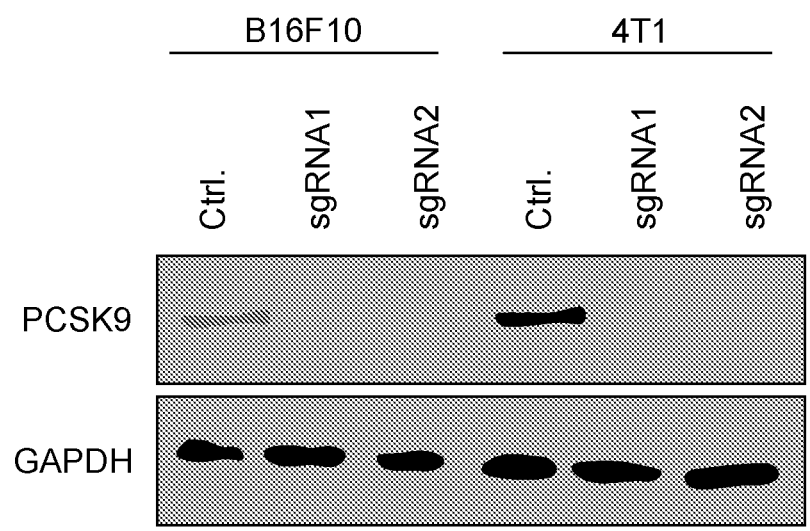
FIG. 1 is a western blot showing the successful knockout of PCSK9 in B26F10 and 4T1 tumor cells: (a) sequence of two sgRNAs used to knockout PCSK9 cells; (b) the sgRNA sequence was cloned into recombinant lentivirus vectors and used to infect B16F10 and 4T1 cells, respectively.

In the following description, for the purposes of explanation, numerous specific details are set forth in order to provide a thorough understanding of the embodiments of the invention. One skilled in the art will recognize that the embodiments of the invention may be practiced without these specific details or with an equivalent arrangement. In other instances, well-known structures and devices are shown in block diagram form in order to avoid unnecessarily obscuring the embodiments of the invention.

The presently disclosed subject matter is presented with sufficient details to provide an understanding of one or more particular embodiments of broader inventive subject matters. The descriptions expound upon and exemplify particular features of those particular embodiments without limiting the inventive subject matters to the explicitly described embodiments and features. Considerations in view of these descriptions will likely give rise to additional and similar embodiments and features without departing from the scope of the presently disclosed subject matter.

Definitions

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

The term "effective amount" or "therapeutically effective amount" refers to an amount sufficient to effect beneficial or desirable biological and/or clinical results.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like.

The term "disease" as used herein includes, but is not limited to, any abnormal condition and/or disorder of a structure or a function that affects a part of an organism. It may be caused by an external factor, such as an infectious disease, or by internal dysfunctions, such as cancer, cancer metastasis, and the like.

As is known in the art, a cancer is generally considered as uncontrolled cell growth. The methods of the present disclosure can be used to treat any cancer, and any metastases thereof, that is characterized by the expression of PCSK9. Such cancers include, but are not limited to, carcinomas, lymphomas, blastomas, sarcomas, and leukemias. More particular examples of such cancers include breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, uterine cervical cancer, endometrial carcinoma, salivary gland carcinoma, mesothelioma, kidney cancer, vulval cancer, pancreatic cancer, thyroid cancer, hepatic carcinoma, skin cancer, melanoma, brain cancer, neuroblastoma, myeloma, various types of head and neck cancer, acute lymphoblastic leukemia, acute myeloid leukemia, Ewing sarcoma and peripheral neuroepithelioma. In some embodiments, the cancer comprises solid tumors that express PCSK9. In other embodiments, the cancer comprises blood-borne cancers that express PCSK9.

As used herein, "proprotein convertase subtilisin kexin 9" or "PCSK9" is meant to refer to refer to any molecule that is capable of reducing the normal activity of PCSK9 within a subject upon or after administration of the inhibitor. PCSK9 is an important protein in LDL cholesterol (LDL-C) metabolism. PCSK9 plays an important role in the degradation of the LDL receptor (LDLR). In LDL metabolism the LDLR binds to LDL in circulating blood and internalizes the LDL into clathrin-coated pits for lysosomal degradation. Following internalization of the LDL, the LDLR is then recycled back to the plasma membrane where it can bind more LDL. This process repeats continuously. However, PCSK9 degradation of the LDLR prevents recycling of the LDLR to the membrane and thus reduces LDL clearance from the blood. Accordingly, PCSK9 has an important target for inhibition for the promotion of reduced LDL-C and thus a therapeutic target for the treatment of hypercholesterolemia and associated cardiovascular diseases. The crystal structure of PCSK9 was described in PCT7US2008/056316. Furthermore, PCT/IB2004/001686 describes mutations in the human PCSK9 gene associated with hypercholesterolemia. PCSK9 is a part of the LDL-C metabolism pathway.

Unless otherwise defined, all technical terms used herein have the same meaning as commonly understood by one of ordinary skill in the art to which this disclosure belongs.

Methods

The present disclosure is based, in part, on the discovery by the inventors that PCSK (proprotein convertase subtilisin/kexin type 9 precursor) is a novel target for cancer treatment. PCSK9 is a secreted protein that is known to play a key role in regulating the LDL-R (low density lipoprotein receptor) levels in hepatocytes and other cell types. PCSK9 negatively regulates LDL-R by binding to it and promoting its degradation inside host cells. Previously it was found that mutations within the PCSK9 genes, depending on whether they enhance or attenuate the LDL-R degradation functions of PCSK9, can lead to dramatically increased or decreased LDL blood concentrations.

In one embodiment of the present invention, a method for treating cancer in an individual may comprise administering to the individual a therapeutically effective amount of a PCSK9 inhibitor. In yet another embodiment of the present invention, the method may further comprise administering to the individual at least one immune checkpoint inhibitor.

Antibodies

In some embodiments, the PCSK9 inhibitor may comprise an antagonistic antibody against PCSK9. The antibody may be monoclonal, polyclonal, single domain, or a fragment thereof. As used herein, "monoclonal antibody" or "MAb" is meant to refer to an antibody from a population of substantially homogeneous antibodies (i.e. where the individual antibodies are identical to one another, with the possible exception of some naturally-occurring mutations). MAbs are highly specific, being directed against a single antigenic site and is often directed against a single determinant on an antigen. The antibodies may further be humanized. As used herein, "humanized" antibody is meant to refer to forms of non-human (e.g., murine) antibodies that are chimeric immunoglobulins, immunoglobulin chains, or fragments thereof (such as Fv, Fab, Fab', F(ab')2 or other antigen-binding subsequences of antibodies) that contain minimal sequence derived from non-human immunoglobulin. Many humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity.

A number of PCSK9 antgonistic/inhibitory antibodies (and fragments thereof) are described in the patent literature as follows and may be suitable for use in the methods provided herein: MERCK/SCHERING CORP. (PCT/US2008/081311); SCHERING CORP. (PCT/US2011/056649); REGENERON PHARMACEUTICALS, INC. (PCT/US2012/054756; PCT/US2012/048574; PCT/US2009/068013); SANOFI (PCT/EP2012/051318; PCT/EP2012/051320; PCT/EP2012/051321); ELI LILLY AND COMPANY (PCT/US2012/054737); AFFIRIS AG (PCT/EP2012/067950); PFIZER (PCT/IB2012/053534; PCT/IB2012/050924; PCT/IB2010/053784); NOVARTIS AG (PCT/EP2012/061045; PCT/US2012/041214; PCT/EP2008/054417); IRM LLC and NOVARTIS AG (PCT7US2012/024633; PCT/US2010/059959); GENENTECH INC. and HOFFMANN LA ROCHE (PCT/US2011/024633); MERCK SHARP & DOHME (PCT/US2010/054714; PCT/US2010/054640; PCT/US2010/048849); RINAT NEUROSCIENCE CORP/PFIZER (PCT/IB2009/053990); MERCK & CO INC. (PCT/US2009/033369; PCT/US2009/033341; PCT/US2007/023223; PCT/US2007/023213; PCT/US2007/023212; PCT/US2007/023169); and AMGEN INC. (PCT/US2008/074097). In other embodiments, antagonistic antibodies against PCSK9 according to methods of the present invention include, but are not limited to, Repatha® (also known as Amgen 145 and evolocumab), Praluent® (also known as REGN 727 [Regeneron] and SAR236553 [Sanofi]), LY3015014 (also known as Frovocimab [Lilly]), RN316 (also known as bococizumab [Pfizer]), J10 [Pfizer], J16 [Pfizer], J17 [Pfizer], 1D05-IgG2 [Merck], 1B20 [Merck], RG7652 [Roche/Genentech], LGT209 [Novartis], and MEDI-4166 [Astrazeneca].

In another embodiment, the PCSK9 inhibitor may comprise a bispecific antibody. In one embodiment, the bispecific antibody may comprise one arm that is antagonistic against PCSK9 and another arm that is antagonistic against at least one immune checkpoint protein. Suitable immune checkpoint proteins include, but are not limited to, PD1, PDL1, CTLA4, LAG3, TIM3, TIGIT, TGF-β, and combinations thereof.

In another embodiment, the bispecific antibody may comprise one arm that is antagonistic against PCSK9 and another arm that is agonistic to immunostimulatory targets. Suitable immunostimulatory targets include, but are not limited to, 1BB, OX40 and ICOS.

Fusion Proteins

In another embodiment, the PCSK9 inhibitor may comprise a fusion protein. Fusion proteins, or chimeric proteins, refer to those proteins created through the joining of two or more genes that originally coded for separate proteins. In one embodiment, the PCSK9 inhibitor may comprise an Annexin A2 fusion protein. In another embodiment, the PCSK9 inhibitor may comprise an Annexin A2-Fc fusion protein.

Adnectin

In another embodiment, the PCSK9 inhibitor may comprise an adnectin. As used herein, the term "adnectin" refers to those therapeutic proteins that are based on the $10^{th}$ fibronectin type III domain and are designed to bind with high affinity and specificity to therapeutically relevant targets. Suitable examples include, but are not limited to, the PCSK9 inhibitor BMS-962476 (Bristol Myers Squibb).

RNAi

The PCSK9 inhibitory molecule may further comprise an RNAi. 'RNAi' as used herein is meant to include any of the gene silencing methods known in the art, including post-transcriptional gene silencing (PTGS) methods. These may include, but are not limited to any one or more of the following: microRNA (miRNA); small interfering (siRNA); short-hairpin RNA (shRNA); primary-microRNA (pri-miRNA); asymmetric interfering RNA (aiRNA); small internally segmented RNS (sisiRNA); meroduplex RNA (mdRNA); RNA-DNA chimeric duplex; trans-kingdom RNA (tkRNA); tRNA-shRNA; tandem siRNA (tsiRNA); tandem hairpin RNA (thR A); pri-miRNA mimic cluster; and transcriptional gene silencing (TGS). In one embodiment, the PCSK9 inhibitor may comprise an EDF-A domain mimetic peptide. In another embodiment, the PCSK9 inhibitor may comprise an RNAi against PCSK9 Alnylam/ALN-PCS02. In yet another embodiment, the PCSK9 inhibitor may comprise an RNAi against PCSK9 Alnylam/The Medicines Company/ALN-PCSsc/Inclisaran.

Oligonucleotides

In other embodiments, the PCSK9 inhibitor may comprise an antisense oligonucleotide. Examples include PCSK9 antisense oligonucleotide from Isis Pharmaceuticals/Bristol-Myers Squibb (ISIS 394814; BMS-PCSK9Rx). Similarly, a locked nucleic acid from Santaris Pharma (SPC4061; SPC5011; LNA ASO) reduced PCSK9 mRNA levels in mice. LNA ASO is complementary to the human and mouse PCSK9 mRNA (accession #NM174936 and NM153565) is a 13-nucleotide long gapmer with the following sequence: GTctgtggaaGCG (uppercase LNA, lowercase DNA) and phos-phorothioate internucleoside linkages. Alnylam Pharmaceuticals has shown positive results in clinical trials for an siRNA (ALN-PCS) for the inhibition of PCSK9. A number of PCSK9 inhibitory oligonucleotides are described in the patent literature as follows and are within the scope of the present disclosure: SANTARIS PHARMA A/S (PCT/EP2007/060703; PCT/EP2009/054499; PCT/EP2010/059257); ISIS PHARMACEUTICAL INC. (PCT/US2007/068404); SIRNA THERAPEUTICS INC. (PCT/US2007/073723); ALNYLAM PHARMACEUTICALS INC. (PCT/US2011/058682; PCT/US2010/047726; PCT/US2010/038707; PCT/US2009/032743; PCT/US2007/068655); RXI PHARMACEUTICALS CORP. (PCT/US2010/000019) INTRADIGM CORP. (PCT/US2009/036550); and NAS-TECH PHARM CO. (PCT/US2008/055554).

Peptide-Based Vaccine

In another embodiment of the present invention, the PCSK9 inhibitor may be a peptide-based vaccine against PCSK9. In preferred embodiments, the peptide-based vaccine may be AT04A [Affiris] or other PCSK9 vaccines such as those described in WIPO Patent Application Publication No. WO 2011/027257.

Small Molecules

In another embodiment of the present invention, the PCSK9 inhibitor may be a small molecule inhibitor. In preferred embodiments, the small molecule inhibitor may be SX-PCSK9 [Serometrix] or other small molecule PCSK9 inhibitors such as those described in WIPO Patent Application Publication No. WO 2014/150395. The above description and drawings are illustrative and are not to be construed as limiting the invention to the precise forms disclosed. Persons skilled in the relevant art can appreciate that many modifications and variations are possible in light of the above disclosure. Numerous specific details are described to provide a thorough understanding of the disclosure. However, in certain instances, well-known or conventional details are not described in order to avoid obscuring the description.

Peptides

Peptides that mimic the EGFA domain of the LDLR that binds to PCSK9 have been developed to inhibit PCSK9. Similarly, EGF-A peptides, fibronectin based scaffold domain proteins, which bind PCSK9, and neutralizing PCSK9 variants (for example, with a Pro/Cat domain), have been developed and all of which have been shown to inhibit PCSK9 activity. A number of PCSK9 inhibitory peptides are described in the patent literature as follows and are within the scope of the present disclosure: SCHERING CORP. (PCT US2009/044883); GENENTECH INC. and HOFFMANN LA ROCHE (PCT US2012/043315); SQUIBB BRISTOL MYERS CO. (PCT/US201 1/032231; PCT/US2007/015298); ANGELETTI P IST RICHERCHE BIO (PCT/EP2011/054646); and AMGEN INC. (PCT/US2009/034775).

Therapeutic Administration and Pharmaceutical Formulations

The administration of therapeutic compositions in accordance with the present invention may be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN®), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See, e.g., Powell et al. "Compendium of excipients for parenteral formulations" PDA (1998) *J Pharm Sci Technol* 52:238-311.

The dose may vary depending upon the age and the size of a subject to be administered, target disease, conditions, route of administration, and the like. When the PCSK9 inhibitor of the present disclosure is used for treating various conditions and diseases associated with PCSK9, including cancer and the like, in an adult patient, it may be advantageous to intravenously administer the PCSK9 inhibitor of the present disclosure normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment may be adjusted.

Various delivery systems are known and may be used to administer the pharmaceutical composition of the present disclosure, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction may include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration may be systemic or local.

The pharmaceutical composition may be also delivered in a vesicle, in particular a liposome (see, e.g., Langer (1990) Science 249:1527-1533; Treat et al. (1989) in Liposomes in the Therapy of Infectious Disease and Cancer, Lopez Berestein and Fidler (eds.), Liss, New York, pp. 353-365; Lopez-Berestein, ibid., pp. 317-327; see generally ibid.).

In certain embodiments, the pharmaceutical composition may be delivered in a controlled release system. In one embodiment, a pump may be used (see Langer, supra; Sefton (1987) CRC Crit. Ref. Biomed. Eng. 14:201). In another embodiment, polymeric materials as described in Medical Applications of Controlled Release, Langer and Wise (eds.), CRC Pres., Boca Raton, Florida (1974) may be used. In yet another embodiment, a controlled release system may be placed in proximity of the composition's target, thus requiring only a fraction of the systemic dose (see, e.g., Goodson, in Medical Applications of Controlled Release, supra, vol. 2, pp. 115-138, 1984).

In other embodiments of the present invention, injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the PCSK9 inhibitor (e.g., antagonistic antibody or its salt) described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule. A pharmaceutical composition of the present disclosure may be delivered subcutaneously or intravenously with a standard needle and syringe. In addition, with respect to subcutaneous delivery, a pen delivery device readily has applications in delivering a pharmaceutical composition of the present disclosure. Such a pen delivery device may be reusable or disposable. A reusable pen delivery device generally utilizes a replaceable cartridge that contains a pharmaceutical composition. Once all of the pharmaceutical composition within the cartridge has been administered and the cartridge is empty, the empty cartridge may readily be discarded and replaced with a new cartridge that contains the pharmaceutical composition. The pen delivery device may then be reused. In a disposable pen delivery device, there is no replaceable cartridge. Rather, the disposable pen delivery device may come prefilled with the pharmaceutical composition held in a reservoir within the device. Once the reservoir is emptied of the pharmaceutical composition, the entire device may be discarded.

Numerous reusable pen and autoinjector delivery devices have applications in the subcutaneous delivery of a pharmaceutical composition of the present disclosure. Examples include, but certainly are not limited to AUTOPEN® (Owen Mumford, Inc., Woodstock, UK), DISETRONIC® pen (Disetronic Medical Systems, Burghdorf, Switzerland), HUMALOG MIX 75/25® pen, HUMALOG® pen, HUMALIN 70/30® pen (Eli Lilly and Co., Indianapolis, Ind.), NOVOPEN® I, II and III (Novo Nordisk, Copenhagen, Denmark), NOVOPEN JUNIOR® (Novo Nordisk, Copenhagen, Denmark), BD® pen (Becton Dickinson, Franklin Lakes, N.J.), OPTIPEN®, OPTIPEN PRO®, OPTIPEN STARLET®, and OPTICLIK® (sanofi-aventis, Frankfurt, Germany), to name only a few. Examples of disposable pen delivery devices having applications in subcutaneous delivery of a pharmaceutical composition of the present disclosure include, but certainly are not limited to the SOLOSTAR® pen (sanofi-aventis), the FLEXPEN® (Novo Nordisk), and the KWIKPEN® (Eli Lilly).

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Dosage

The amount of PCSK9 inhibitor administered to an individual according to the some methods of the present invention may be, generally, a therapeutically effective amount. In the case of PCSK9 inhibitor that comprises an antibody, a therapeutically effective amount may be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 75 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the PCSK9 inhibitor.

The amount of PCSK9 inhibitor contained within the individual doses may be expressed in terms of milligrams of antibody per kilogram of patient body weight (i.e., mg/kg). For example, the anti-PCSK9 antibody may be administered to a patient at a dose of about 0.0001 to about 10 mg/kg of patient body weight.

Administration Regimens

According to certain embodiments of the present invention, multiple doses of a PCSK9 inhibitor may be administered to a subject over a defined time course. The methods according to this aspect of the present invention may comprise sequentially administering to a subject multiple doses of a PCSK9 inhibitor. As used herein, "sequentially administering" means that each dose of PCSK9 inhibitor is administered to the subject at a different point in time, e.g., on different days separated by a predetermined interval (e.g., hours, days, weeks or months). The present invention includes methods which may comprise sequentially administering to the patient a single initial dose of a PCSK9 inhibitor, followed by one or more secondary doses of the PCSK9 inhibitor, and optionally followed by one or more tertiary doses of the PCSK9 inhibitor.

The terms "initial dose," "secondary doses," and "tertiary doses," refer to the temporal sequence of administration of the PCSK9 inhibitor. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of PCSK9 inhibitor, but will generally differ from one another in terms of frequency of administration. In certain embodiments, however, the amount of PCSK9 inhibitor contained in the initial, secondary and/or tertiary doses will vary from one another (e.g., adjusted up or down as appropriate) during the course of treatment.

In certain exemplary embodiments of the present disclosure, each secondary and/or tertiary dose is administered 1 to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more) days after the immediately preceding dose, or 1 to 12 (e.g., 1, 2, 3, 4, 5, 6, 7, 8, 9, 10, 11, 12, or more) weeks after the immediately preceding dose. The phrase "the immediately preceding dose," as used herein, means, in a sequence of multiple administrations, the dose of PCSK9 inhibitor which is administered to a patient prior to the administration of the very next dose in the sequence with no intervening doses.

The methods according to this aspect of the present invention may comprise administering to a patient any number of secondary and/or tertiary doses of a PCSK9 inhibitor. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 12 weeks after the immediately preceding dose (e.g., once every week [Q1W], once every two weeks [Q2W], once every three weeks [Q3W], once every four weeks [Q4W], once every six weeks [Q6W], once every eight weeks [Q8W], etc.). Similarly, in embodiments involving multiple tertiary doses, each tertiary dose may be administered at the same frequency as the other tertiary doses. For example, each tertiary dose may be administered to the patient 1 to 12 weeks after the immediately preceding dose (e.g., once every week [Q1W], once every two weeks [Q2W], once every three weeks [Q3W], once every four weeks [Q4W], once every six weeks [Q6W], once every eight weeks [Q8W], etc.). Alternatively, the frequency at which the secondary and/or tertiary doses are administered to a patient may vary over the course of the treatment regimen. The frequency of administration may also be adjusted during the course of treatment by a physician depending on the needs of the individual patient following clinical examination.

Combination and Adjunct Therapies

The methods of the present invention, according to certain embodiments, may comprise administering a pharmaceutical composition comprising a PCSK9 inhibitor to a patient who is on an anti-cancer therapeutic regimen for the treatment of cancer at the time of, or just prior to, administration of the pharmaceutical composition of the present disclosure. For example, a patient who has previously been diagnosed with a cancer (e.g., a solid tumor or a blood-borne cancer) characterized with PCSK9 expression may have been prescribed and is taking a stable therapeutic regimen of another drug prior to and/or concurrent with administration of a pharmaceutical composition comprising a PCSK9 inhibitor. For example, in one embodiment, the PCSK9 inhibitor may be administered concurrently with at least one immune checkpoint inhibitor, an anti-cancer treatment, and/or inhibitor of an angiogenesis factor. In other embodiments, the PCSK9 inhibitor may be administered prior to the administration of at least one immune checkpoint inhibitor, an anti-cancer treatment, and/or inhibitor of an angiogenesis factor. In yet other embodiments, the PCSK9 inhibitor may be administered after the administration of at least one immune checkpoint inhibitor, an anti-cancer treatment, and/or inhibitor of an angiogenesis factor.

In some embodiments, the immune checkpoint inhibitor may be selected from the group consisting of anti-PD1 antibodies, anti-PDL1 antibodies, anti-CTLA4 antibodies, anti-LAG3 antibodies, anti-TIM3 antibodies, anti-TIGIT antibodies, and combinations thereof.

In another embodiment, the anti-cancer treatment may be selected from the group consisting of radiotherapy, conventional chemotherapy, or targeted chemotherapy.

In yet another embodiment, the inhibitor of the angiogenesis factor may be selected from the group consisting of inhibitors of VEGF, inhibitors of VEGFR1, inhibitors of VEGFR2, inhibitors of TEK and combinations thereof. In other embodiments, the inhibitors of angiogenesis factors may comprise, consist or consist essentially of a small molecule. In yet other embodiments, the inhibitors of angiogenesis factors may comprise, consist, or consist essentially of an antibody. In other embodiments, the inhibitors of angiogenesis factors may comprise, consist, or consist essentially of a fusion protein.

The following Examples are provided by way of illustration and not by way of limitation.

Example 1

Figure 2A:
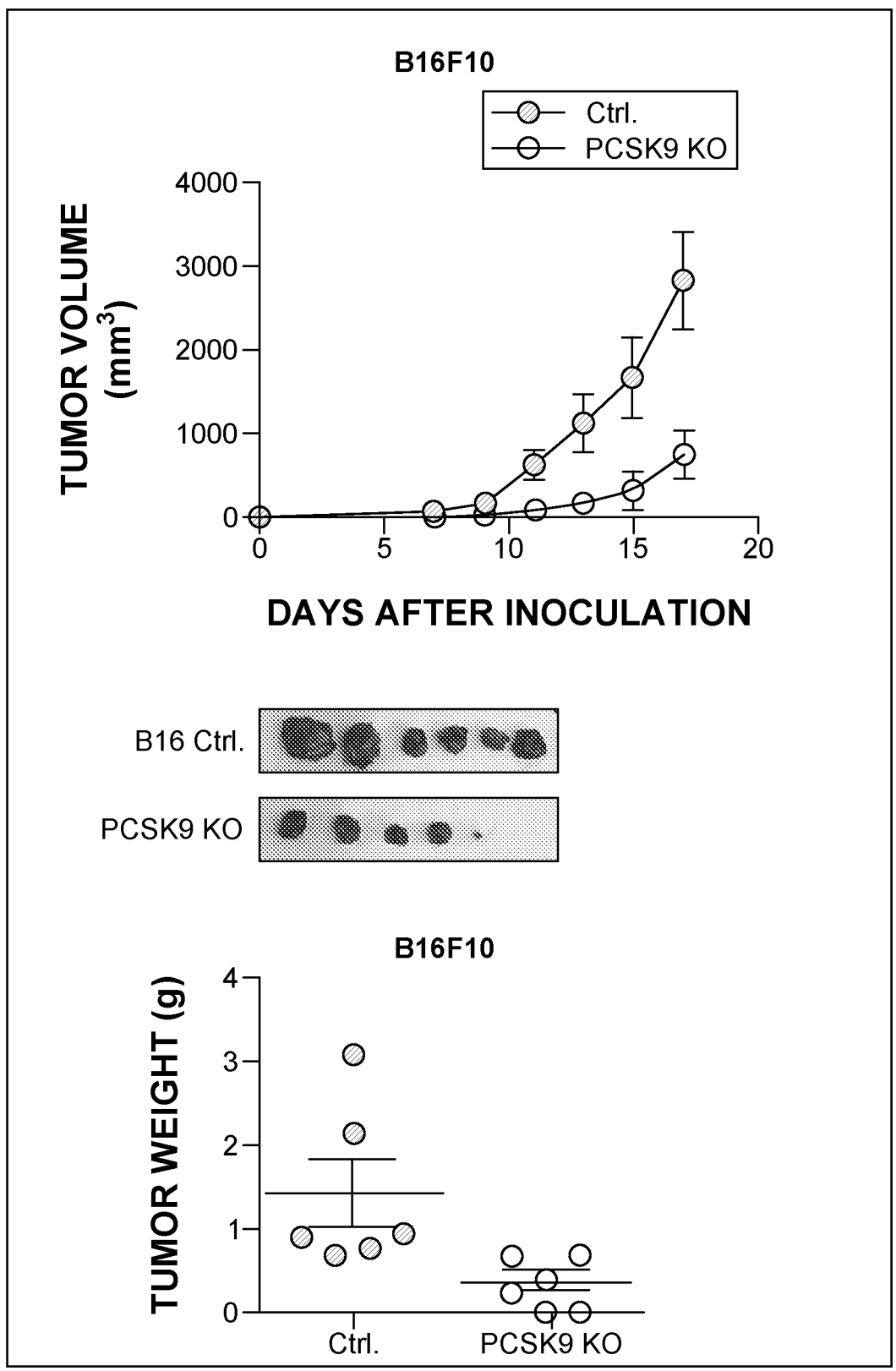
FIG. 2A illustrates images and graphs showing the effect of PCSK knockout on tumor growth significantly slowed tumor growth in the B16F10 model in C57/BL/6 mice.
Figure 2B:
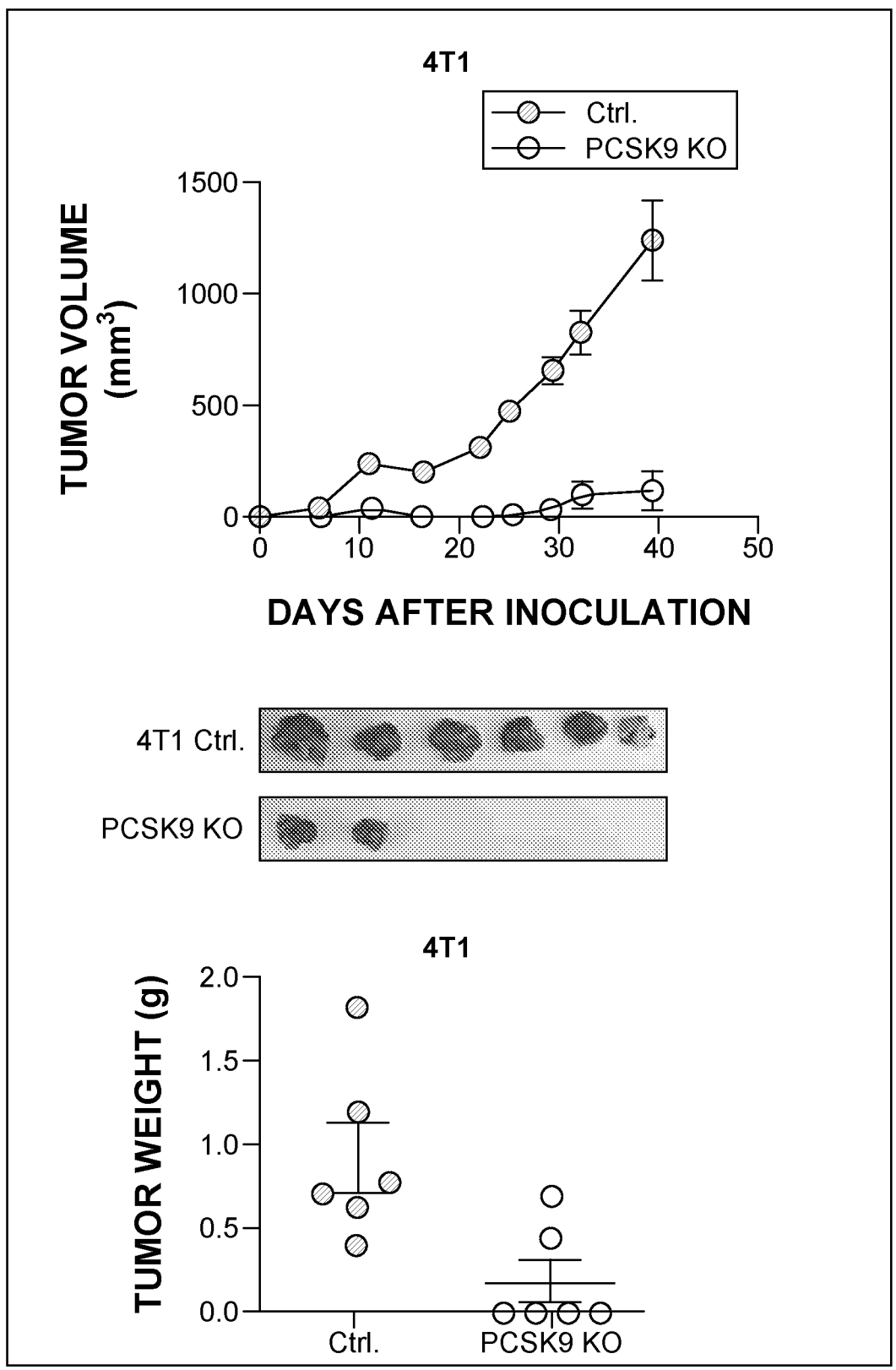
FIG. 2B illustrates images and graphs showing the effect of PCSK9 knockout on tumor growth significantly attenuated tumor growth in the 4T1 tumor model.

Referring now to FIGS. 1 2A, and 2B, the inhibition of PCSK9 can significantly attenuate tumor growth in vivo. The two sgRNA sequences identified in FIG. 1 were cloned into recombinant lentivirus vectors and used to infect B16F10 and 4T1 cells, respectively. The western blot analysis demonstrates successful knockout of PCSK9 in B16F10 and 4T1 cells using either sgRNA sequence.

FIGS. 2A and 2B demonstrate that knocking out PCSK9 significantly slows tumor growth in vivo in B16F10 cells and significantly attenuates tumor growth in vivo in 4T1 cells in C57BL/6 mice. The top graph depicts tumor respective tumor growth curves, the middle panels depict respective tumor size after at the end of animal sacrifice, and the lower graphs depict tumor weight. N=6 in both the B16F10 and 4T1 experiments.

Figure 3:
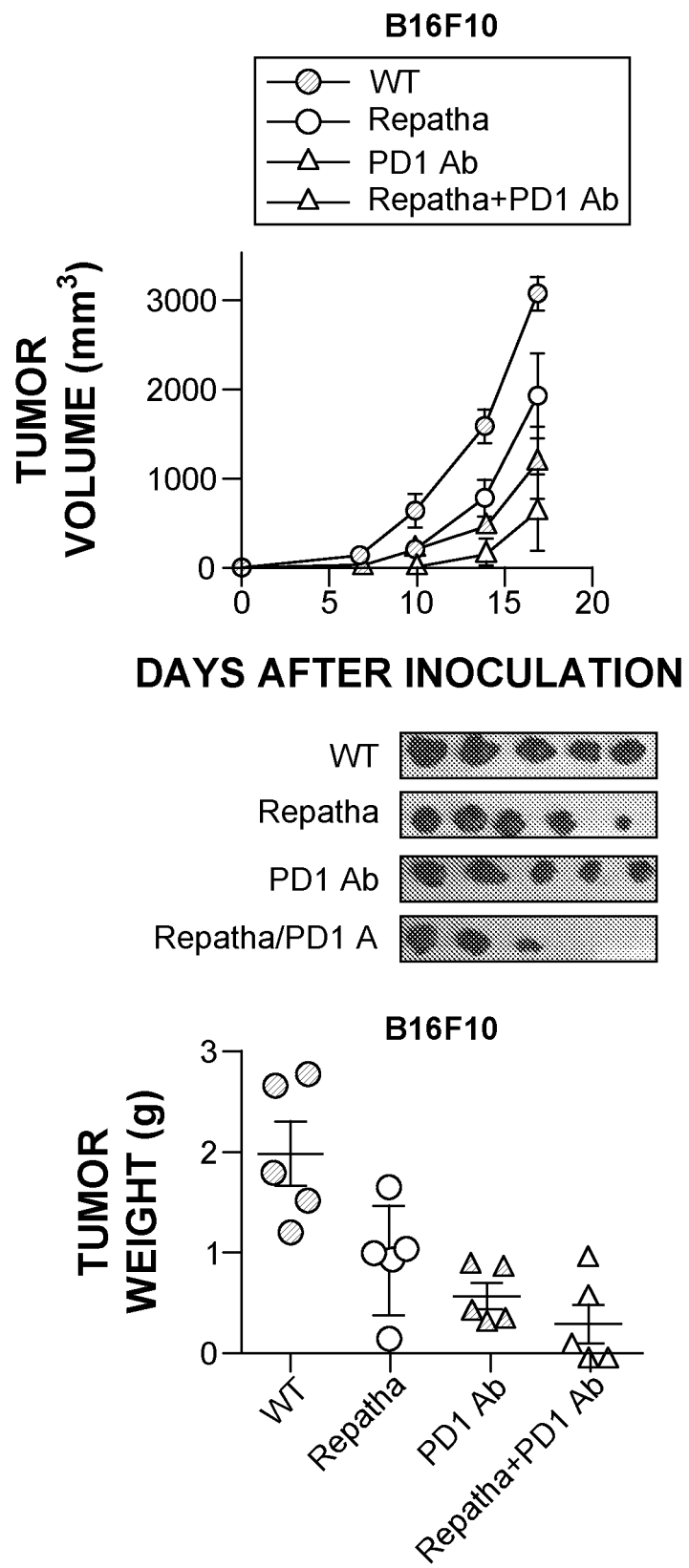
FIG. 3 are images and graphs showing the enhancement of PD1 antibody based immune checkpoint inhibitor therapy in the B16F10 melanoma model by the PCSK9 antibody Repatha®.
Figure 4A:
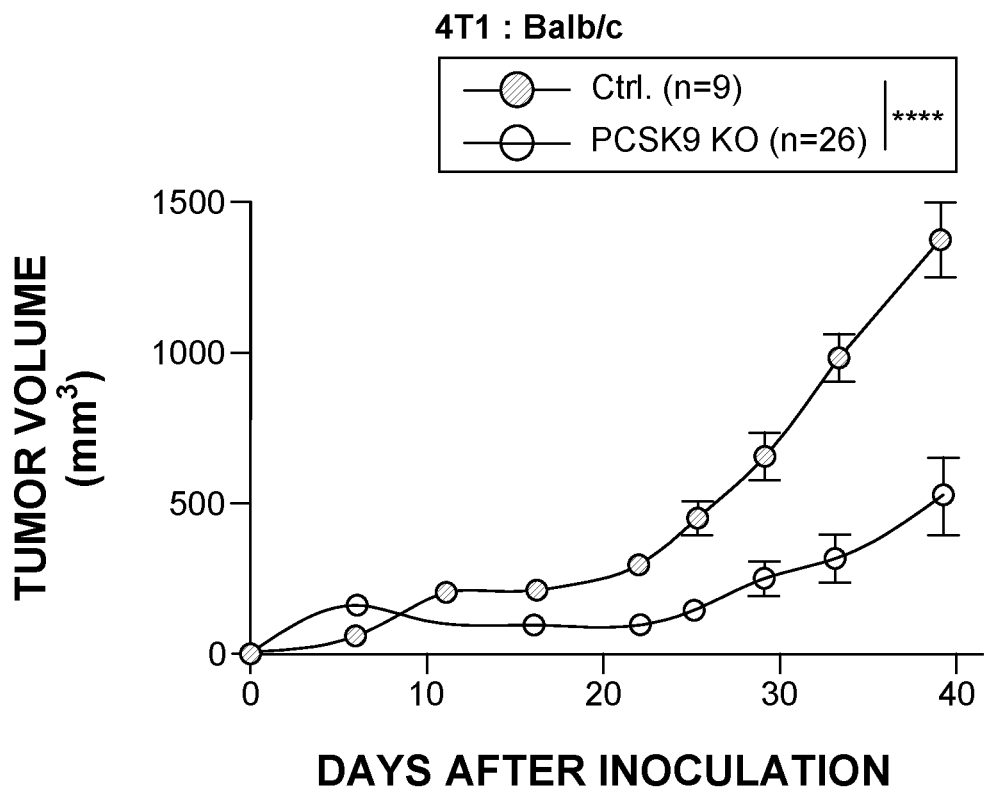
FIGS. 4A-4H are images and graphs showing PCSK9 deficiency induced tumor growth suppression.
Figure 4B:
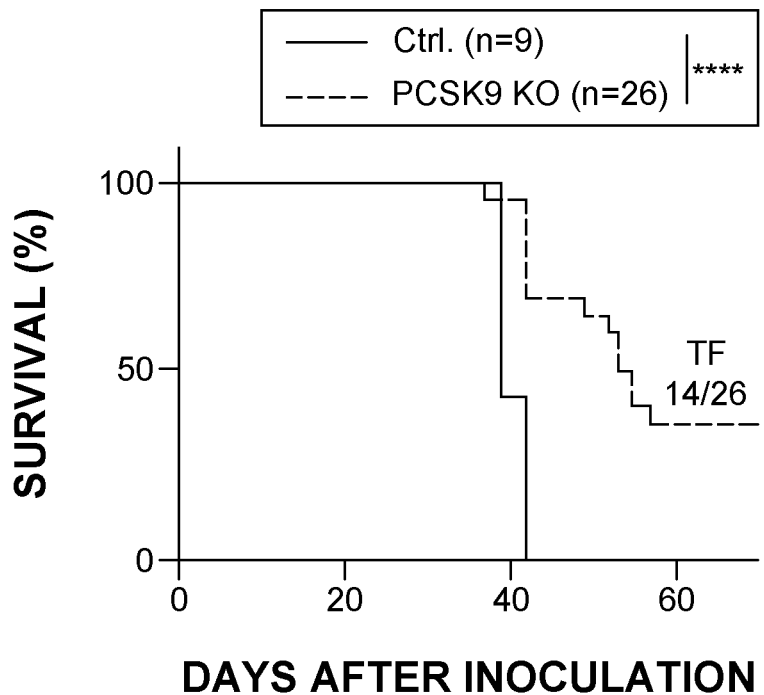
Figure 4C:
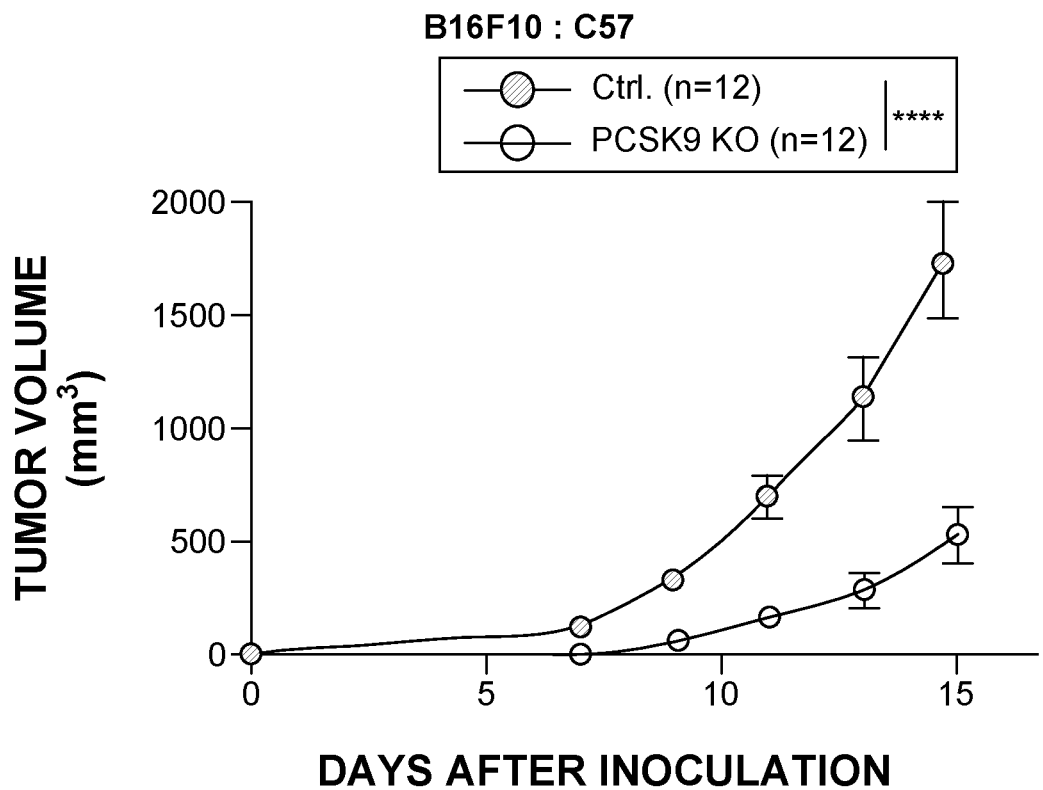
Figure 4D:
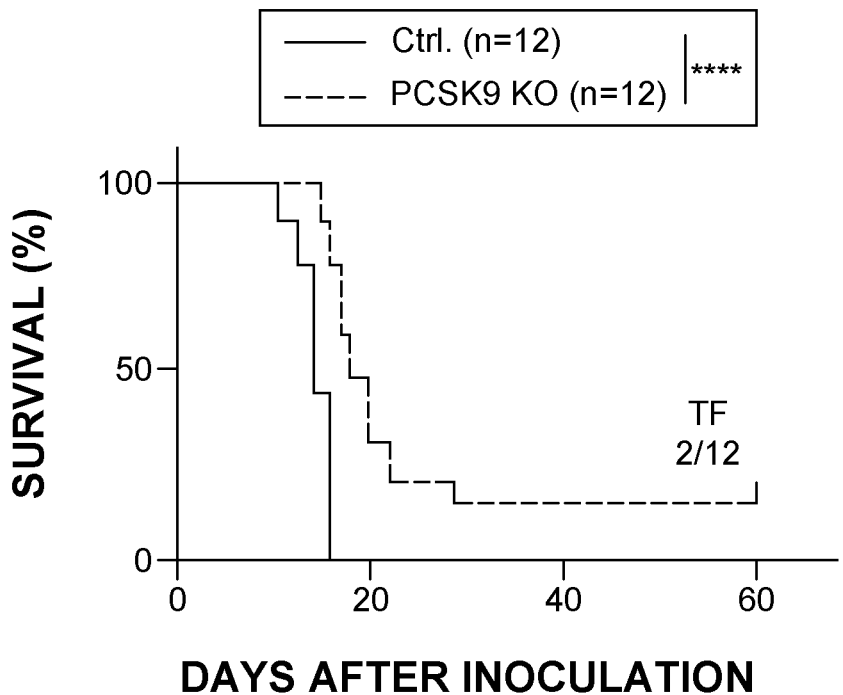
Figure 4E:
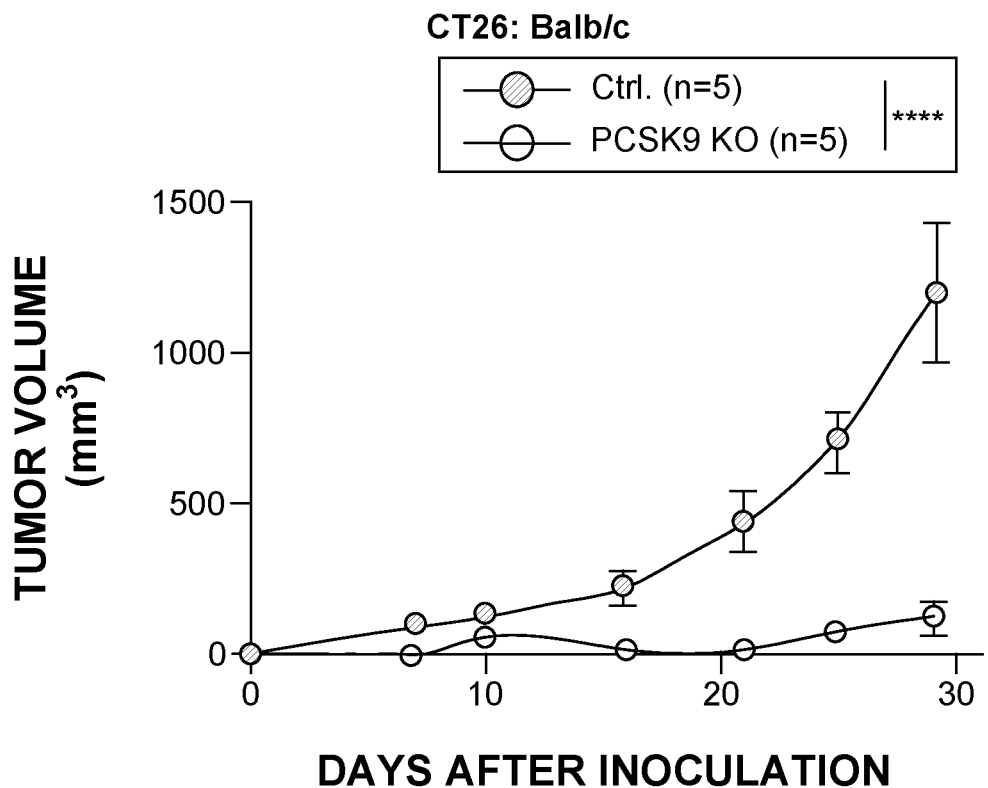
Figure 4F:
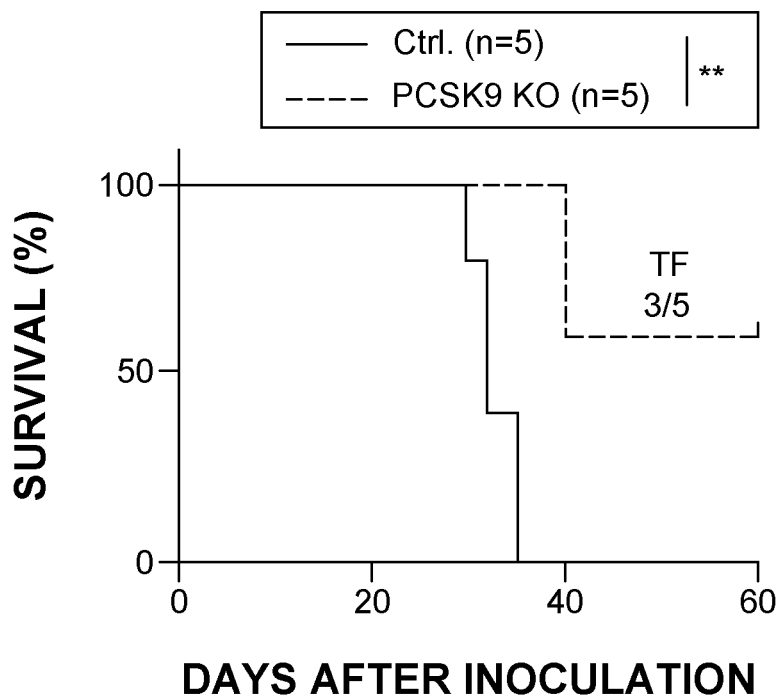
Figure 4G:
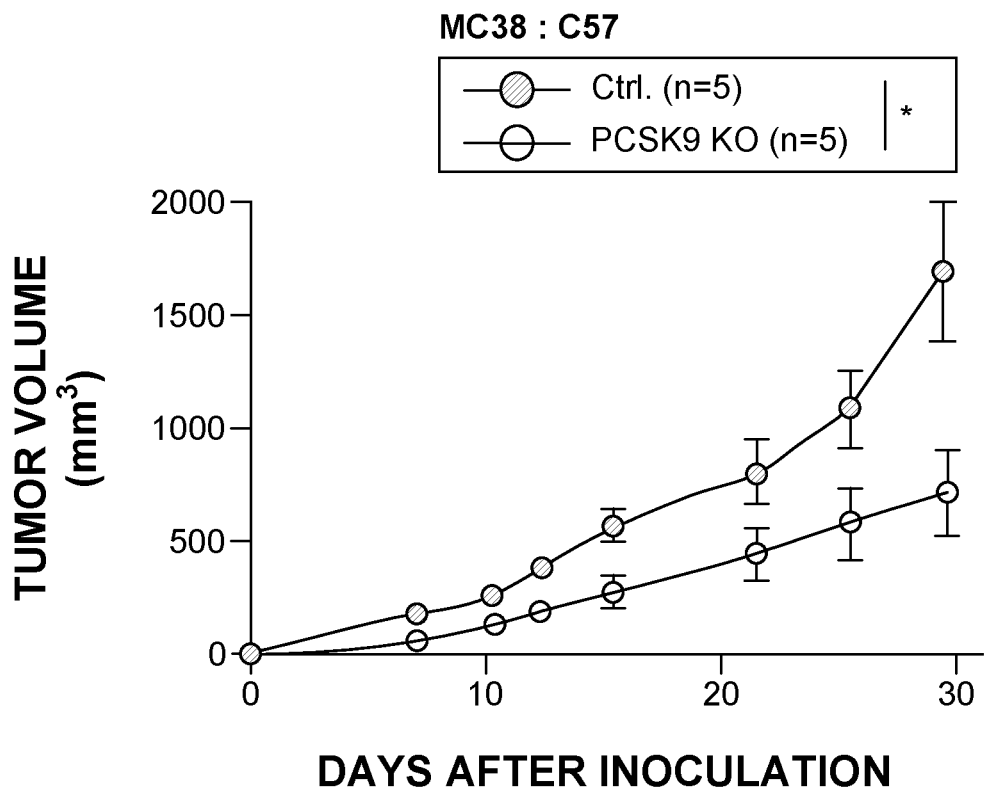
Figure 4H:
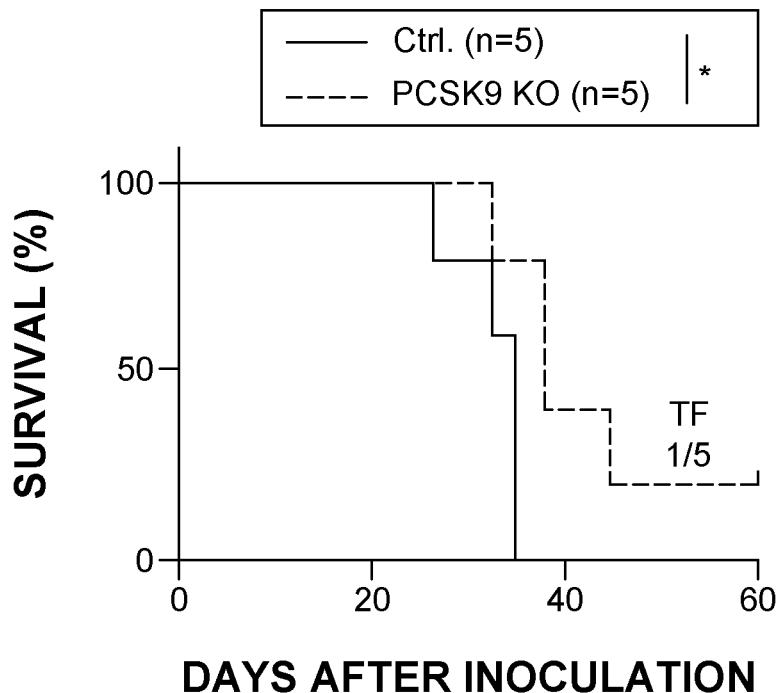

Referring now to FIG. 3, the inhibition of PCSK9 can be synergized with immune checkpoint therapy and other established cancer therapeutic methods such as radiotherapy, conventional chemotherapy, and targeted chemotherapy to further attenuate tumor growth. FIG. 3 depicts results from various combinations of PCSK9 inhibition, antagonistic antibody Repatha® (also known as Amgen 145 and evolocumab), and immune checkpoint inhibitor anti-PD1 antibodies in B16F10 melanoma models. The top graph depicts tumor respective tumor growth curves, the middle panels depict respective tumor size after at the end of animal sacrifice, and the lower graphs depict tumor weight, n=5. In two of the five mice, no tumors were present at the end of the experiment using a combination of all three treatments.

Example 2

PCSK9 genes were knocked out in four malignant murine cancer cell lines (B16F10, 4T1, MC38, CT26) by use of the CRISPR-Cas9 technology. PCSK9 knockout did not alter the morphology or the in vitro growth rates of tumor cells or their abilities to form 3D colonies in soft agar.

Materials and Methods

Cell Lines and Tissue Culture

B16F10 mouse melanoma cells, CT26 mouse colon carcinoma, 4T1 mouse breast carcinoma cells, MDA-MB-231 human breast cancer cells were purchased from the Cell Culture Facility of Duke University School of Medicine. MC38 mouse colon adenocarcinoma cells were obtained from Dr. Takuya Osada (Duke University, School of Medicine). B16F10, CT26, 4T1, MC38, MDA-MB-231 cells were all grown in DMEM (Sigma) with 10% fetal bovine serum (FBS) and 100 Units/ml penicillin and 100 μg/ml streptomycin antibiotics. All cell lines were subjected to mycoplasma test periodically by use of the Universal Mycoplasma Detection Kit (ATCC).

CRISPR/Cas9-Mediated Gene Knockout of PCSK9

PCSK9 knockout cells were generated by use of lentivirus mediated CRISPR/Cas9 technology. Single guided RNA (sgRNA) sequences targeting PCSK9 gene were designed with the use of an online CRISPR design tool (chopchop). sgRNA sequences targeting mouse and human PCSK9 gene are listed in Table 1 below. Double stranded oligonucleotides encoding the sgRNA sequences were cloned into BsmB1 (Thermal Fisher Scientific) digested plasmid LentiCRISPRv2 (deposited by Dr. Feng Zhang of MIT to Addgene, Cambridge, MA), which co-expresses Cas9 and sgRNA in the same vector. The sgRNA-encoding CRISPR lentivirus vectors were then produced according to an established protocol by the Zhang lab. To generate the knockout cell lines, target cells were infected with sgRNA-encoding CRISPR lentivirus and cultured in DMEM with 10% FBS and selected in puromycin (1 μg/ml for B16F10, CT26, MC38, MDA-MB-231 and 4 g/ml for 4T1) for 7-10 days. Expression of PCSK9 protein in infected cells were detected by western blot to verify the knockdown. In general, a mixed population of PCSK9 knockout cells were grown for 10-12 days in vitro before being used for experiments.

TABLE 1

| sgRNA sequence targeting mouse and human PCSK9 | |
|---|---|
| | Target sequence |
| mousePCSK9 sgRNA1 | 5'-CATGCTTCATGTCACAGAGT-3' |
| mousePCSK9 sgRNA2 | 5'-TCATTTGACGCTGTCTGGGG-3' |
| humanPCSK9 sgRNA1 | 5'-CAGATGGGGTCTTACCGGG-3' |
| humanPCSK9 sgRNA2 | 5'-TCTTGGTGAGGTATCCCCGG-3' |

Soft Agar Colony Formation Assay

To measure the ability of PCSK9 deficient tumor cells to grow in 3D, soft agar assay was performed according to an established protocol. Cells were seeded at a density of 10,000 cells per well in 6-well plates in duplicate. The colonies were fixed and stained with 0.005% crystal violet after 3 weeks culture. The number of colonies per well were then counted. Two independent experiments were carried out.

Tumor Growth in Mice

All animal experiments conducted in this study were approved by Duke University Institutional Animal Use and Care Committee. C57BL/6J, Balb/c mice and OT-1 transgenic mice (in the C57BL/6 background) were purchased from the Jackson Laboratory (Bar Harbor, ME). NOD CRISPR Prkdeil2rGamma (NCG) triple-immunodeficient mice were purchased from Charles River Laboratory (Wilmington, MA). Prior to tumor cell injection, age-matched, 6-8 weeks old mice were shaved at flank. Tumor cells were then injected into shaved flank subcutaneously with a $1.0 \times 10^5$ CRISPR/Cas9 modified control or target gene knockout tumor cells.

In experiments involving the PCSK9 neutralization antibodies, C57BL/6 mice were inoculated subcutaneously with $2.5 \times 10^5$ MC38 colon cancer cells and injected (intraperitoneally) with 200 µg human IgG2 isotype control (BioXcell) on days 3, 5, 8, and 11. In addition, about 100 µg anti-PD1 (Clone:RMP1-14, BioXcell) antibodies were injected on days 5 and 8 in some mice in combination with the anti-PCSK9 antibodies. Mice were monitored for tumor growth every 2-3 days afterwards. Tumor size was measured by use of a caliper. Death was defined as the point at which a progressively growing tumor reached 1.5 cm in the longest dimension.

Lymphocyte Depletion

To evaluate the role of specific subsets of immune effector cells in mice, CD4+ T cells, CD8+ T cells, and NK cells were depleted with 150 µg of i.p. injected anti-CD4 (GK1.5), 100 µg of anti-CD8β (53-5.8), and 200 µg of anti-NK1.1 (PK136) purchased form BioXcell, respectively on days-3, 0, 3 and 8. Equal amounts of IgG isotype antibodies (BioXcell) were injected as a control.

In Vivo Competition Assay

B16F10 cells stably expressing EGFP or tdTomato were infected with PCSK9-targeting (sgRNA1, sgRNA2 in Table 1) or control lentiviral vectors, respectively and selected with 1 µg/ml puromycin for 10 days. Subsequently, about $5 \times 10^4$ PCSK9 knockout cells (EGFP expressing) and $5 \times 10^4$ control cells (tdTomato expressing) were mixed and inoculated subcutaneously to C57BL/6J female mice. Tumors were excised 12-14 days after inoculation. They were then minced and incubated in DNase I (50 µg/ml, Sigma) and collagenase P (2 mg/ml, Sigma) for 20 min at 37° C. The dissociated tumor cells were passed through 70 µm cell strainer (BD). Tumor cells were washed and re-suspended in ice-cold PBS with 2% FBS. The ratio of GFP and tdTomato tumor cells were analyzed by use of BD Canto flow cytometry system (Flow Cytometry Shared Facility, Duke University School of Medicine).

Analysis of Cell Surface MHC-I Expression by Flow Cytometry

For in vivo experiments, PCSK9-deficient (FGP expressing) or control vector (tdTomato expressing) B16F10 cells were inoculated separately into mice and tumors were harvested 10-12 days later. Tumor cells were then disaggregated and processed as described above and subjected to flow cytometry analysis by use of an anti-H-2K$^b$/H-2 D$^b$ antibody (28-8-6, BioLegend).

For in vitro experiments, B16 F10, 4T1, human MDA-MB-231 cells were stained with anti-H-2K$^b$/H-2 D$^b$ (28-8-6, BioLegend), or anti-H-2K$^d$/H-2D$^d$ (34-1-2S, BioLegend), or HLA-A2 (BB7.2) antibodies, respectively for 20 min on ice. For some experiments, cells were treated with interferon gamma (IFNγ, 4T1: 4 ng/ml; B16F10, 1 ng/ml) for 12 hours to stimulate MHC I expression. After washing with PBS+2% PBS, the expression levels of MHC I surface molecular was analyzed by use of BD Canto flow cytometry system (Flow Cytometry Shared Facility, Duke University School of Medicine).

Analysis of Tumor-Infiltrating Lymphocytes by Flow Cytometry

B16F10 cells were infected with PCSK9-targeting or control lentiviral vectors and selected with 1 g/ml puromycin for 10 days. About $1 \times 10^5$ PCSK9 knockout or control cells were then inoculated subcutaneously into C57BL/6J mice. Tumors were collected on day 12 after inoculation, weighted, and mechanically minced and incubated in DNase I (50 µg/ml, Sigma) and collagenase P (2 µg/ml, Sigma) for 20 min at 37° C. The dissociated cells were passed through 70 µm cell strainer (BD). The filtered cells were then blocked with anti-CD16/32 antibody (BioLegend) and stained with indicated surface antibodies for 20 min on ice. Dead cells were excluded using Live/Dead Fixable Aqua dye (Thermo Fisher Scientific). Intracellular antibodies were added after fixation and permeabilization as per the manufacturer's instruction (Thermo Fisher Scientific). The anti-mouse fluorochrome-conjugated antibodies are listed in Table 2. The stained cells were analyzed by use of a BD Canto flow cytometry system.

TABLE 2

| Antibodies used in the study | | | | |
|---|---|---|---|---|
| Markers | Formats | Clone | Catalog# | Usage |
| Mouse CD45 | FITC | 30-F11 | Biolegend, 103108 | FC |
| Mpuse CD3 | Paific Blue | 145-2e11 | Biolegend, 100334 | FC |
| Mouse CD4 | Alexa Fluor647 | GK1.5 | Biolegend, 100424 | FC |
| Mouse CD8a | APC/Fore 750 | 53-6.7 | Biolegend, 100766 | FC |

TABLE 2-continued

Antibodies used in the study

| Markers | Formats | Clone | Catalog# | Usage |
|---|---|---|---|---|
| Mouse NK1.1 | PE | PK136 | Biolegend, 108707 | FC |
| Mouse Foxp3 | PE | MF-14 | Biolegend, 126403 | FC |
| Mouse TCR γ/δ | APC | GL3 | Biolegend, 118115 | FC |
| Mouse Gzmb | PE | QA16A62 | Biolegend, 372207 | FC |
| Mouse IFNγ | Alexa Fluor647 | XMG1.2 | Biolegend, 505816 | FC |
| Human HLA-A2 | FITC | BB7.2 | Biolegend, 343322 | FC |
| Mouse H-2Kb/H-2Db | FITC | 28-8-6 | Biolegend, 114605 | FC |
| Mouse H-2Kd/H-2Dd | FITC | 34-1-2S | Biolegend, 114706 | FC |
| mouse H-2Kb bound to SINFEKL | PE/Cy7 | 25-D1.16 | Biolegend, 141607 | FC |
| TruStainfeX ™ (anti-mouse CD16/32) | | 93 | Biolegend, 101319 | FC |
| Mouse TCRVβ5.1/5.2 | APC | MR9-4 | Biolegend, 139505 | FC |
| LIVE/DEAD ™ Fixable Aqua Dead Cell Stain | | | Thermal fisher, L34957 | FC |
| Mouse CD45 | | 30-F11 | Biolegend, 103101 | IF |
| Mouse CD8a | | 53-6.7 | BD, 550281 | IF |
| Mouse, humanPCSK9 antibody | | | Proteintech, 55206 | WB, IF |
| Mouse LDLR antibody | | | R&D, AF2255 | WB |
| Flag antibody | | | Sigma, F1804 | IP, WB |
| c-MYC antibody | | 9E10 | Santa Cruz, SC-40 | IP, WB |
| Protein A/G plus agarose beads | | | Santa Cruz, 2003 | IP |
| Lyso-Tracker deep red | | | Thermo Fisher, L12492 | IF |

Tumor Infiltrating Lymphocyte TCR Sequencing

Tumor cells were inoculated as described above and on day 10 after inoculation they were collected for genomic DNA extraction. Genomic DNA was extracted using DNeasy Blood & Tissue Kit (Qiagen) and submitted to Adaptive Biotechnologies for mouse TCRB CDR3 survey sequencing. About 2.6 μg of initial DNA was used as input for PCR reaction. Data were analyzed using Adaptive Biotechnologies online analysis platform.

Ot-1 T Cell Culture

OT-1 CD8$^+$ T cells expressing a transgene encoding a TCR specifically recognizing SIINFEKL peptide bound to mouse H-2K$^b$ were harvested from spleens of OT-1 C57BL/6 mice. Activated OT-1 T cells were generated by incubation of 5×10$^6$ cell/ml OT-1 SIINFEKL-pulsed mouse splenocytes in vitro for 5-7 days in the presence of mouse recombinant IL2. Briefly, an OT-1 mouse spleen was harvested and homogenized using aseptic techniques. The released cells were pelleted and resuspended in 3 ml ACK buffer (0.15 M NH$_4$Cl, 1 mM KHCO$_3$, and 0.1 mM EDTA) for 2 minutes to lyse red blood cells at room temperature. The splenocytes were then pelleted, washed, and resuspended at 5×10$^6$ cells/ml in complete growth medium (RPMI1640 [Sigma-Aldrich] with 10% fetal bovine serum [Corning], 1× penicillin-streptomycin [Thermo Fisher Scientific], 1× sodium pyruvate [Thermo Fisher Scientific] and 1×2-Mercaptoethanol [Thermo Fisher Scientific]) containing 0.75 μg/ml SIINFEKL peptide (GenScript), and incubated at 37° C. in a 95% air/5% CO$_2$ humidified environment. Mouse recombinant IL2 (Thermo Fisher Scientific) was added on days 3 and 5 at 30 Units/ml with fresh complete growth medium. On day 7, the cells were harvested for assays. The specificity was determined by flow cytometry analysis using APC/Fire750-labeled anti-mouse CD8 and APC-labeled anti-mouse TCRVβ5.1/5.2 antibodies (BioLegend).

Western Blot

Cells were washed with PBS, then lysed in RIPA buffer supplemented with protease inhibitors. Equal amounts of protein was separated by SDS-PAGE and transferred to PVDF membrane. Proteins were probed with specific antibodies followed by secondary antibodies conjugated with HRP. The HRP signal was developed by use of ECL. Quantification of interested protein was analyzed by use of Image J (NIH).

Cell Fractionation

To investigate the distribution of MHC-I in lysosome and membrane, 5×10$^7$ H2-K1-Flag transduced PCSK9 overexpressing or knockout B16F10 cells were used to isolate lysosome and membrane fractions. For lysosome isolation, a density gradient ultracentrifugation method was used following manufacturer's instructions (Lysosome Enrichment kit, Thermo Scientific). The membrane fraction was separated by use of membrane separation buffer A (50 mM Tris-HCl, pH 7.5, 450 mM NaCl, 1.5 mM MgCl$_2$, 0.2 mM EDTA, 0.1 mM EGTA, 1 mM DTT) and buffer B (buffer A plus 1% NP40, 0.1% SDS). MHC-I expression in lysosome and membrane fraction was detected by western blot by use of a mouse anti-Flag antibody. Mouse anti-LAMP2 (Porteintech) and rabbit anti-pan-cadherin (Novus Biologicals) were used as makers of lysosome and membrane, respectively.

Tumor Cell and OT-1 T Cell Co-Culture Analysis

B16F10 Ctrl-Td (expressing TdTomato fluorescent protein), B16F10 PCSK9KO-Td, B16F10 Ctrl-OVA-Td (expressing the chicken ovalbumin gene), and B16F10 PCSK9 KO-OVATd cells were first stimulated by incubation with mouse recombinant IFNγ at 1 ng/ml for 12 hours. The stimulated tumor cells were then cultured with OT-1 T cells at 1:1 ratio or without OT-1 T cells in OT-1 T cell complete growth medium with mouse recombinant IL2 (30 Units/ml) for 24 hours. Subsequently, TdTomato fluorescence and bright field images (3 field for each well) were captured by Zeiss Axio Observer. Z1 fluorescence microscope imaging station, and analyzed by ZEN imaging software (Carl Zeiss Microscopy GmbH) and ImageJ 1.52 h (NIH) for counting TdTomato-expressing tumor cells. Two-way ANOVA and Holm-Sidak's multiple comparison tests were used to examine the statistical significance. Results were plotted by use of the GraphPad Prism 6.0 software (GraphPad Software).

Immunofluorescence and Immunohistochemistry Analysis

For immunofluorescence analysis, tumors from mice were fixed in 10% neutral-buffered formalin, embedded into paraffin, sectioned and then mounted onto slices. They were then stained according to standard procedures by use of antibodies against mouse CD45 or CD8a listed in Table 2.

For lysosome co-localization experiments, cells were incubated with Lyso-Tracker (deep red, Thermo Fisher Scientific) at 37° C. for 20 min, fixed with 4% paraformaldehyde at room temperature for 15 min, and permeated with blocking buffer (1% BSA, 5% Donkey serum, 0.1% digitonin) at room temperature for 30 min. The cells were then incubated with anti-Flag (Sigma, F1804) and anti-PCSK9 (Proteintech, 55206-1-AP) primary antibodies for 1 hour at room temperature. After washing with PBS, the stained slices were mounted with mounting medium (Vector Laboratories) containing DAPI. Images were captured by use of confocal microscopy.

Generation of Ectopic Gene Expression Constructs

PCR primers with sequences listed in Table 3 were used to obtain a 2.2 kb fragment of mouse PCSK9 with myc tag and a 0.7 kb fragment of H2K$^d$ with flag tag. DNA fragment encoding PCSK9-myc and H2K$^d$-Flag fragment were then cloned into GFP-Neo lentiviral vector by use of the Gibson assembly's kit following manufacturer's instruction (New England Biolabs). Lentiviral vector encoding the genes were made and then used to infect B16F10 cells. Cells were selected with G418 for 5 days before subsequent analysis.

TABLE 3:

Primers for PCR and RT-PCR

| | |
|---|---|
| mouse PCSK9-myc tag forward primer | 5'-cctccatagaagacaccgacTctagag gatccgccaccatgggcacccactgctctg c-3' |
| mouse PCSK9-myc tag reverse primer | 5'-ttgtaatccagaggttgattgtcgact cacagatcctcttcagtgatgagtttctgt tCctgaacccaggaggcctttg-3' |
| mouse H2-Kd-Flag tag forward primer | 5'-cctccatagaagacaccgacTctagag gatccgccaccatgtggacggcggcggaca tggc-3' |
| mouse H2-Kd-Flag tag reverse primer | 5'-ttgtaatccagaggttgattgtccact cacttctcatcatcatccttctagtCcact ttacaatctgggagag-3' |
| Gzmb F | 5'-CCACTCTCGACCCTACATGG-3' |
| Gzmb R | 5'-GGCCCCCAAAGTGACATTTATT-3' |
| IFNγ F | 5'-ATGAACGCTACACACTGCATC-3' |
| IFNγ R | 5'-CCATCCTTTTGCCAGTTCCTC-3' |

Protein Co-Immunoprecipitation (CO-IP)

Cultured cells in 10-cm petri dishes were washed with ice-cold PBS twice and directly lysed with 500 µl IP lysis buffer (150 nM NaCl, 50 mM Tris, 0.1% NP-40) supplemented with protease inhibitors (Sigma-Aldrich) on ice. Cell lysates were transferred to 1.7 ml tubes and end-to-end rotated for 15 min at 4° C. Protein concentration in lysates were measured by Bio-Rad protein assay. For IP of HA tagged PCSK9 protein, 500 µl of cell lysates were incubated with 5 µl anti-HA antibody (Santa Cruz Biotechnology) on a rotator at 4° C. overnight. Then, the lysate with c-HA antibody was conjugated with 20 µl ProteinA/G agarose beads (Santa Cruz Biotechnology) for 2 hours at 4° C. After washing with IP lysis buffer three times, the pull-down complex was boiled in 2× SDS loading buffer for SDS-PAGE and western analysis.

Quantitative RT-PCR

Total RNA from CRISPR/Cas9 vector control or PCSK9 knockout B16F10 tumor cells extracted and subject to RNA-seq analysis. RNA-seq was carried out by the Duke University Sequencing and Genomic Technologies Core. The Kapa Stranded mRNA-seq library prep kit was used to make sequencing libraries. The libraries were sequenced by use of an Illumina Hiseq 4000 instrument with a 50 bp single end reads length.

RNA-seq data was processed using the TrimGaloretoolkit which employs Cutadapt to trim low-quality bases and Ilumina sequencing adapters from the 3' end of the reads. Only reads that were 20 nt or longer after trimming were kept for further analysis. Reads were mapped to the GRCm38.p6 of the mouse genome and transcriptome using the STAR RNA-seq alignment tool. Reads were kept for subsequent analysis if they mapped to a single genomic location using the SAMtools. Gene counts were compiled using the HTSeq tool. Only genes that had at least 10 reads in any given library were used in subsequent analysis. Normalization and differential expression was carried out using the DESesq2 Bioconductor package with the R statistical programming environment. Gene set enrichment analysis (GSEA) was performed to identify differentially regulated pathways and gene ontology terms for the comparisons performed.

Total RNA was extracted from CRISPR/Cas9 control or PCSK9 knockout B16F10 tumors (around 200-300 mm$^3$ in volume) from tumor-bearing C57BL/6J mice by use of RNeasy Mini Kit (Qiagen) according to the manufacturer's instructions. RNA was subjected to cDNA synthesis with random hexamer primers using Superscript II reverse transcriptase (Invitrogen). Quantitative real-time PCR (qRT-PCR) was performed using QuantiTest SYBR Green PCR Master Mix Kit (Qiagen). Primers used for different genes were listed in Table 3.

Cycloheximide Chase Assay

To determine PCSK9's influence of lysosomal degradation of the MHC-I Protein, vector control or PCSK9 knockout MDA-MB-231 cells were treated with 20 µg/ml cycloheximide (CHX, Sigma) to inhibit protein biosynthesis for 1, 4, 8, 18, 24 hours. For lysosome inhibition, MDA-MB-231 cells were treated with 20 nM Bafilomycin (Baf A1, Sigma) for 1, 2, 4, 8, 24 hours. The cells were then harvested and MHC class I proteins were detected by western blot by use of anti-HLA-ABC antibody (Proteintech).

Statistical Analysis

Statistical analysis was performed using GraphPad Prism 6 software and statistical significance was determined by p value less than 0.05. Two-way ANOVA was used for multiple comparisons in tumor growth delay experiments. Log-rank (Mantel-Cox) test was used for mouse survival analysis. In other experiments, comparisons between two groups were conducted by use of unpaired Student's t test. The Gene Expression across Normal and Tumor tissue database (GENT) was used to analyze the relationship between PCSK9 and CD8A in indicated patient cohorts. Data on PCSK9 gene expression and patient survival were obtained from TCGA database and its relationship was evaluated using log-rank test and a value of $p<0.05$ was considered statistically significant.

Results

Referring now to FIGS. 4A-4H, when the PCSK9-deficient cells were inoculated into syngeneic mouse hosts, however, their abilities to form tumors were significantly attenuated (FIGS. 4A, 4C, 4E, 4G). In addition, in all four murine tumor lines tested, there were long-term survivors where host mice remained tumor free up to 60 days post tumor cell inoculation in the PCSK9 knockout group. In contrast, in groups where mice were injected with vector control-transduced tumor cells, all mice had to be sacrificed eventually because of tumor growth (FIGS. 4B, 4D, 4F, 4H). Preferential growth suppression of PCSK9-deficient cells were further confirmed in vivo by use of fluorescent proteins. It is clear that PCSK9 knockout cells were almost completely lost while control cells remained in the tumor mass in large numbers. About $1\times10^5$ vector control and PCSK9 knockout murine tumor cells were inoculated subcutaneously into sygeneic mice and observed for tumor formation. Both tumor size and tumor free survival were monitored. "TF" indicates that those particular experiments resulted in the indicated number of tumor free mice.

Figure 5A:
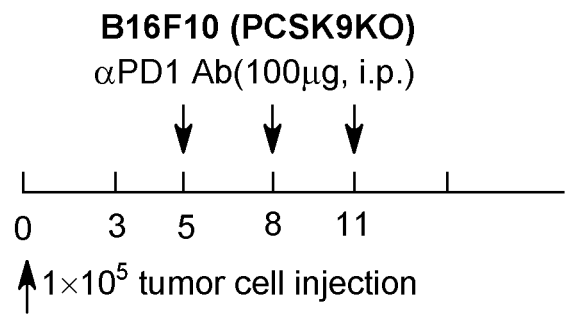
FIGS. 5A-5K are images and graphs showing PCSK9 inhibition overcomes tumor resistance to anti-PD1 therapy.
Figure 5B:
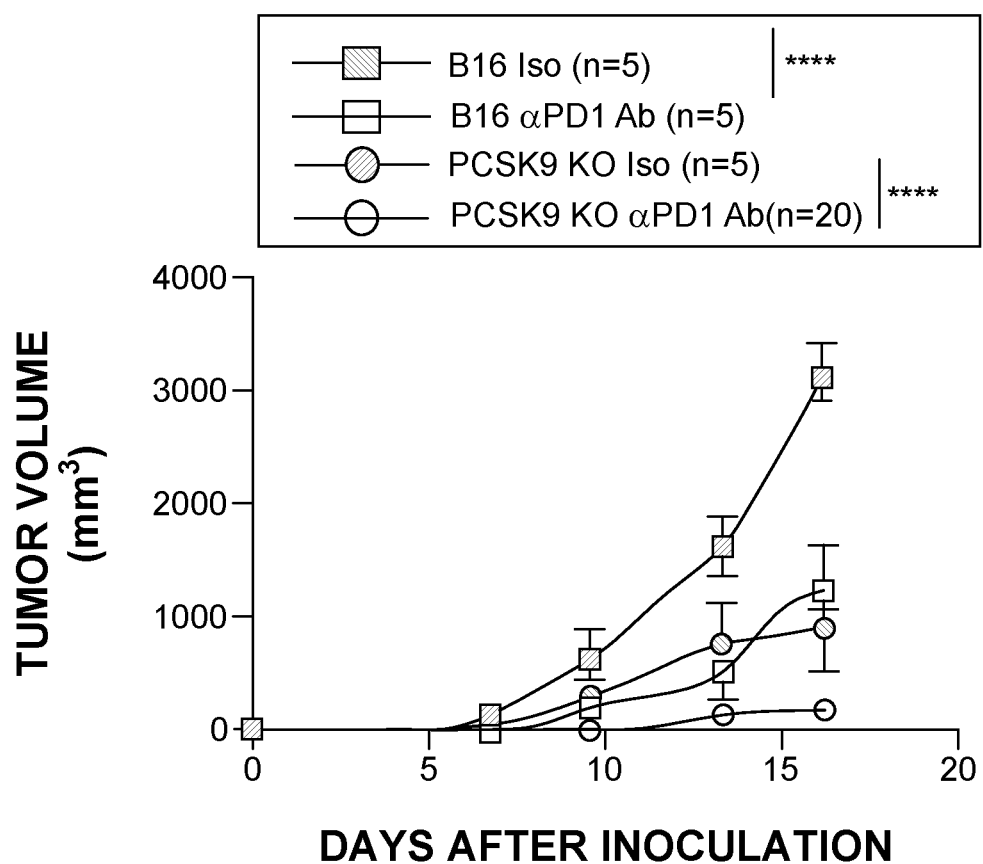
Figure 5C:
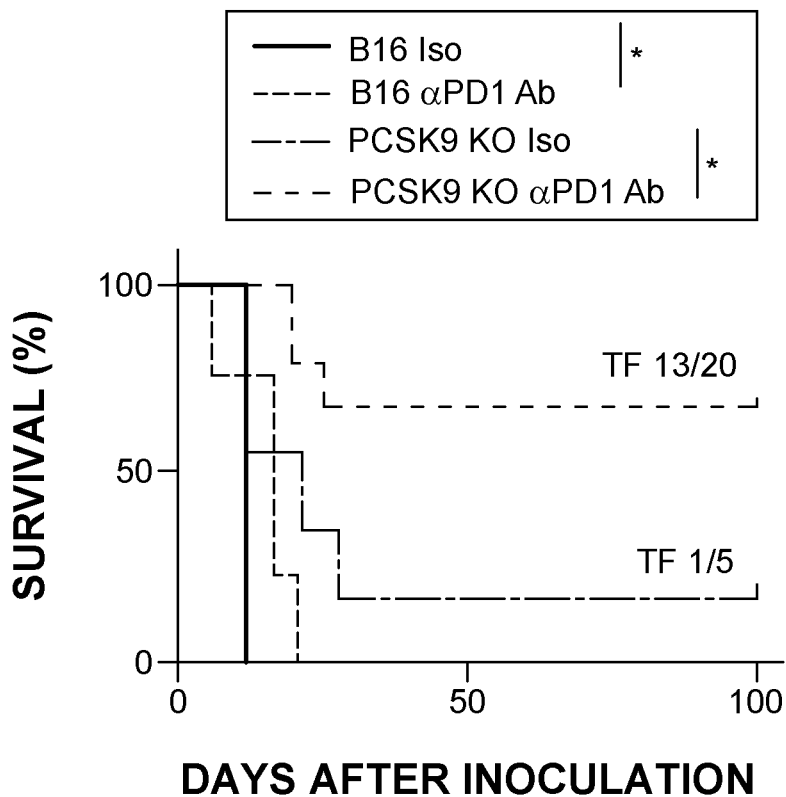
Figure 5D:
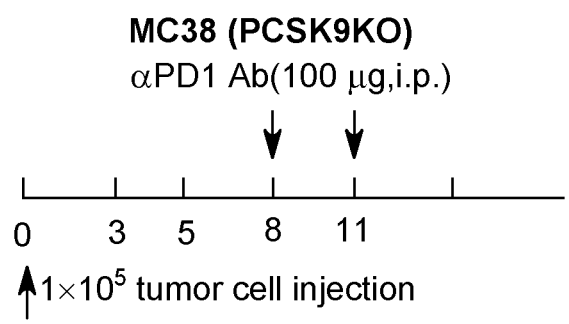
Figure 5E:
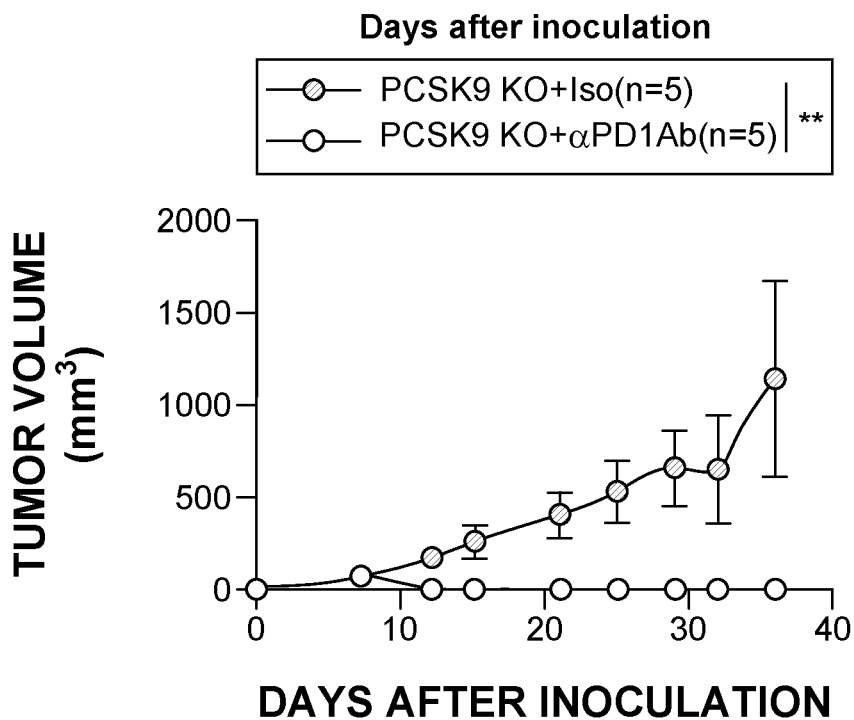
Figure 5F:
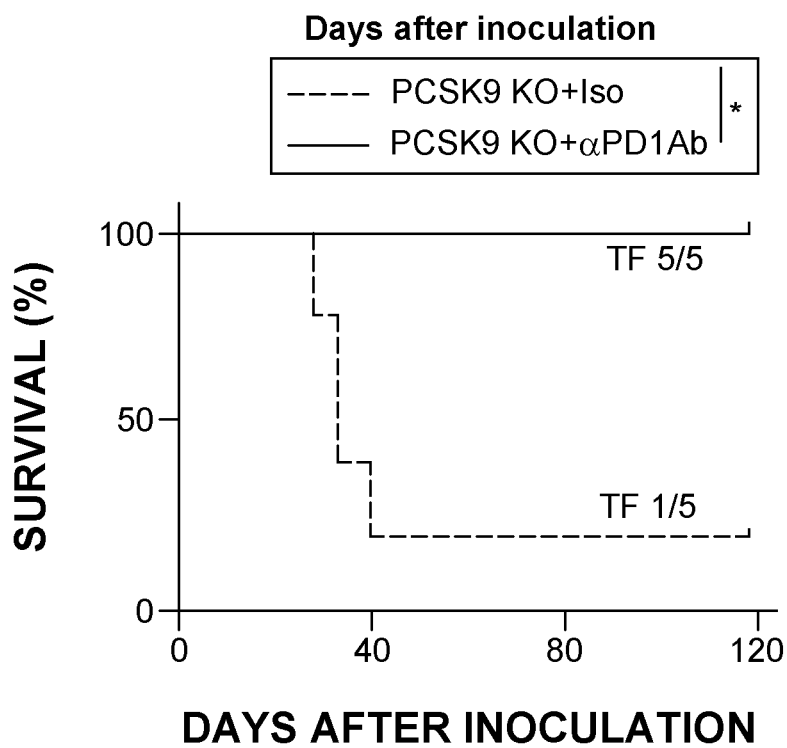
Figure 5G:
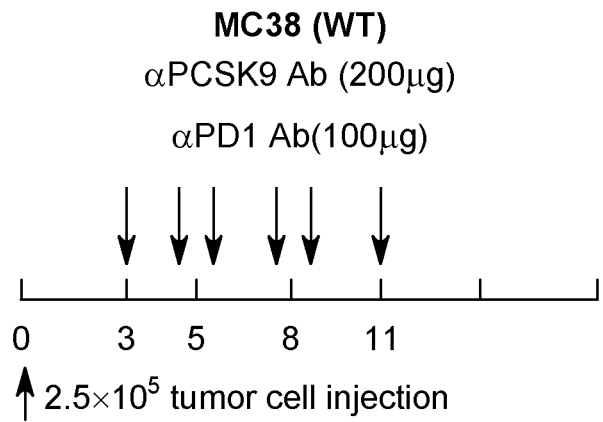
Figure 5H:
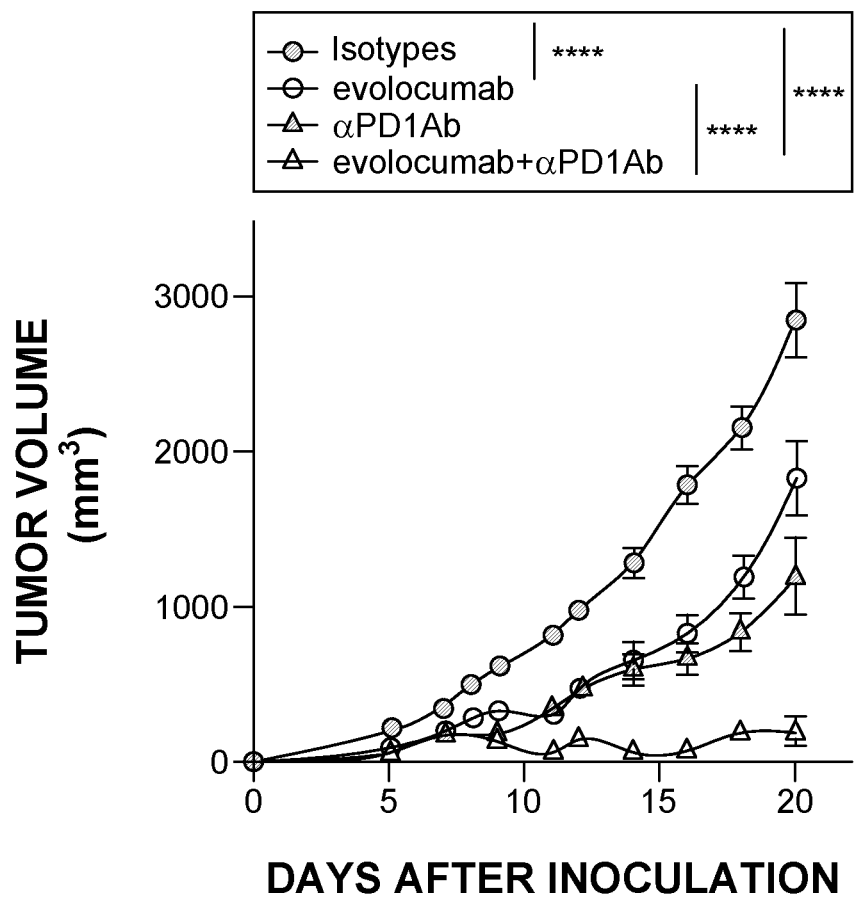
Figure 5I:
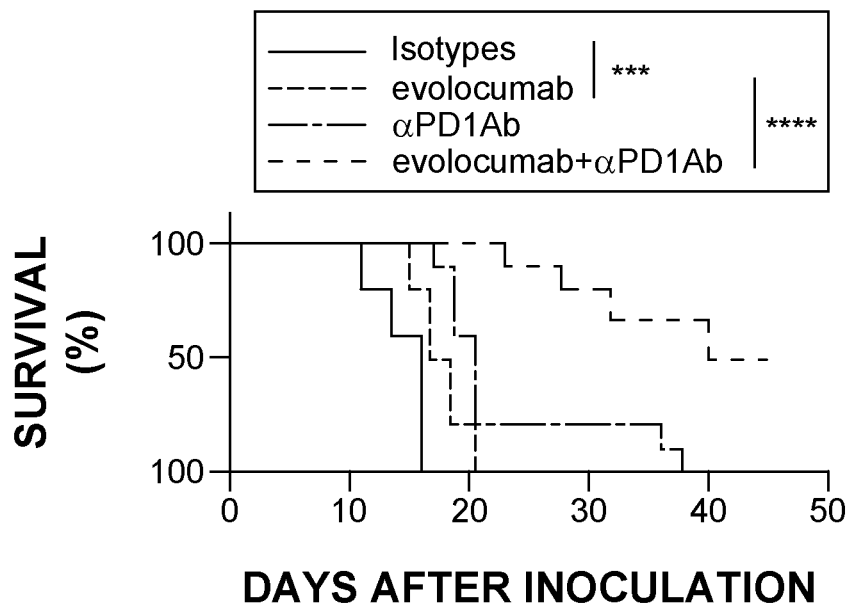
Figure 5J:
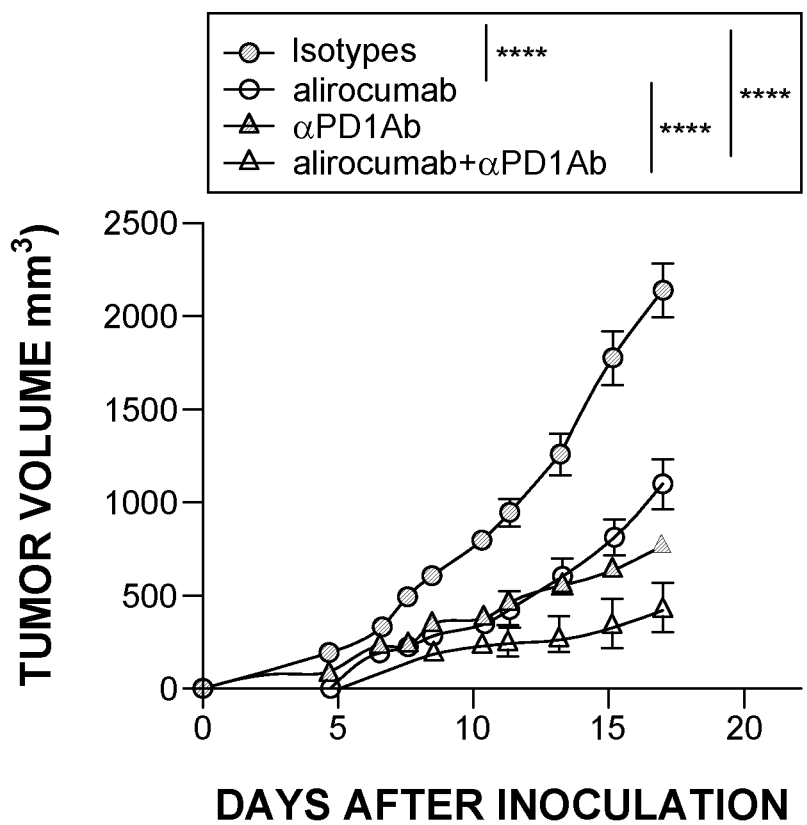
Figure 5K:
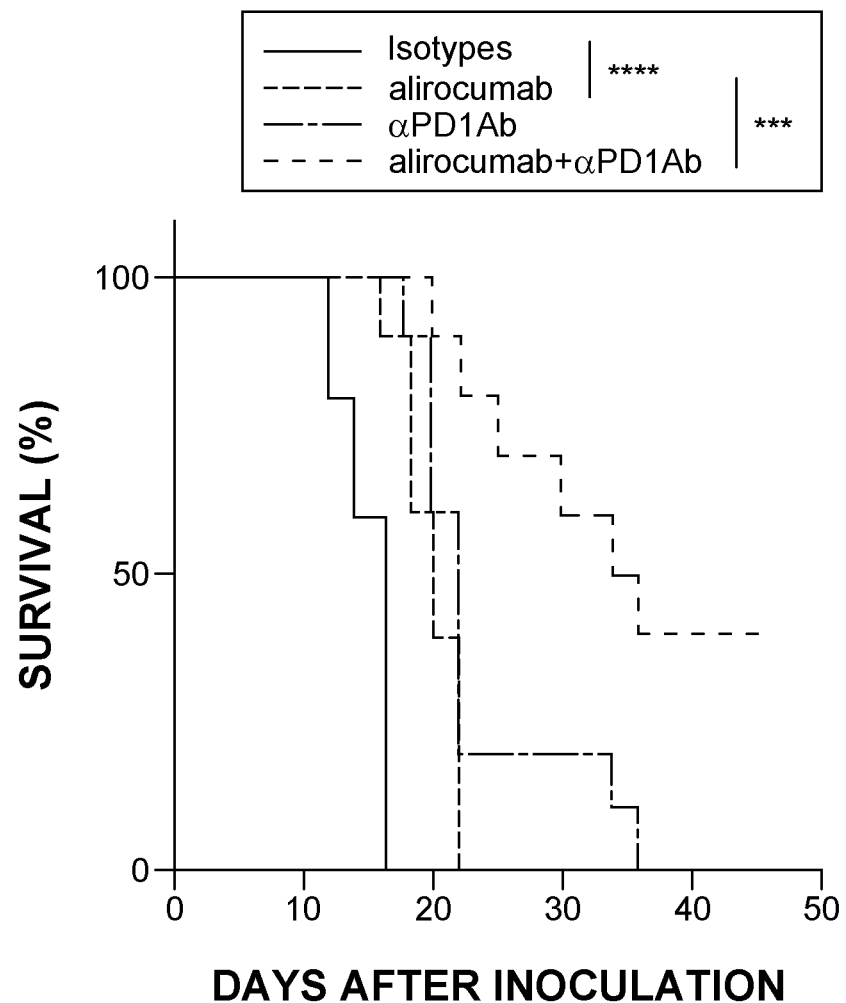

Referring now to FIGS. 5A-5K, in order to further evaluate the roles of the immune system in mediating PCSK9-deficiency induced growth suppression, experiments were carried out with an anti-PD1 immune checkpoint inhibitor in mice inoculated with PCSK-deficient B16F10 melanoma, MC38 colon cancer, and CT26 colon cancer models. The results indicate that anti-PD1 antibody administration synergized with PCSK9 deficiency in all three tumor models in suppressing tumor growth. In fact, the majority of PCSK9 deficient tumor cell inoculated mice remained tumor free 80-100 days after treatment with the anti-PD1 antibody. FIGS. 5A-5C depict results from treatment of PCSK9 knockout B16F10 melanoma with an anti-PD1 antibody in sygeneic mice. An isotype control antibody was used to control for the anti-PD1 antibody. FIGS. 5D-F depict results from treatment of PCSK9 knockout MC38 colon cancer with an anti-PD1 antibody mice. FIGS. 5G-5K depict results from treatment of wild type MC38 colon cancer with combined anti-PCSK9 and anti-PD1 antibodies in mice. While administration of the anit-PD1 or anti-PCSK9 antibodies alone could cause significant growth delay in MC38 tumors, their efficacies were significantly enhanced by the addition of an anti-PD1 antibody. 5 of 10 or 4 of 10 MC38 mice treated with evolocumab+anti-PD1 or alirocumab+anti-PD1, respectively, remained tumor free for up to 60 days post inoculation, indicating long-term cure. The results suggest that PCSK9 inhibition could effectively overcome resistance to anti-PD1 immune checkpoint therapy in various murine tumor models.

Figure 6A:
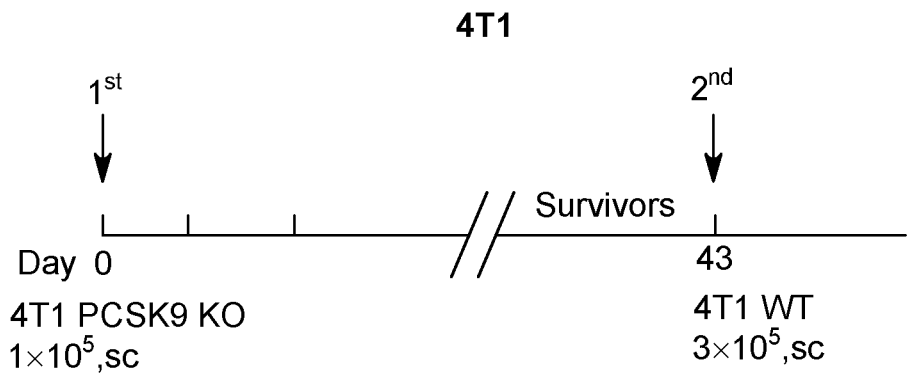
FIGS. 6A-6I are images and graphs showing tumor growth after re-challenge in mice that were cured of their initial tumor inoculation.
Figure 6B:
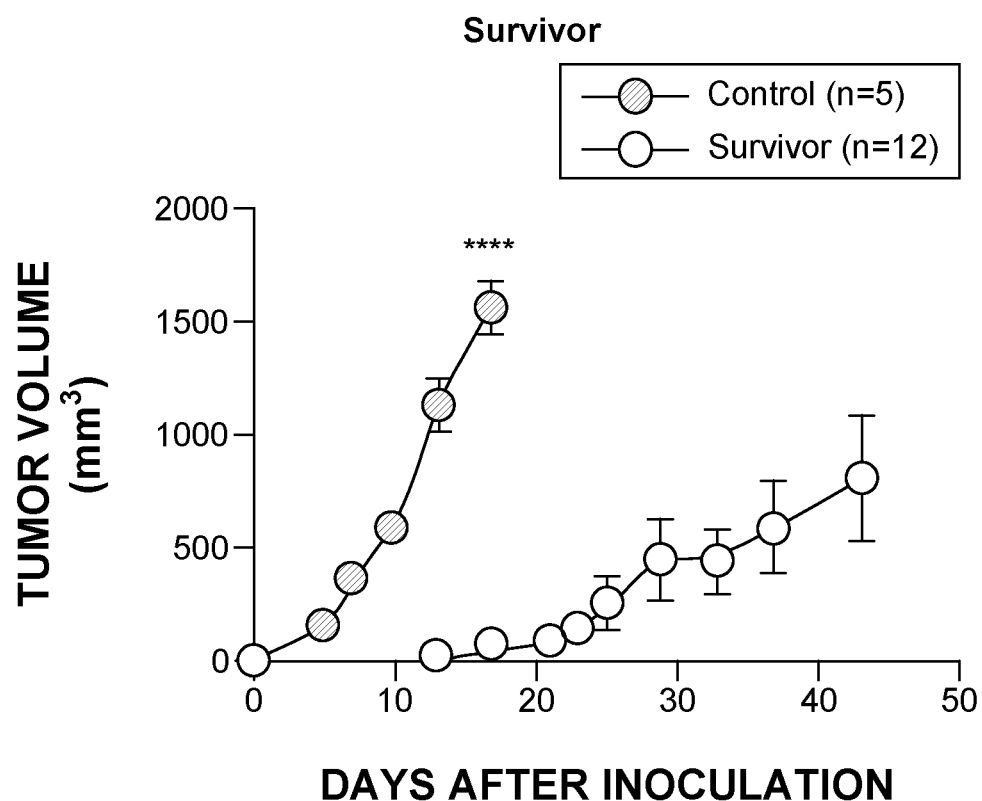
Figure 6C:
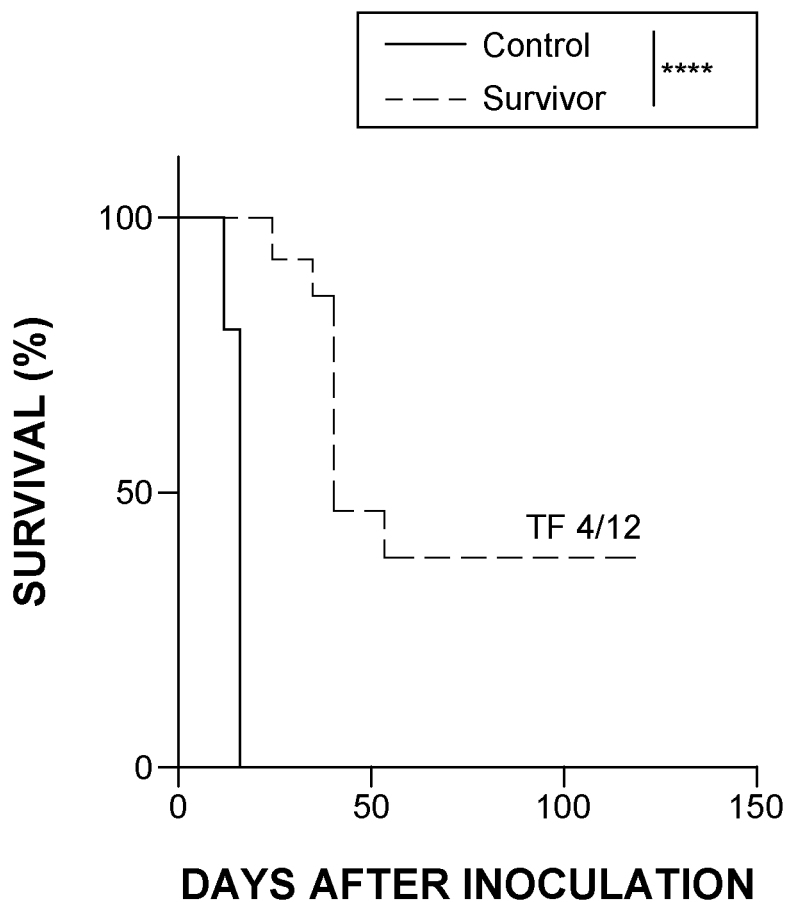
Figure 6D:
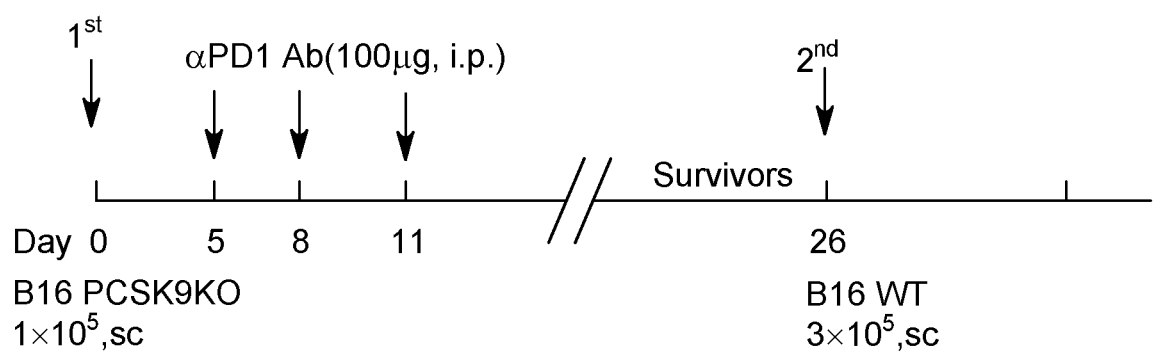
Figure 6E:
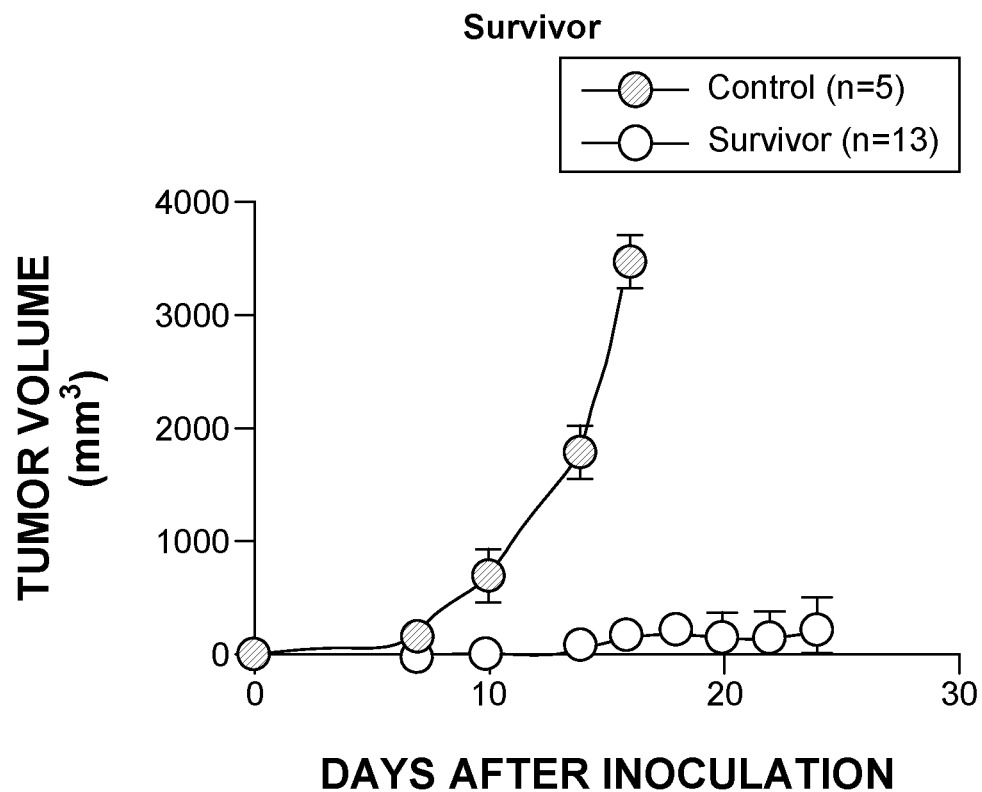
Figure 6F:
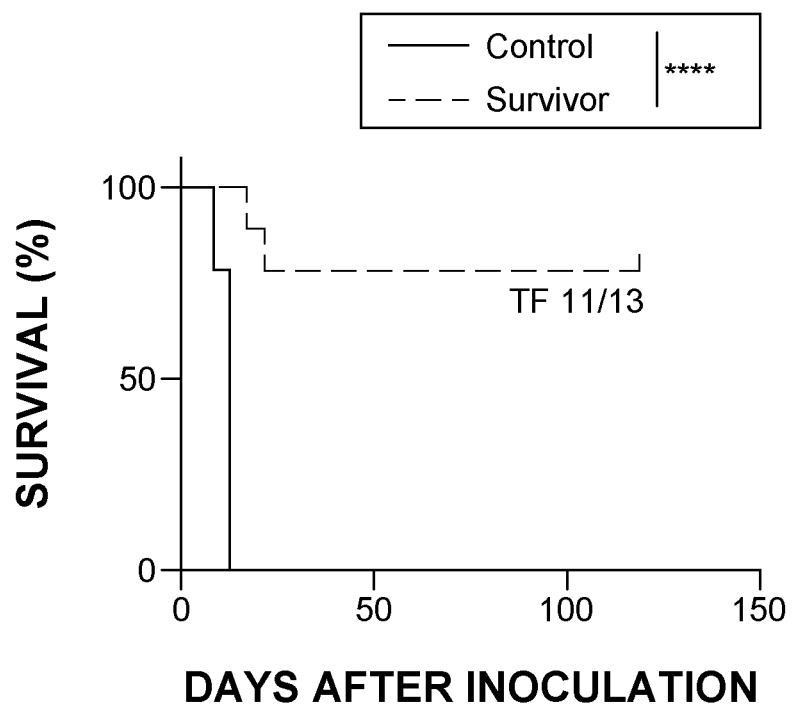
Figure 6G:
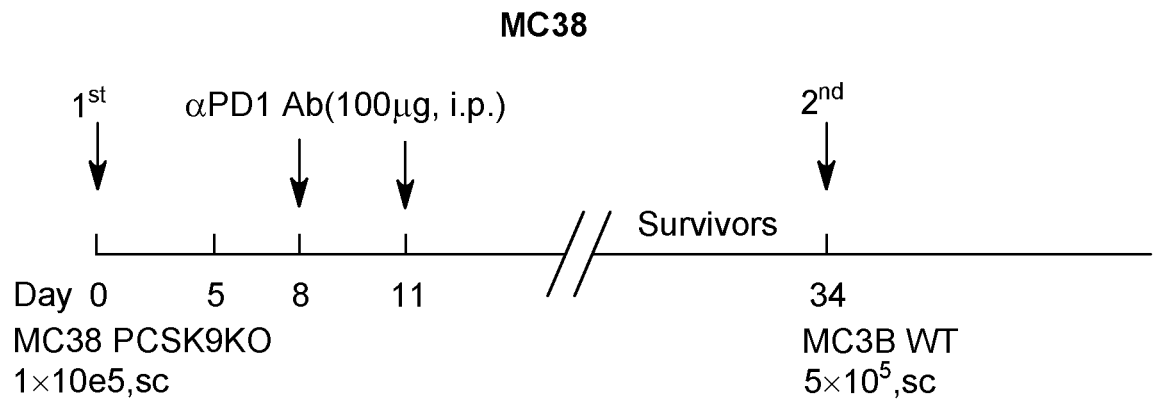
Figure 6H:
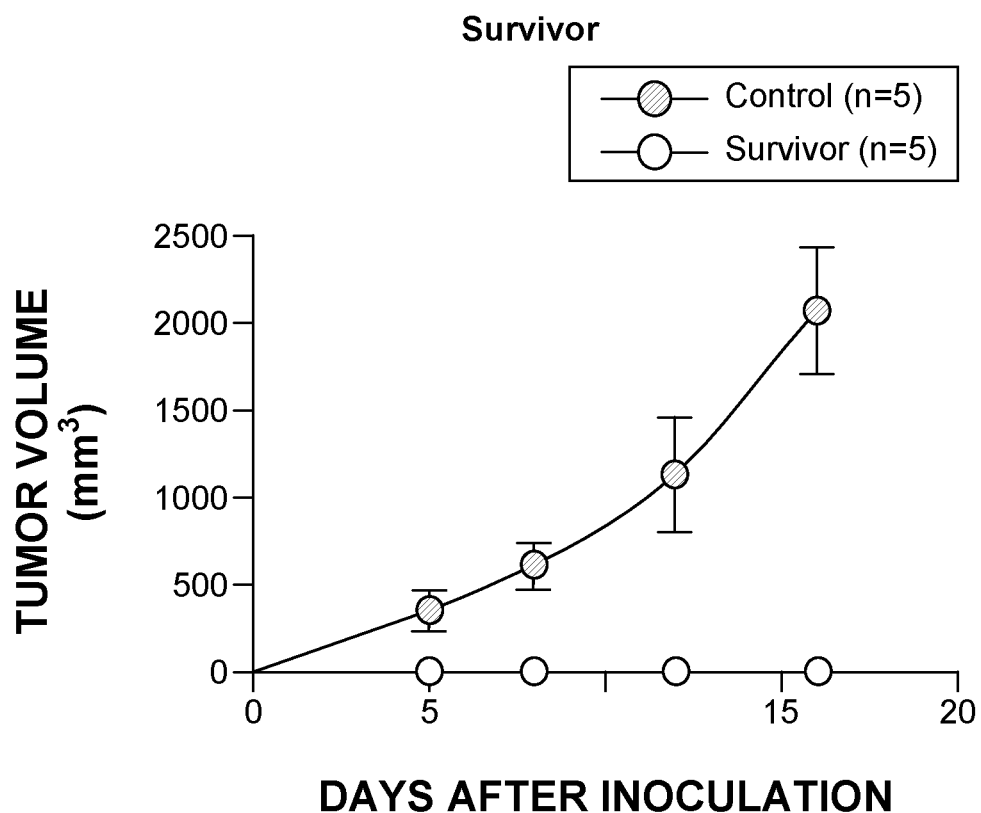
Figure 6I:
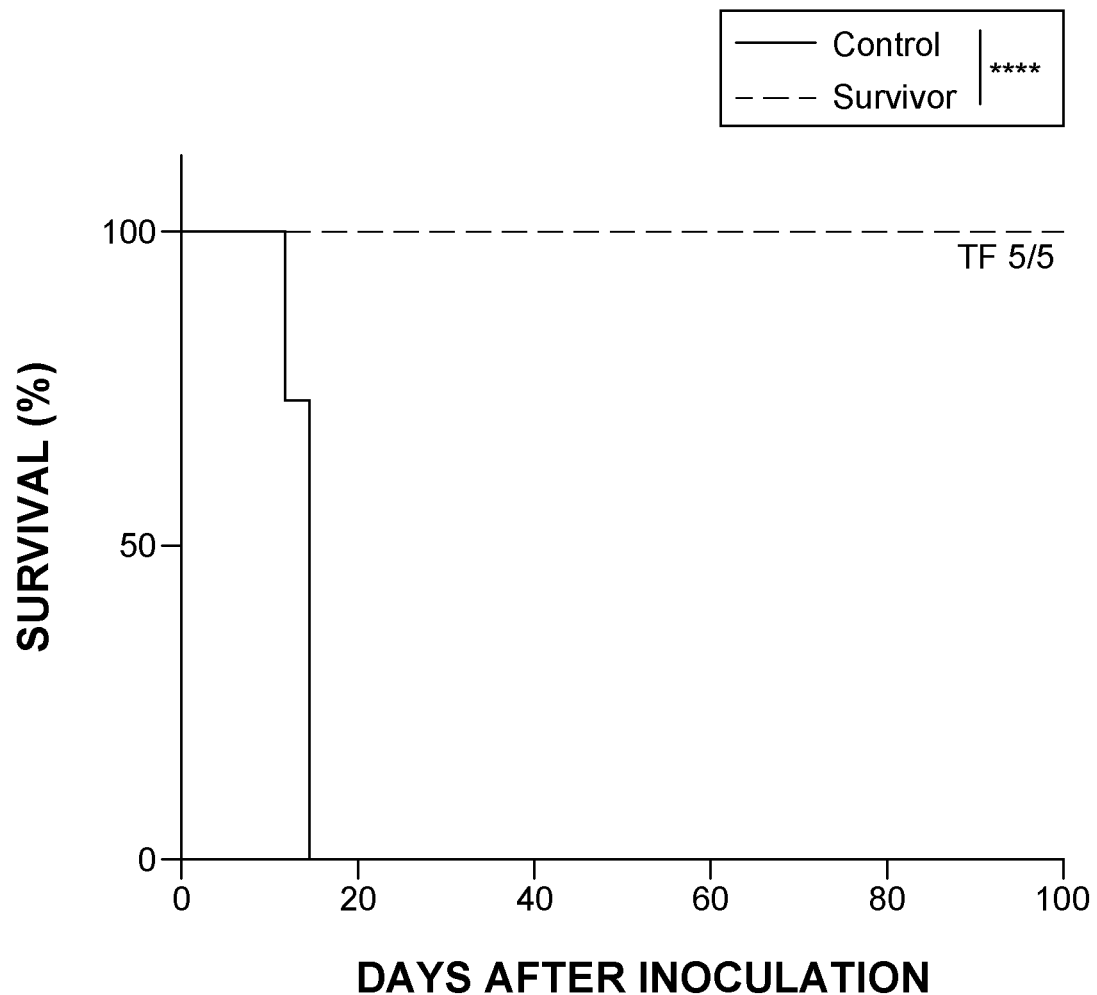

Referring now to FIGS. 6A-6I, the ability of the mice that remain tumor-free long term (>30 days) after initial tumor cell inoculation to resist re-challenge was evaluated. Wild type tumor cells were injected into those mice that remain tumor free after the initial challenge. The results indicate that 11/13 of B16F10 (PCSK9-deficiency+PD1Ab treated), and 4 of 12 4T1 (PCSK-deficiency alone) inoculated and tumor-free mice were refractory to re-challenge with wild type parental tumor cells. The data indicates that PCSK9 inhibition combined with anti-PD1 antibody could elicit long-term anti-tumor memory in mice. FIGS. 6A-6C show tumor growth rates and survival of host mice after re-challenge with wild-type 4T1 tumor cells in Balb/C mice that remained tumor free 43 days after initial inoculation with PCSK9 deficient 4T1 cells. FIGS. 6D-6F show tumor growth rates and survival of host mice after re-challenge with wild-type B16F10 tumor cells in C57BL/6 mice that remained tumor free 26 days after initial inoculation with PCSK9 deficient B16F10 cells and treatment with anti-PD1 antibody. FIGS. 6G-6H show tumor growth rates and survival of host mice after re-challenge with wild-type MC38 tumor cells in C57BL/6 mice that remained tumor free 34 days after initial inoculation with PCSK9-deficient MC38 cells and treatment with anti-PD1 antibody.

Figure 7A:
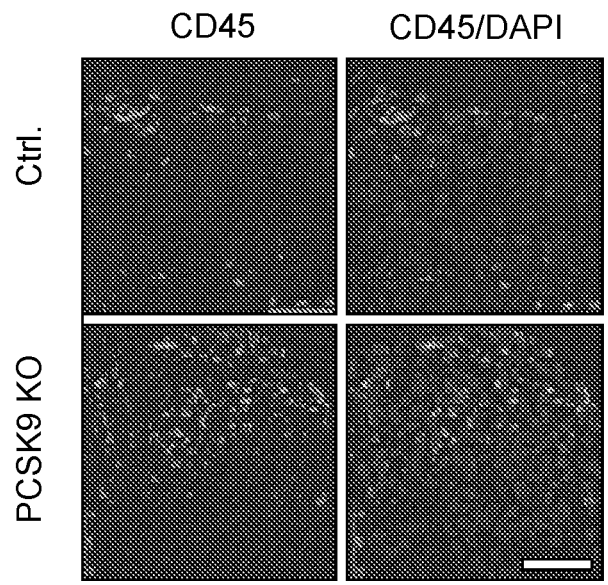
FIGS. 7A-7E are images and graphs showing immunofluorescence staining of overall lymphocyte infiltration into B16F10 tumors.
Figure 7B:
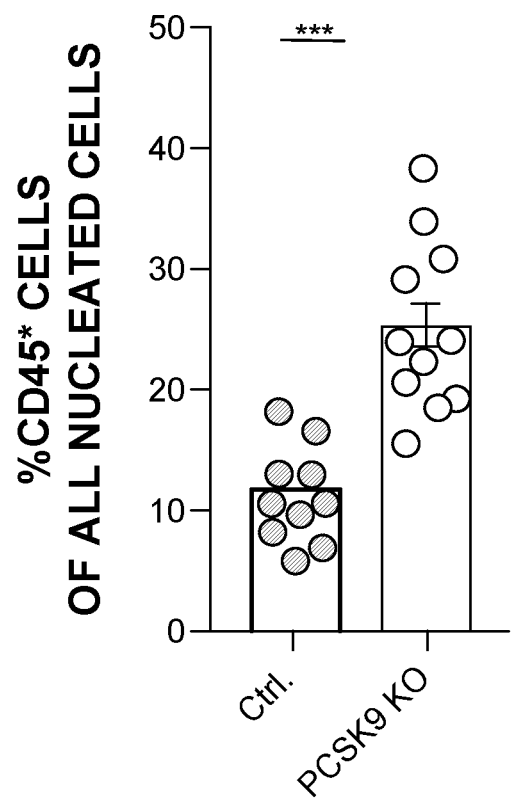
Figure 7C:
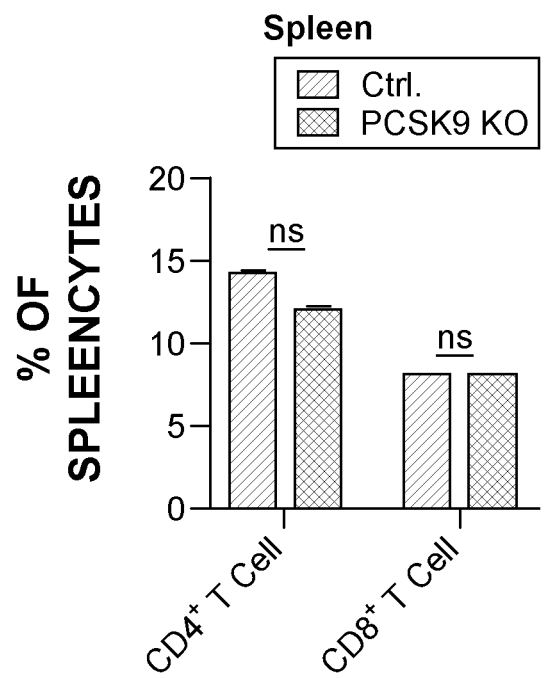
Figure 7D:
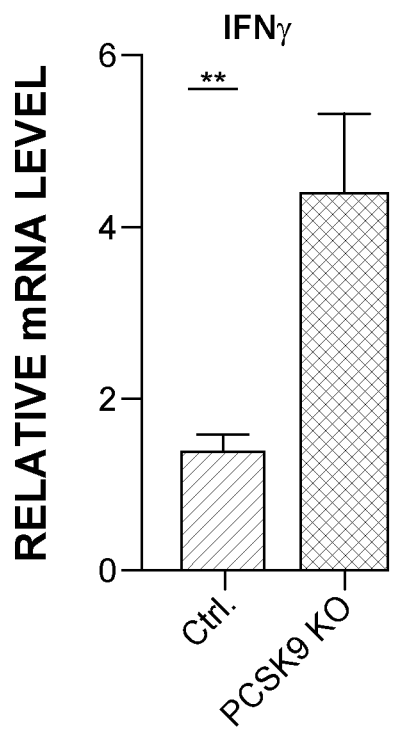
Figure 7E:
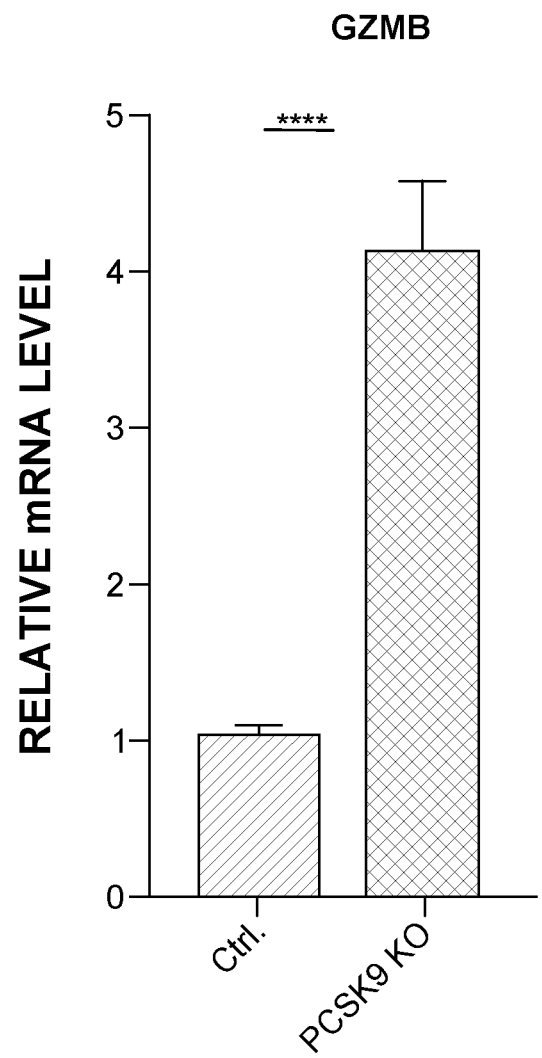

Referring now to FIGS. 7A-7E and 8A-8F, immune cell infiltration into the tumors was analyzed to understand the positive effect of PCSK9 inhibition on anti-tumor immunity. FIG. 7A shows immunofluorescence staining of CD45 positive lymphocytes in control and PCSK9 KO tumors grown in syngeneic C57BL/6J mouse. FIG. 7B shows quantitative estimates of CD45 positive lymphocytes in control and PCSK9 KO tumors. FIG. 7C shows quantitative estimates of CD4+ and CD8+ T cells in the spleens of mice bearing control and PCSK9 KO tumors. FIGS. 7D and 7E shows quantitative reverse transcribed PCR (Q-RTPCR) analysis of intratumoral IFNγ and Granzyme B mRNA levels in control and PCSK9 KO tumors.

Figure 8A:
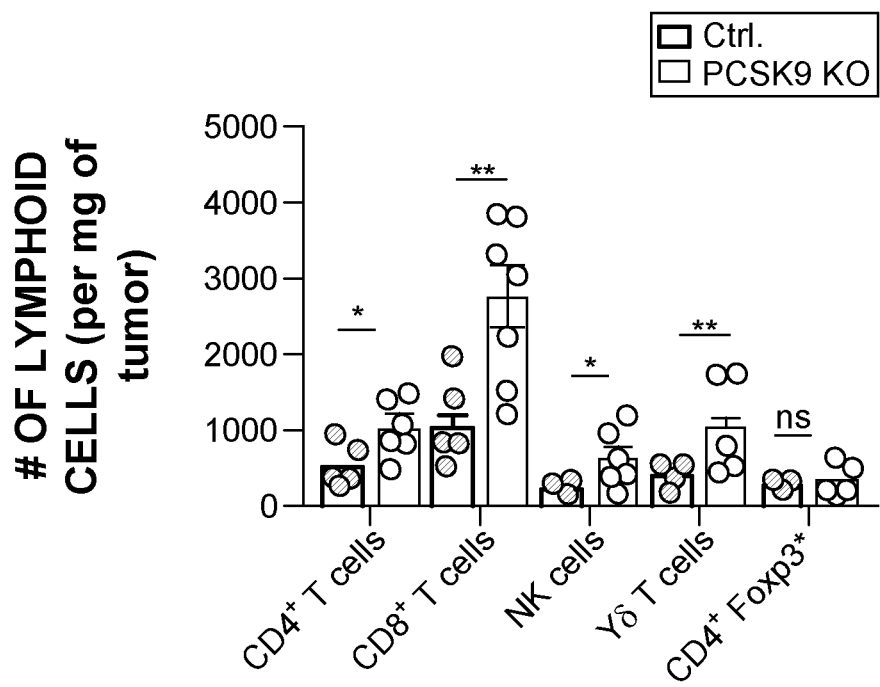
FIGS. 8A-8O.II are images and graphs showing PCSK9 depletion enhances intratumoral T-cell infiltration and CTL activities.
Figure 8B:
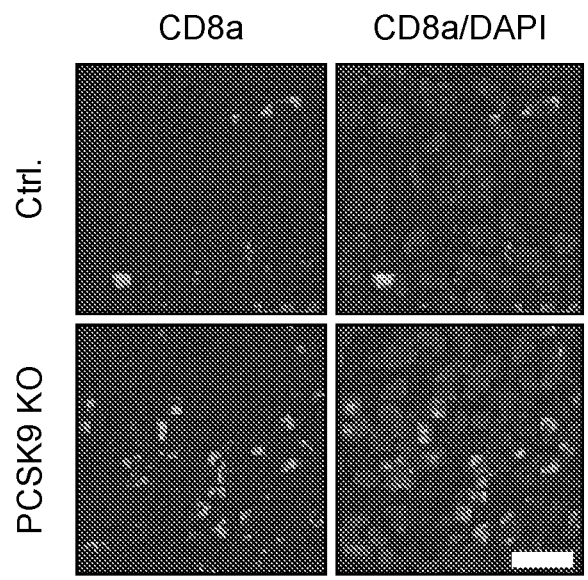
Figure 8C:
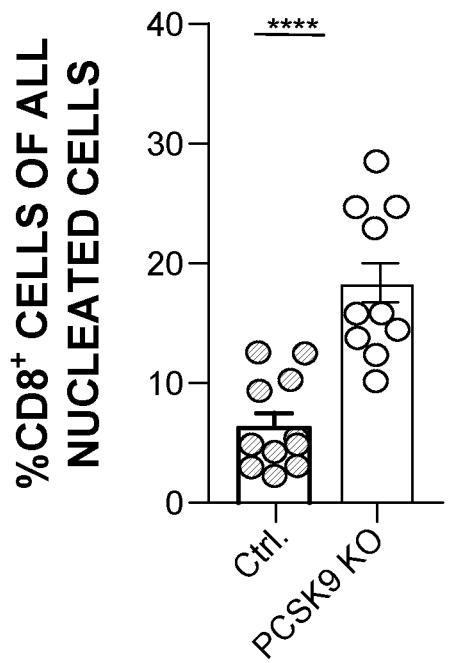
Figure 8D:
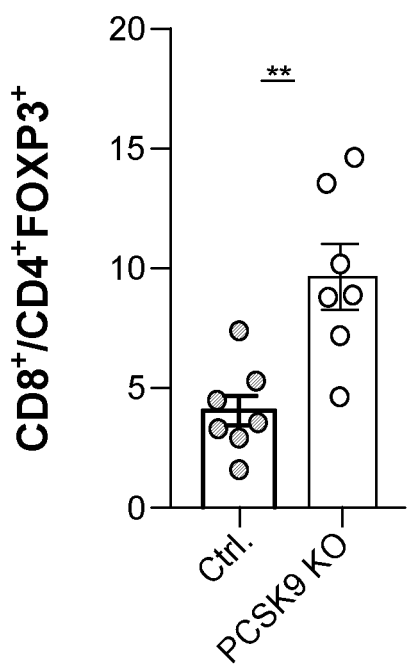
Figure 8E:
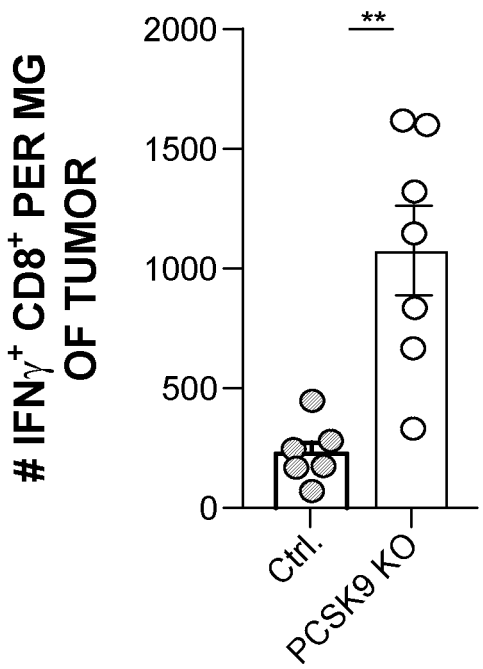
Figure 8F:
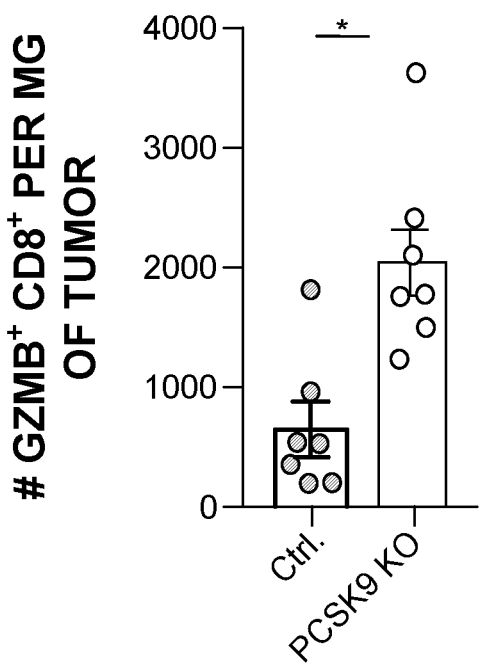

The data indicates that PCSK9 depletion caused an overall increase in lymphocyte infiltration intratumorally, as identified by the fraction of $CD45^+$ cells. In addition, significant increases in intra-tumoral $CD4^+$ T helper ($T_h$) cells, $CD8^+$ cytotoxic T-cells, and NK cells were also observed (FIG. 8A). In contrast, no increase in $CD4^+Foxp3^+$ Treg cells was observed intratumorally (FIG. 8A). Furthermore, no increase in $CD4^+$ or $CD8^+$ T-cells were observed in the spleen of host mice (FIG. 7C). Immunofluorescence staining further confirmed the increase in $CD8^+$ cytotoxic T-cell infiltration into the tumors (FIGS. 8B, 8C). Of particular interest was the observation that CTLs moved within tumor cell-rich areas in the PCSK9-deficient B16F10 tumors (FIG. 8B). In comparison, CTLs stayed mostly in the periphery in control B16F10 tumors (FIG. 8B). Further analysis showed that the ratios of $CD8^+$ CTL vs Treg cells in the tumor were significantly increased (FIG. 8D). Similarly, the numbers of $IFN\gamma^+$ and Granzyme B+ CTLs also increased significantly in PCSK9-deficient tumors when evaluated either by flow cytometry (FIGS. 3E, 3F) or Q-RT-PCR (FIGS. 7D, 7E), consistent with increased CTL activities in the tumors.

Figure 8G:
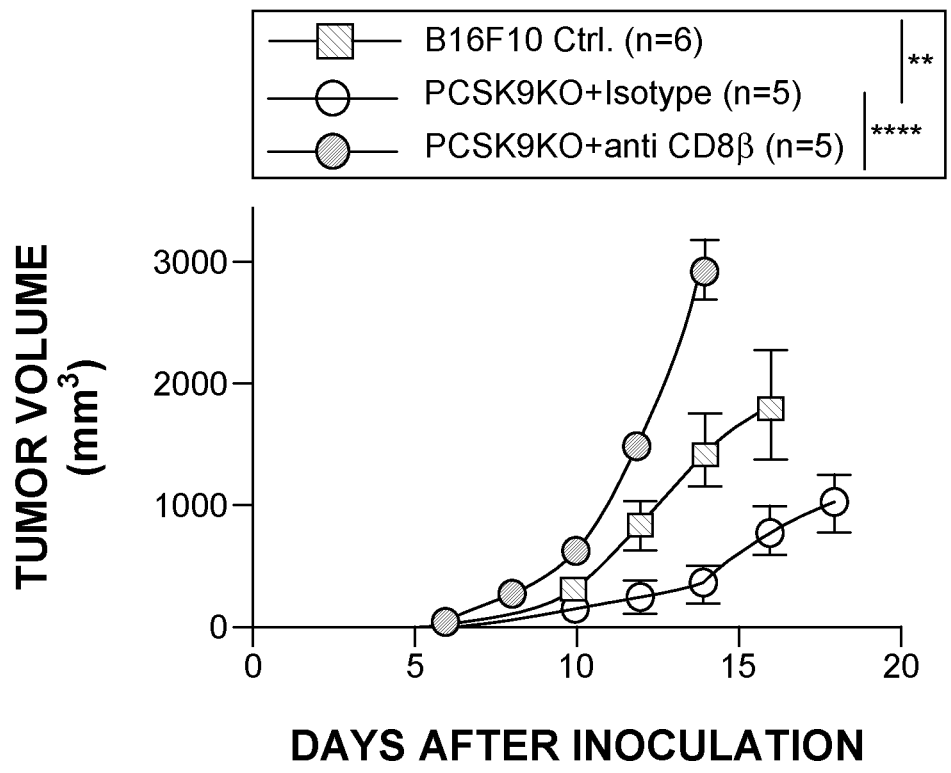
Figure 8H:
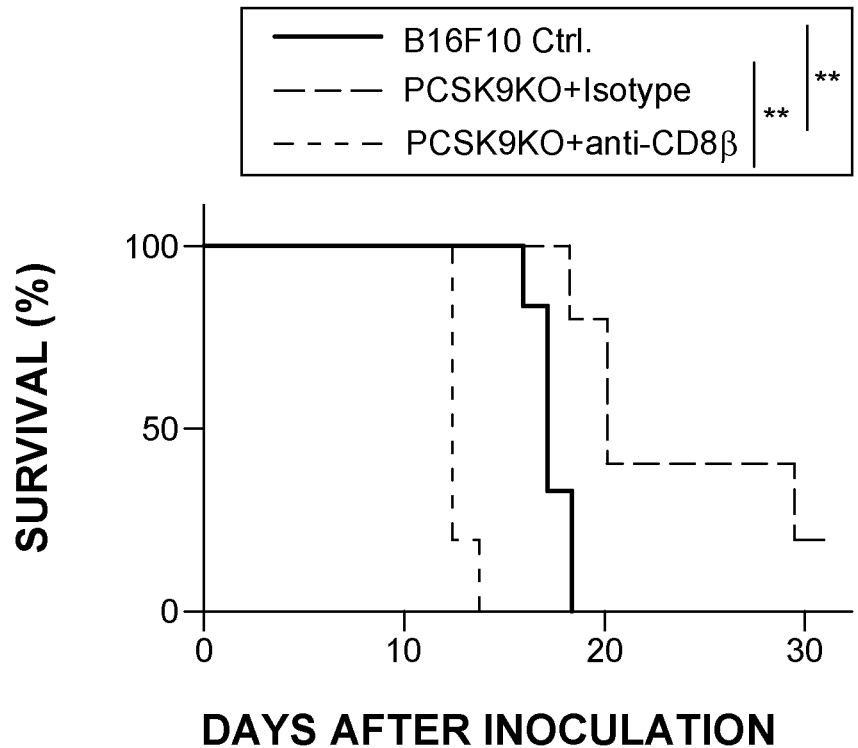

Referring now to FIGS. 8G-8H and FIGS. 9A-E, an anti-body based approach to deplete $CD4^+$ T cells, $CD8^+$ T cells, and NK cells was used to determine the relative importance of those cellular components on PCSK9-deficient tumor growth. The data indicates that depletion of $CD8^+$ cells (following the schedule shown in FIG. 9A) completely abolished the tumor growth delay observed in PCSK9-deficient tumors (FIGS. 8G, 8H). In contrast, depletion of $CD4^+$ T cells or NK cells had minimal effect on growth delay in PCSK9 deficient tumors (FIGS. 9B-9E).

Figure 8I:
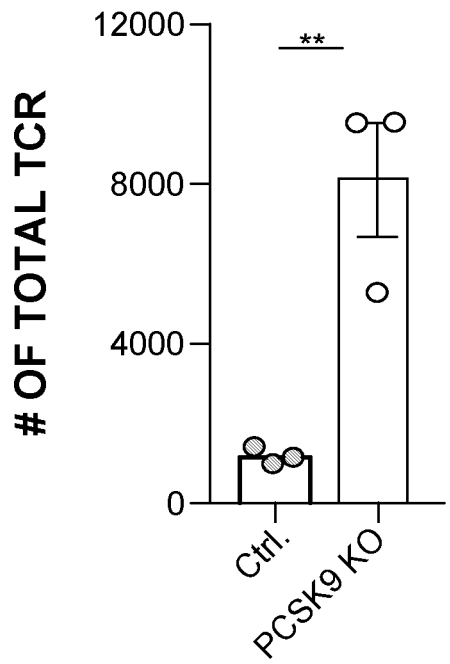
Figure 8J:
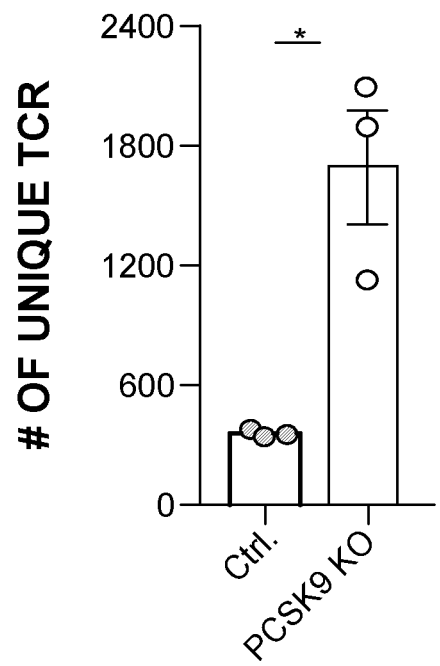
Figure 8K:
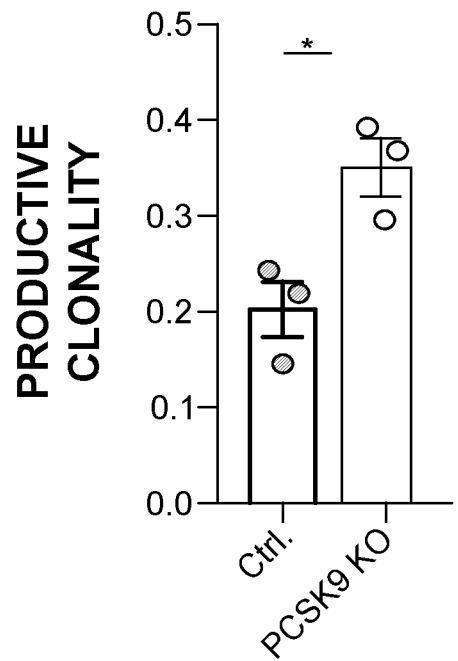
Figure 8L:
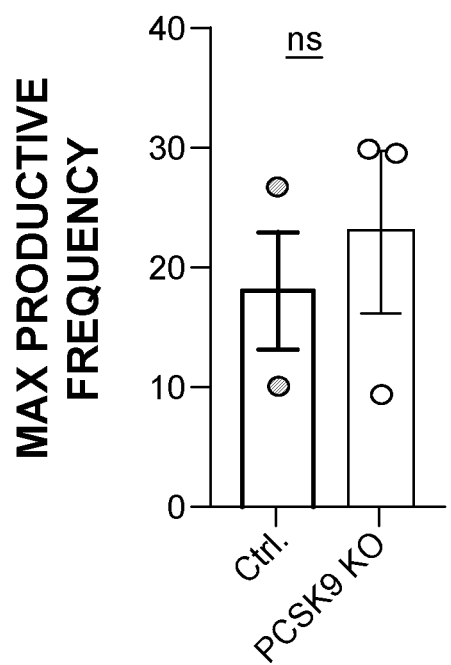
Figure 8M:
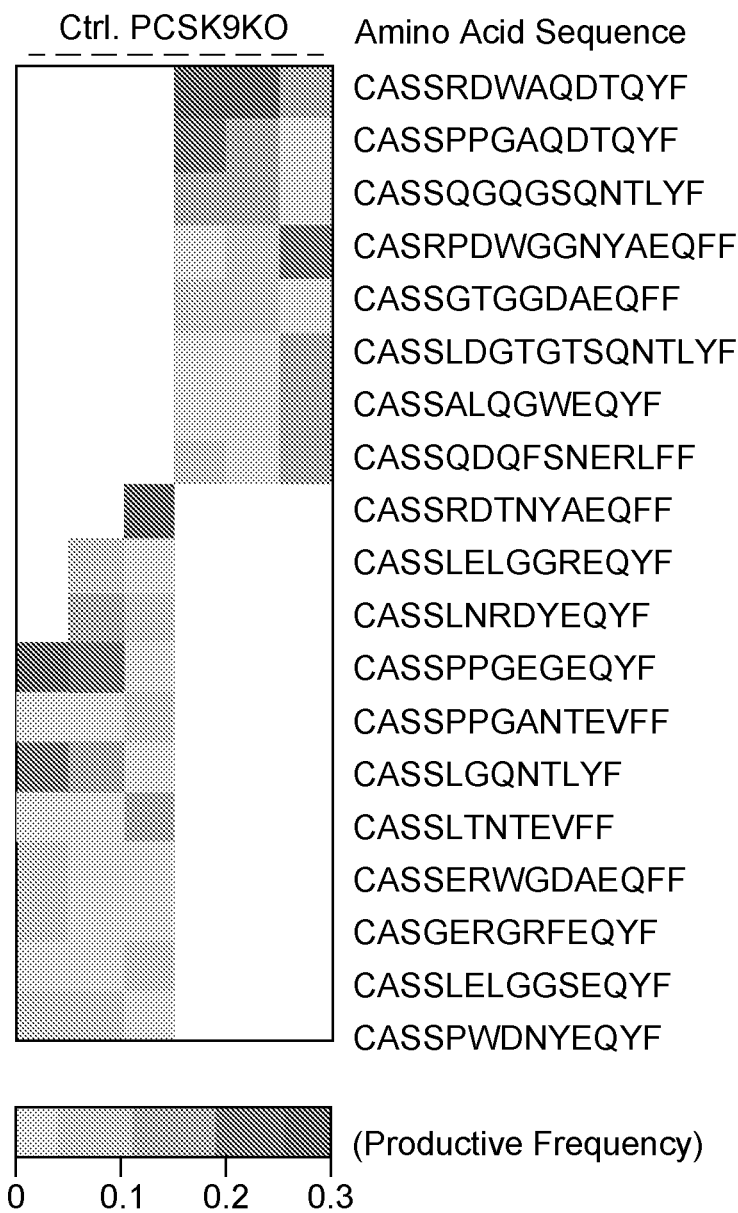

To further characterize the effects of PCSK9 deficiency on the nature of intratumoral T cells, molecular analysis of the T cell receptor (TCR) repertoire was carried out. The analysis suggests that total TCR counts (FIG. 8I) as well as the number of unique TCRs (FIG. 8J) were significantly increased in PCSK9-deficient tumors, suggesting that both the number and the diversity of mature T cells were significantly elevated in PCSK9-deficient tumors. Further analysis showed that productive clonality, which is a measurement of the dominance of individual T cell clones, was significantly elevated in PCSK9-deficient tumors (FIG. 8K), indicating significant expansion and dominance of a subset of T cell clones in addition to the overall increase in the diversity of mature T cells. Close examination indicates that the maximum dominance of individual T cell clones in both control and PCSK9-deficient tumors was close to 0.3 (30%), which suggests some T-cell clones accounted for 30% of all intratumoral T-cell populations (FIG. 8L). The clones that were most dominant in PCSK9-deficient tumors were different from those that were most dominant in control tumors (FIG. 8M).

Figure 8N:
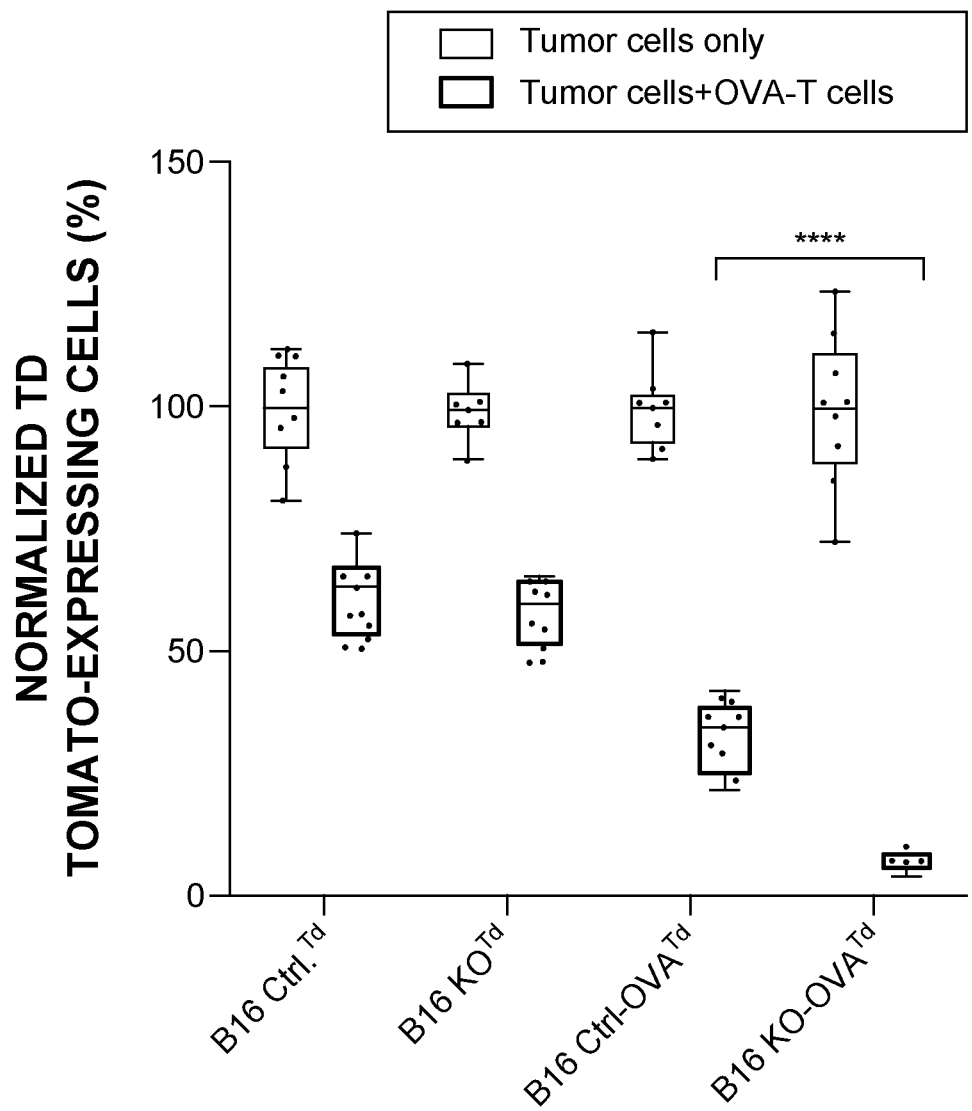
Figure 9A:
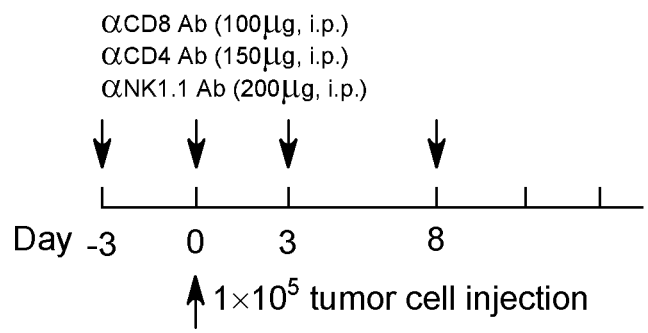
FIGS. 9A-9F are images and graphs showing data on the roles of various immunoeffector cells in mediating growth delay of PCSK9 deficient tumors.
Figure 9B:
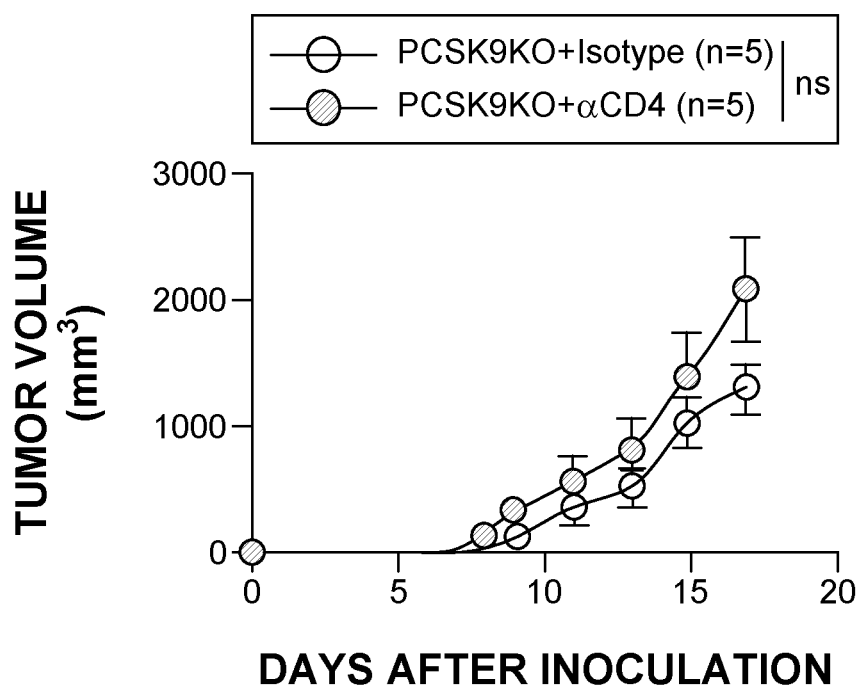
Figure 9C:
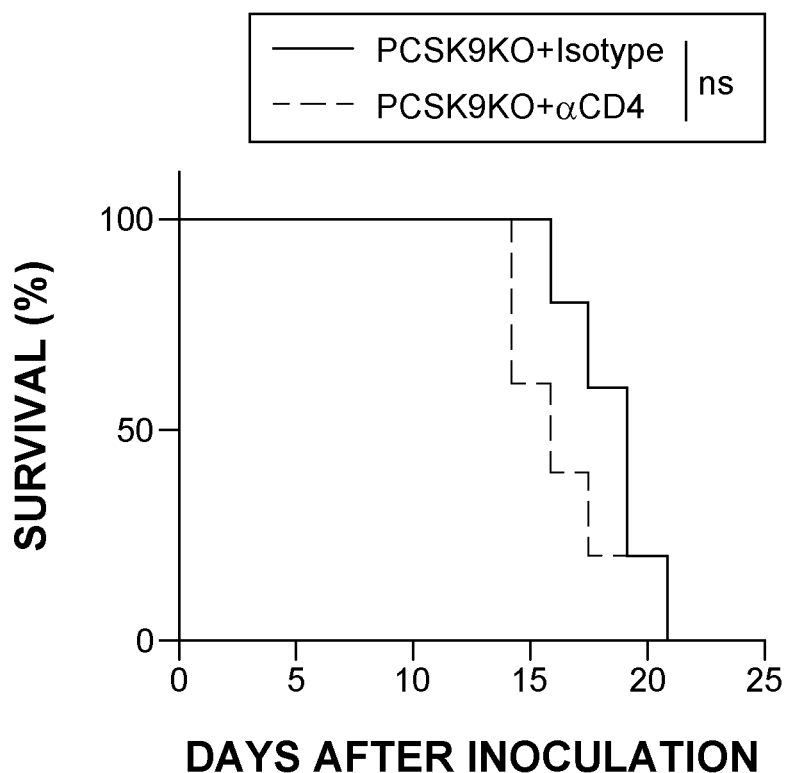
Figure 9D:
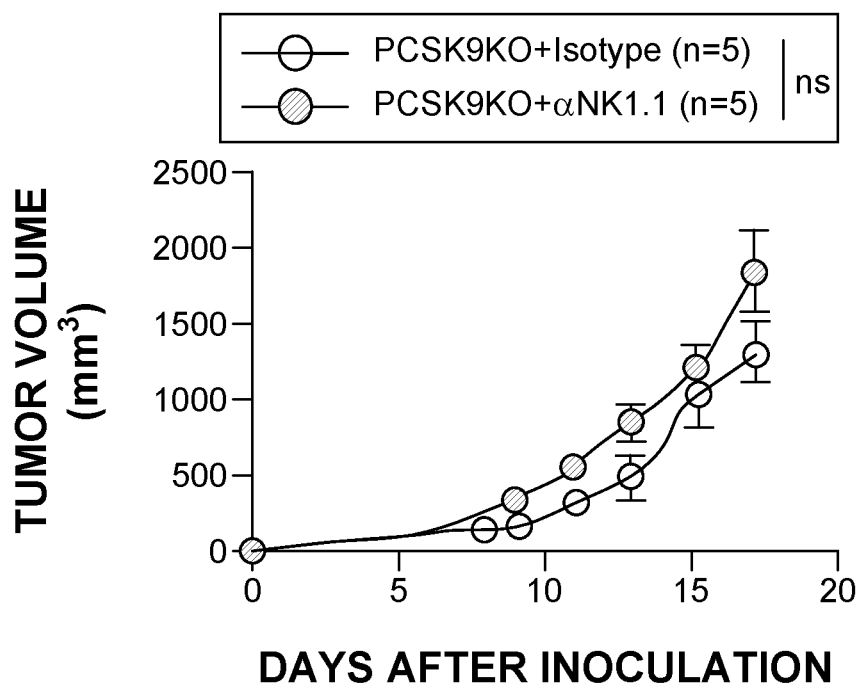
Figure 9E:
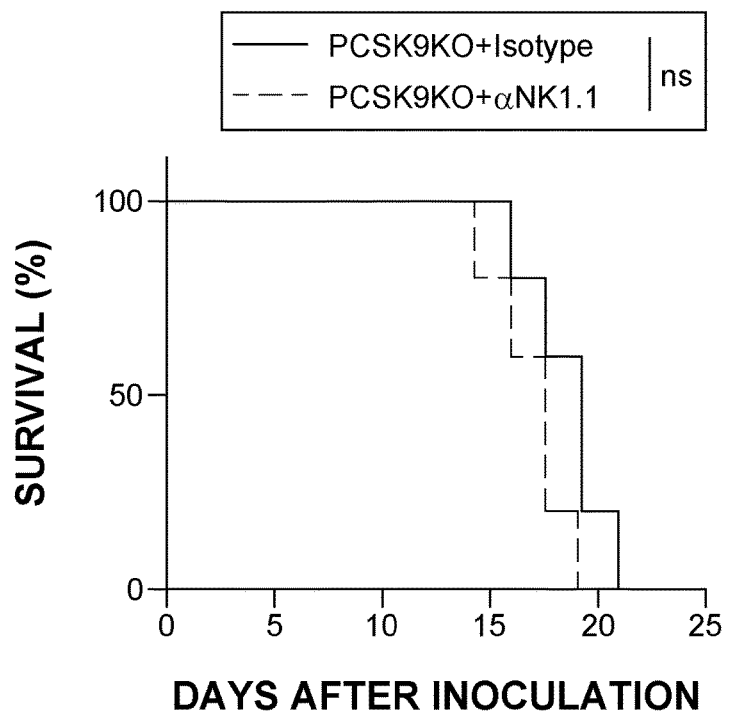
Figure 9F:
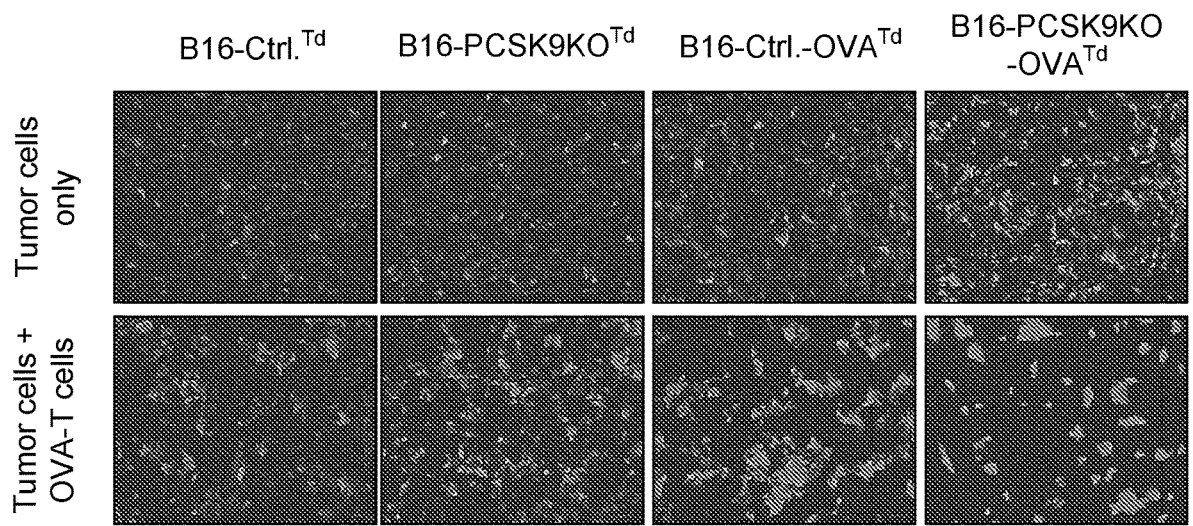

In further experiments, the influence of PCSK9 deficiency on CTL-mediated cell killing of tumor cells was determined. To do this, OT-I transgenic mouse models where T cells engineered to express TCR specific for the chicken OVA antigen (SIINFEKL) were isolated and its cytotoxic effects against OVA-transduced, tdTomato-labeled vector control and PCSK9-deficient B16F10 melanoma cells were evaluated in vitro. The results indicate that PCSK9 deficiency causes B16F10 cells to be significantly more susceptible to the cytotoxic T cell activities (FIGS. 8N and 9F).

The relationship between PCSK9 expression and tumor immune signature in human cancer patients was evaluated by use of a publicly available database (GENT, gene expression across normal and tumor tissue). Findings show that PCSK9 mRNA expression is negatively correlated with expression of CTL marker CD8A in human esophageal carcinoma, colon adenocarcinoma, pancreatic adenocarcinoma, and prostate adenocarcinoma (FIGS. 8O.I and 8O.II), suggesting that the above findings in mice are relevant to outcomes in human patients.

Figure 10A:
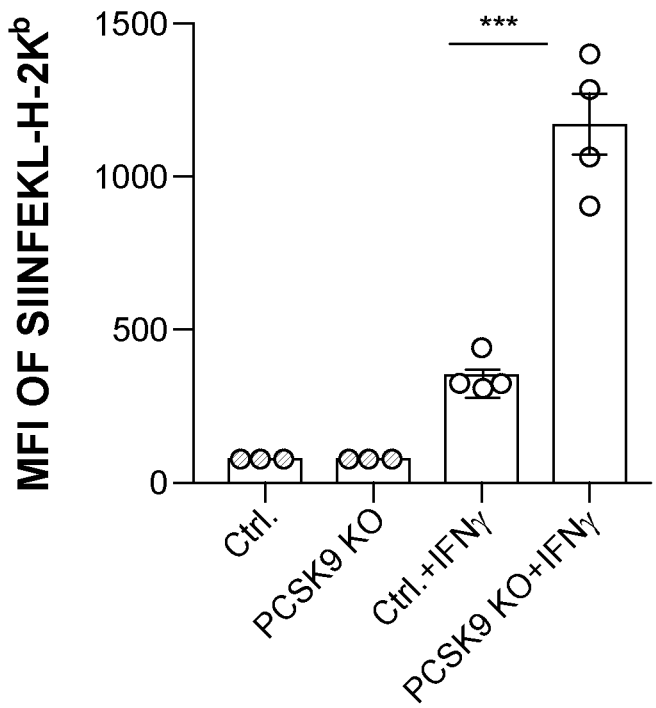
FIGS. 10A-10H are images and graphs showing PCSK9 promotes lysosome-mediated degradation of MHC-I in tumor cells.
Figure 10B:
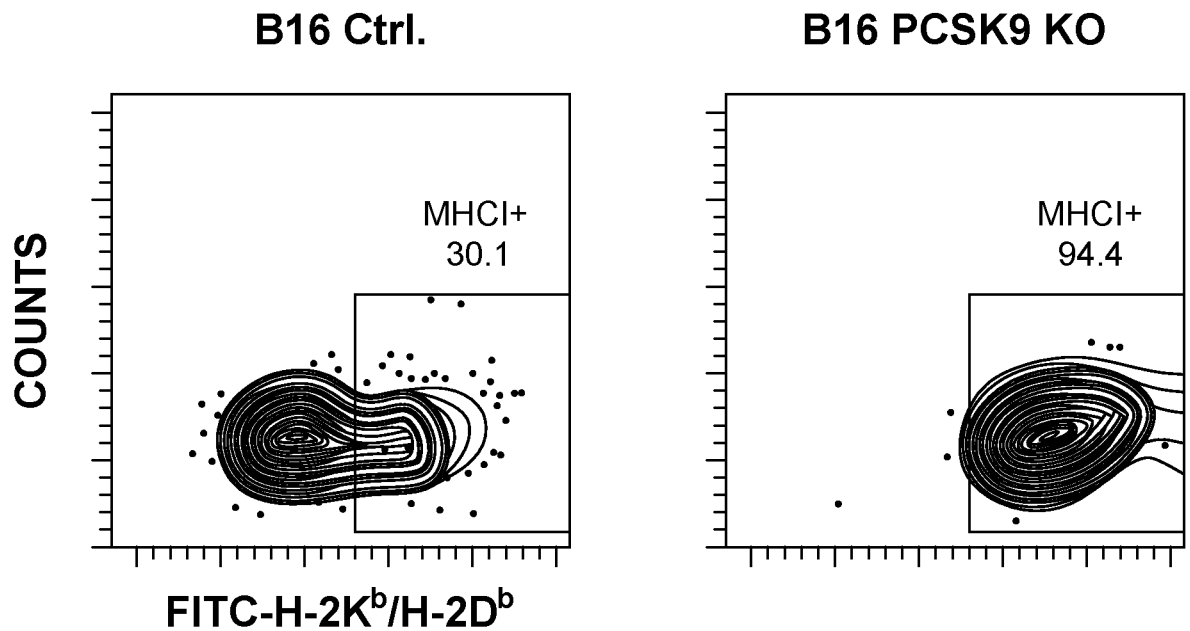
Figure 10C:
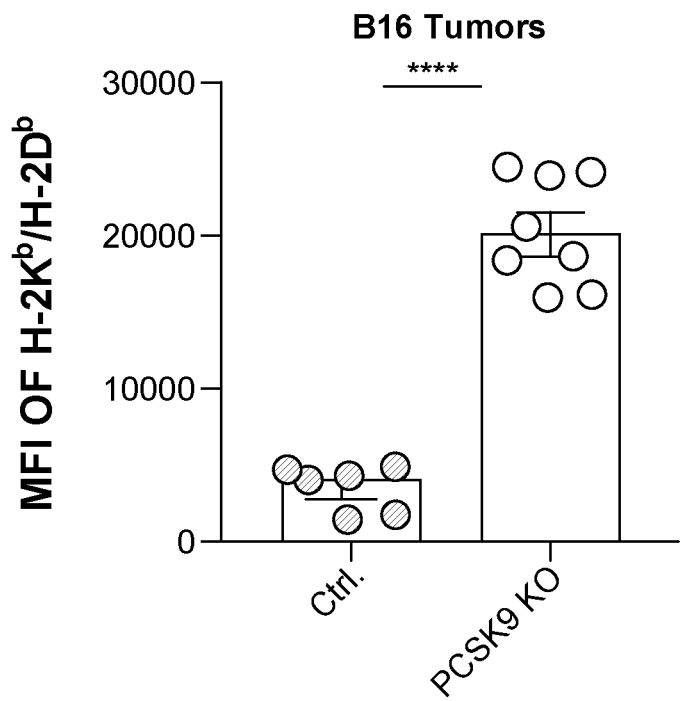
Figure 10D:
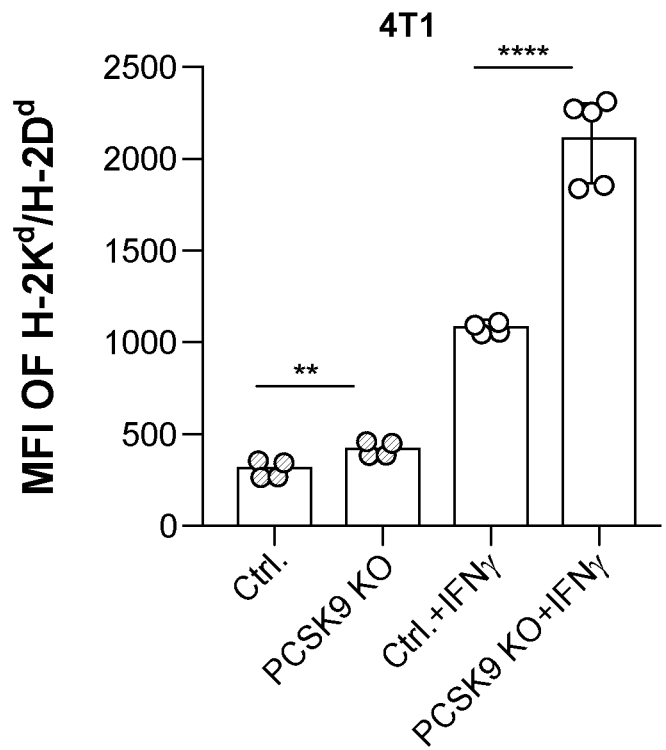
Figure 10E:
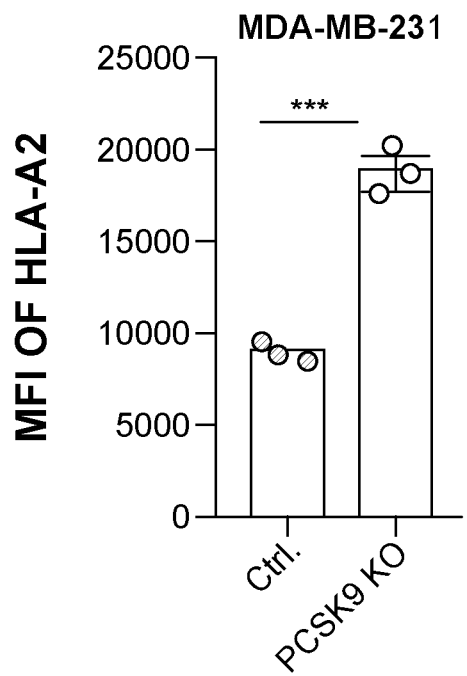
Figure 10F:
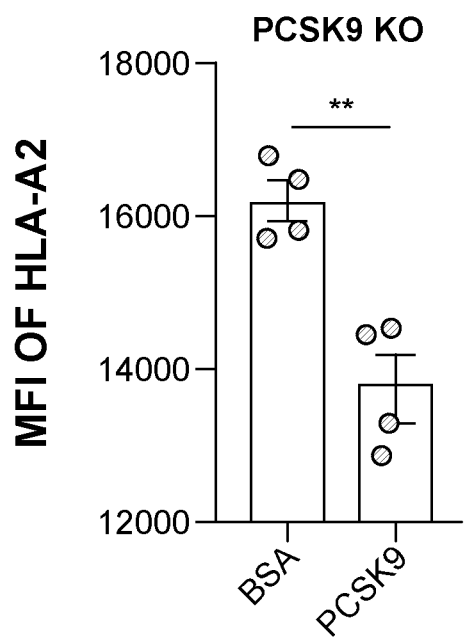
Figure 10G:
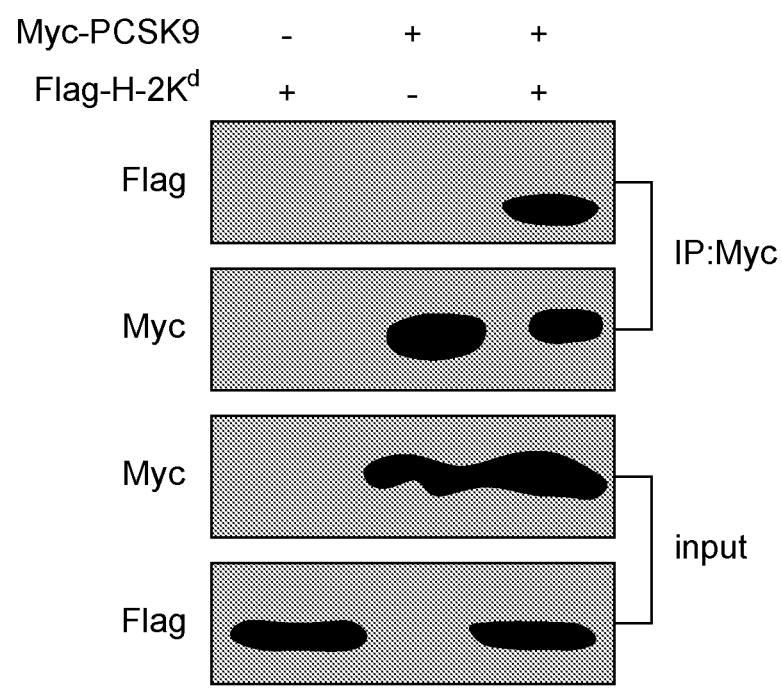
Figure 10H:
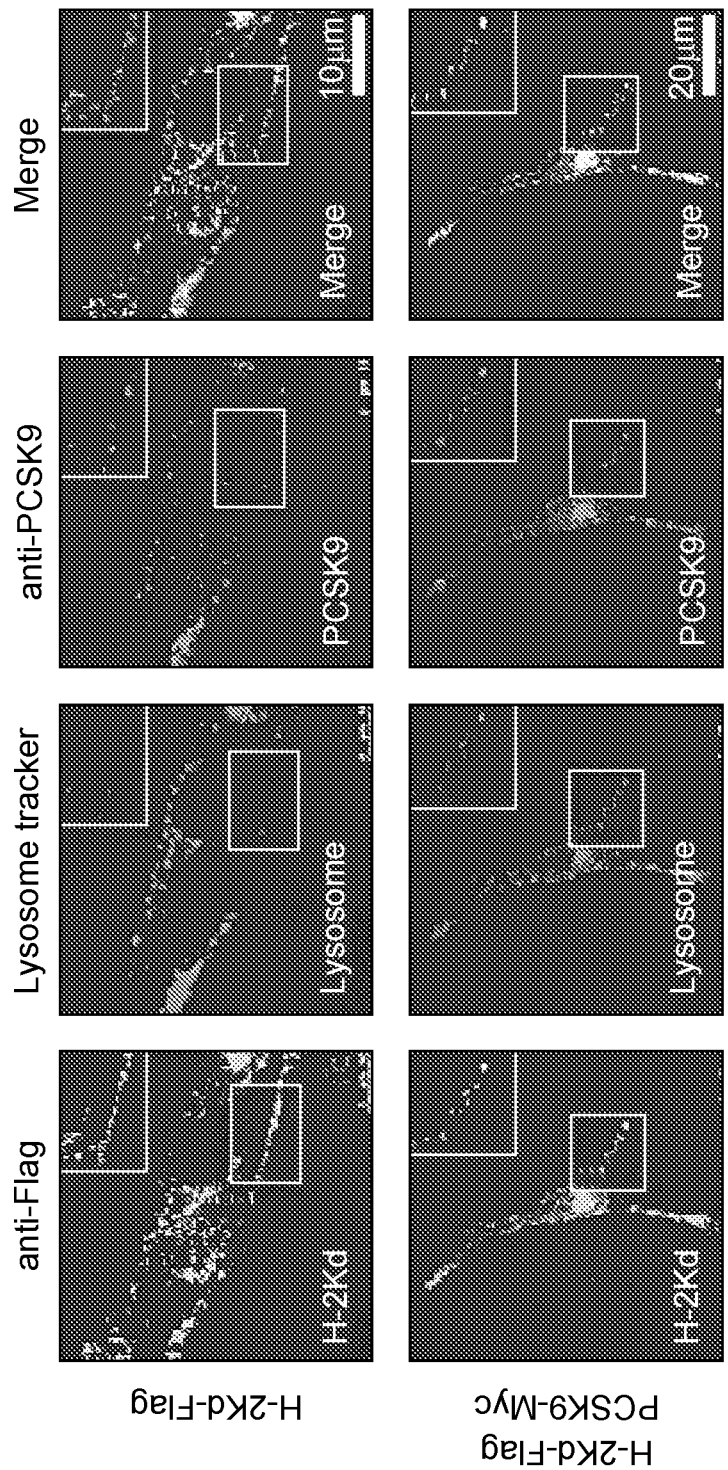
Figure 11A:
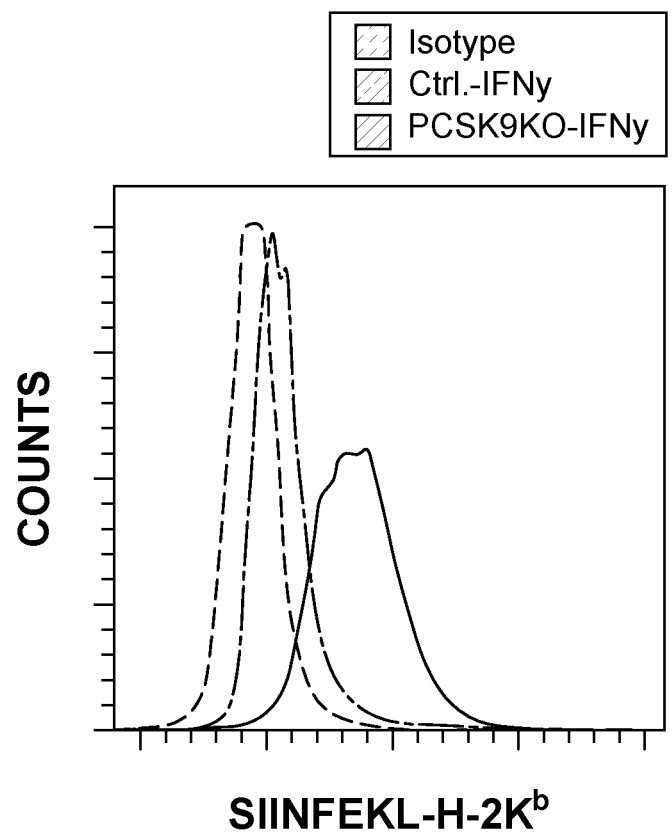
FIGS. 11A-11D are images and graphs showing data on the relationships between PCSK9 and MHC or HLA in mouse or human tumor tissues.

Referring now to FIGS. 10A-10H, the molecular mechanism involved in the enhanced CTL killing of PCSK9-deficient tumor cells was examined. Because of known activities of PCSK9 in regulating cell surface protein levels such as LDL-R, the hypothesis that PCSK9-deficiency may influence antigen presentation on the surface of tumor cells was tested. Since MHC-I is the key antigen presenting protein complex that plays a major role in modulating CTL activities, the influence of PCSK9 deficiency on the ability of the MHC-I complex to present a well-characterized OVA antigen (SIINFEKL) in B16F10 melanoma cells was analyzed. Flow cytometry analysis was conducted by use of a fluorescently labeled antibody against H-2K$^b$/SIINFEKL complex in control and PCSK9-deficient B16F10 cells expressing the chicken ovalbumin (OVA) gene. The results clearly indicate that H-2K$^b$/SIINFEKL staining was significantly enhanced on the surface of PCSK9-deficient B16F10-OVA cells when compared with control B16-F10-OVA cells (FIGS. 10A and 11A). The results demonstrate that PCSK9 has a strong influence on the ability of MHC I presentation of peptide antigens.

Figure 11B:
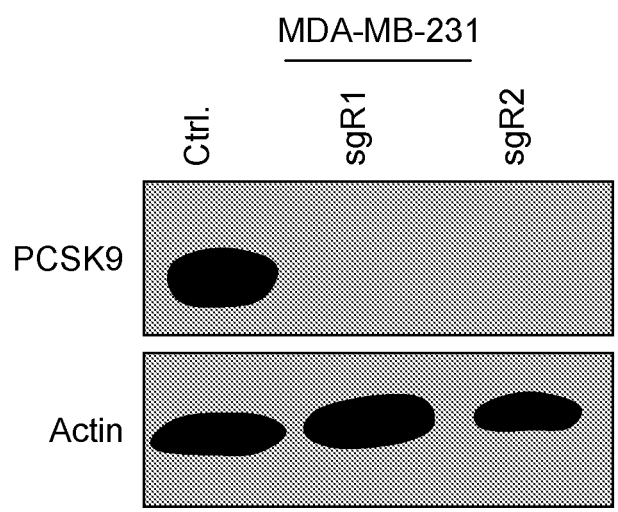

The effect of PCSK9 knockout on H-2K$^b$ levels on the surface of B16F10 tumor cells grown in vivo were examined. Tumors grown from tdTomato-transduced vector control and PCSK9-deficient B16F10 cells were dis-aggregated and analyzed through flow cytometry) for H-2K$^b$ surface expression. The results indicate that MHC-I expression on tdTomato positive cells was significantly increased in PCSK9-deficient versus control B16F10 tumors in vivo (FIGS. 10B, 10C). Similarly, PCSK9 deficiency also caused a significant increase in MHC-I (H-2K$^d$) in IFNγ-treated 4T1 cells in vitro (FIGS. 10D and 11A). Consistently, genetic depletion of PCSK9 (FIG. 11B) caused a significant increase in HLA-2 levels in the human triple negative breast cancer line MDA-MB231 (FIG. 10E). On the other hand, incubation of exogenous PCSK9 protein with PCSK9-deficient MDA-MB231 cells caused a significant decrease in surface HLA-A2 levels (FIG. 10F). The results therefore suggest that PCSK9 negatively regulates cell surface MCH-I expression in both human and mouse tumor cells, a result that provides a plausible explanation for findings of enhanced CTL activities against PCSK9-deficient tumor cells.

Figure 11C:
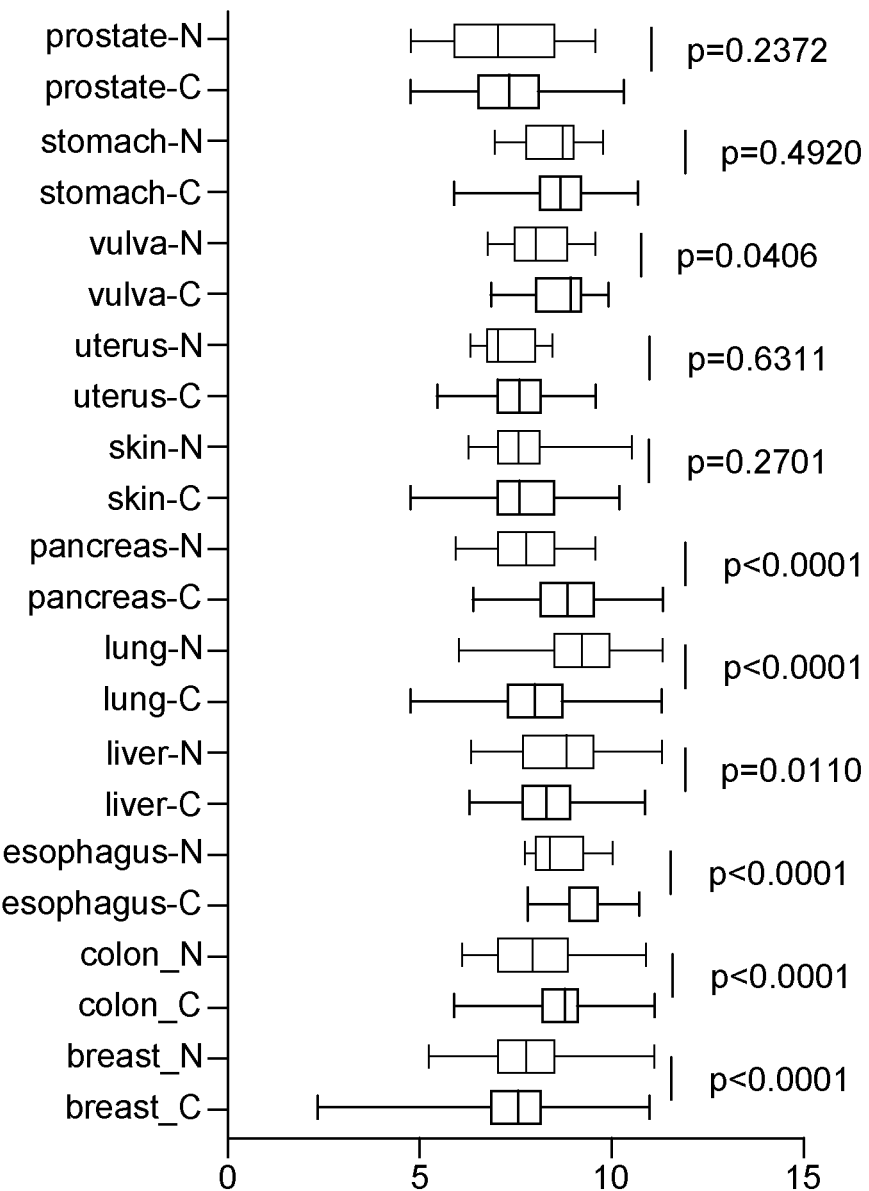
Figure 11D:
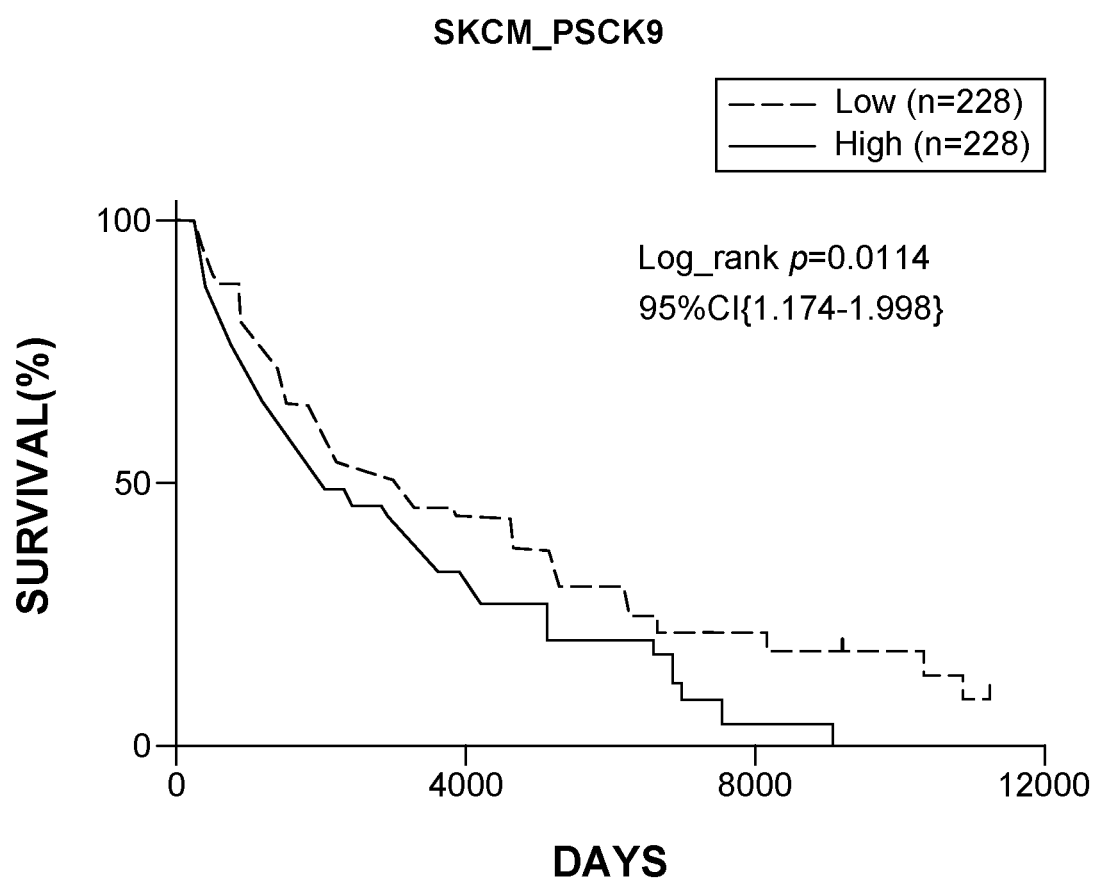

A survey of public domain database (GENT) indicated that in several human cancer types (vulva, pancreas, esophagus, colon, and breast), PCSK9 expression is higher in cancer tissues versus matched normal tissues (FIG. 11C). Furthermore, in human skin cancer higher PCSK9 expression correlated with worse prognosis in patients (FIG. 11D). This data indicates that PCSK9 plays a key role in determining the treatment outcome in human cancer patients.

Figure 12A:
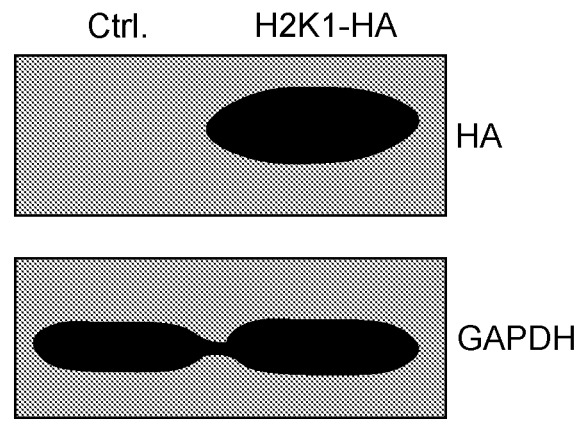
FIG. 12A is an image showing the influence of H2-K1 overexpression on anti-PD1 treatment in B16F10 Tumors.
Figure 12B:
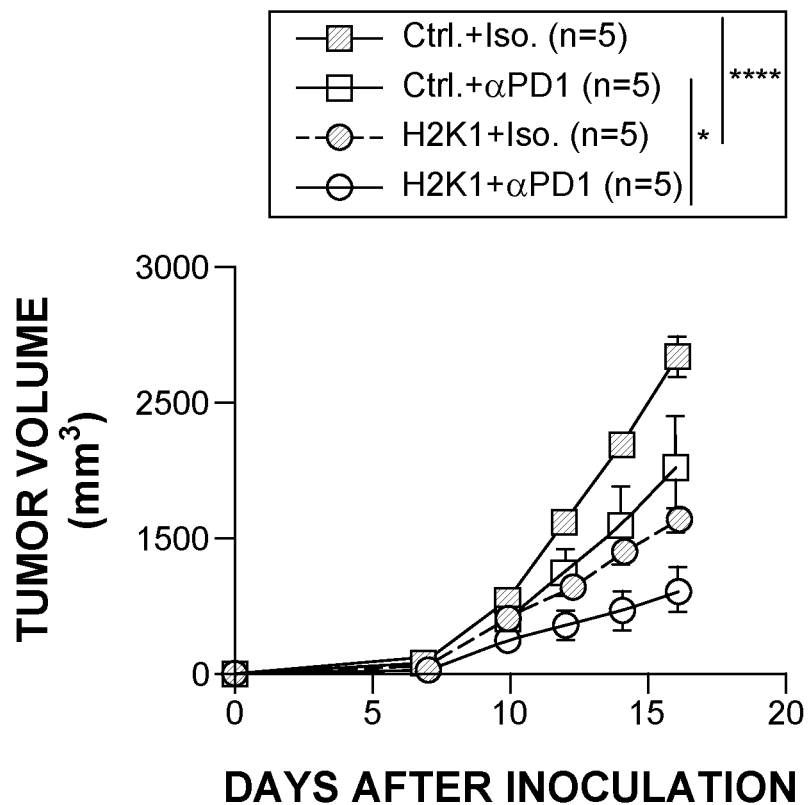
FIG. 12B is a graph showing the influence of H2-K1 overexpression on anti-PD1 treatment in B16F10 tumors.
Figure 12C:
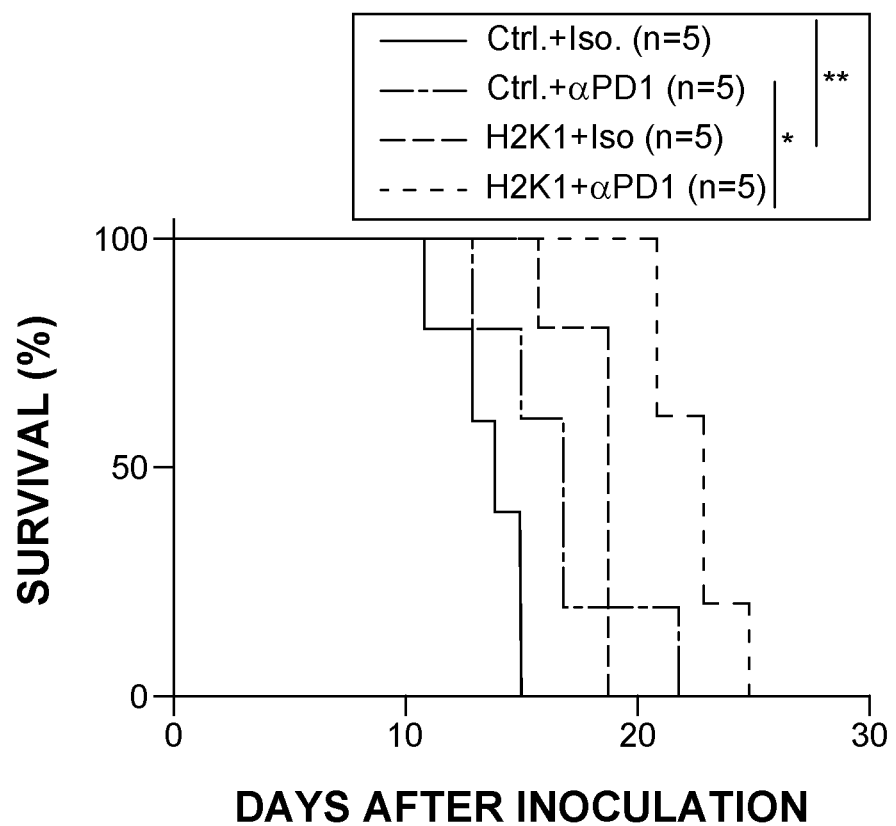
FIG. 12C is a graph showing the influence of H2-K1 overexpression on anti-PD1 treatment in B16F10 tumors.
Figure 13A:
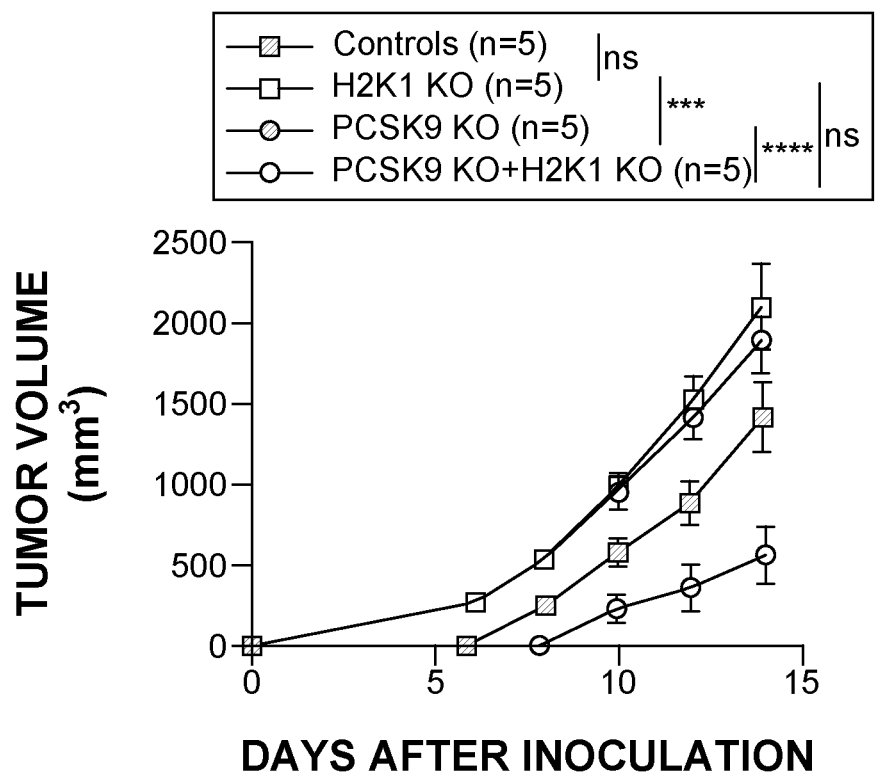
FIG. 13A is a graph showing the examination of epistasis relationship between PCSK9 and H2-K1 proteins and their influences on growth of B16F10 tumors in immunocompetent C57BL/6 mice.
Figure 13B:
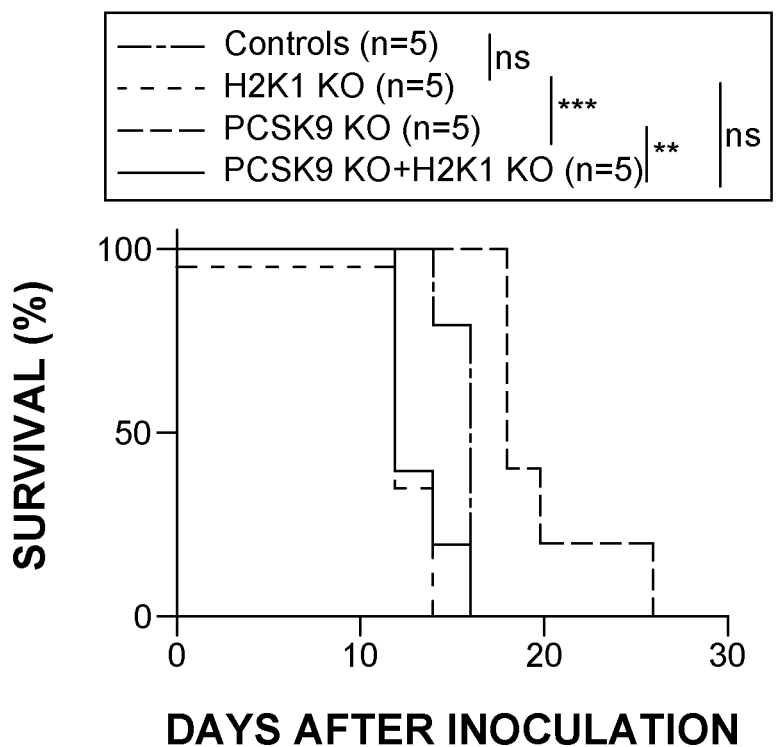
FIG. 13B is a graph showing the examination of epistasis relationship between PCSK9 and H2-K1 proteins and their influences on growth of B16F10 tumors in immunocompetent C57BL/6 mice.
Figure 14A:
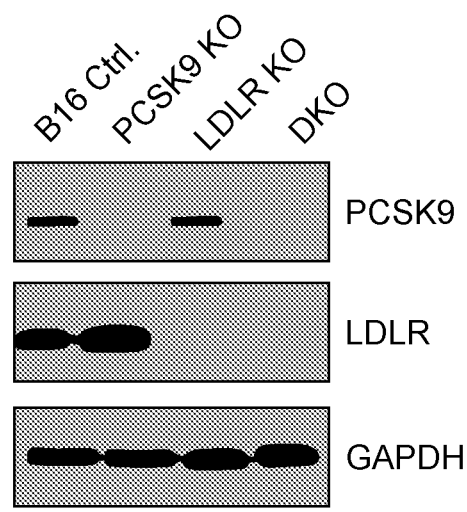
FIG. 14A is an image showing the examination of the relationship between PCSK9 and LDLR in determining cell surface MHC-I expression and tumor forming abilities of B16F10 melanoma cells.
Figure 14B:
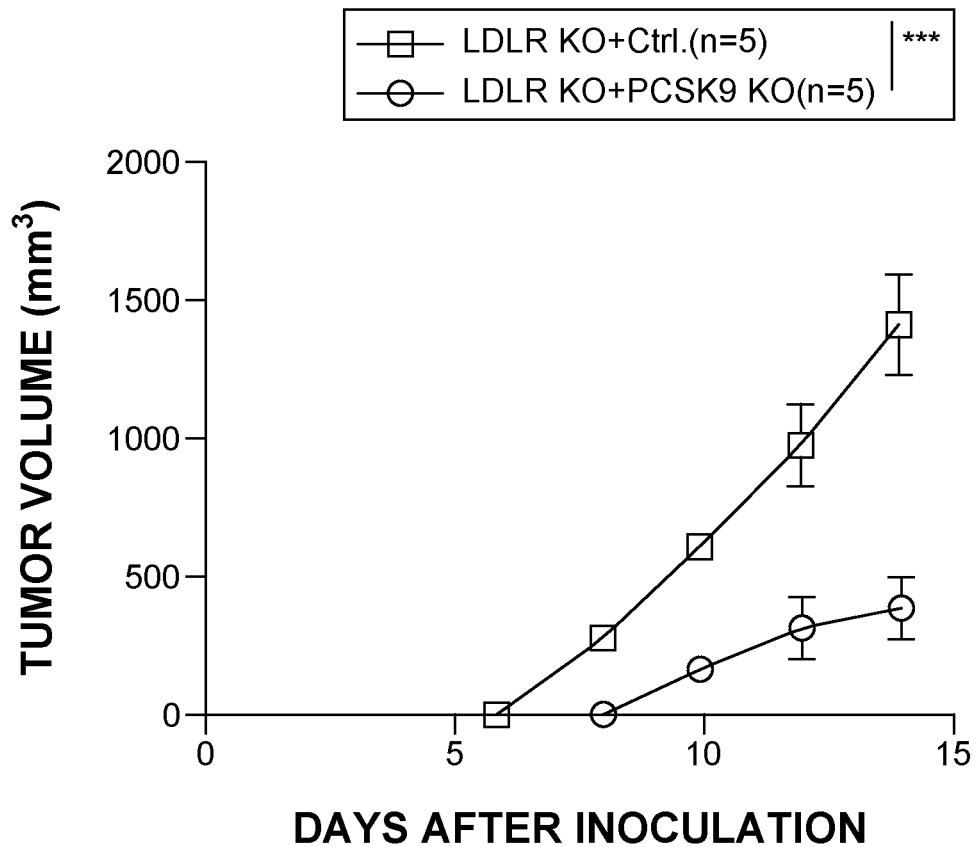
FIG. 14B is a graph showing the examination of the relationship between PCSK9 and LDLR in determining cell surface MHC-I expression and tumor forming abilities of B16F10 melanoma cells.
Figure 14C:
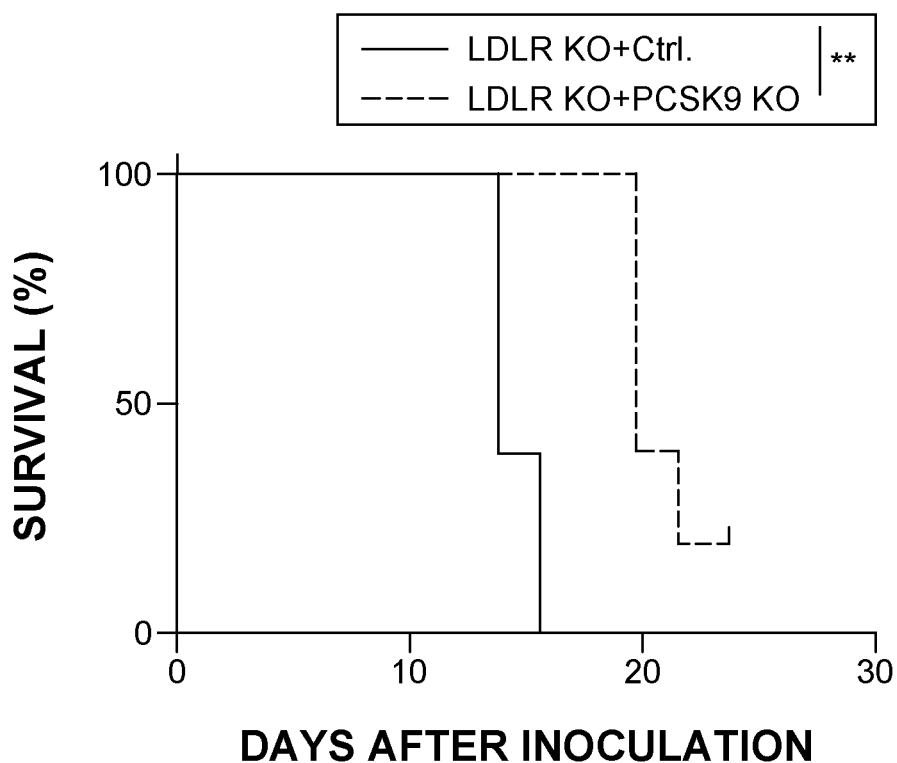
FIG. 14C is a graph showing the examination of the relationship between PCSK9 and LDLR in determining cell surface MHC-I expression and tumor forming abilities of B16F10 melanoma cells.
Figure 14D:
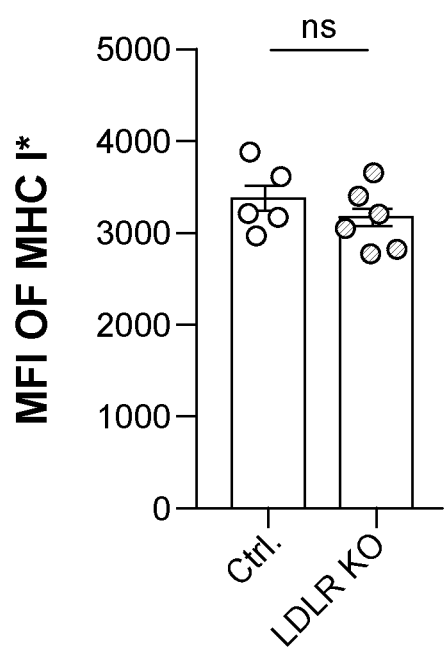
FIG. 14D is a graph showing the examination of the relationship between PCSK9 and LDLR in determining cell surface MHC-I expression and tumor forming abilities of B16F10 melanoma cells.
Figure 14E:
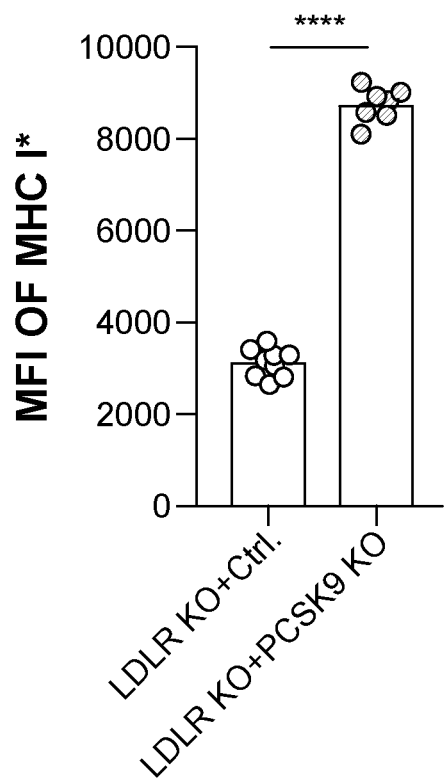
FIG. 14E is a graph showing the examination of the relationship between PCSK9 and LDLR in determining cell surface MHC-I expression and tumor forming abilities of B16F10 melanoma cells.
Figure 14F:
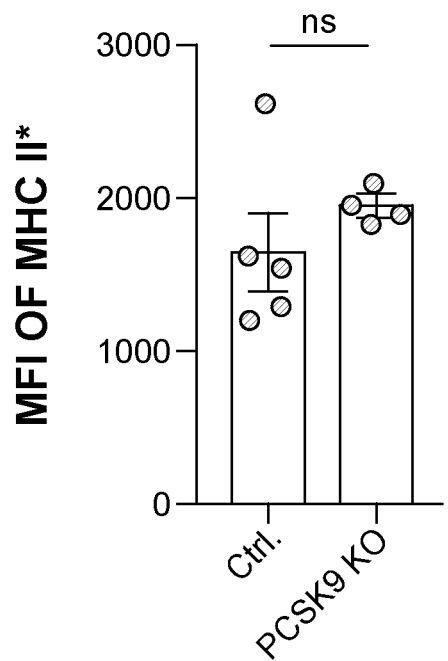
FIG. 14F is a graph showing the examination of the relationship between PCSK9 and LDLR in determining cell surface MHC-I expression and tumor forming abilities of B16F10 melanoma cells.
Figure 14G:
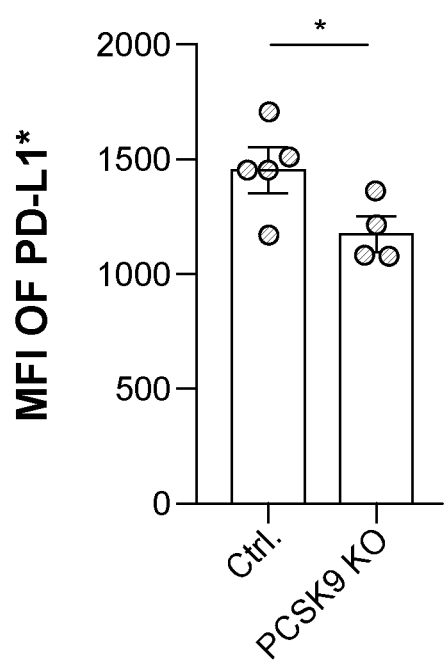
FIG. 14G is a graph showing the examination of the relationship between PCSK9 and LDLR in determining cell surface MHC-I expression and tumor forming abilities of B16F10 melanoma cells.
Figure 15A:
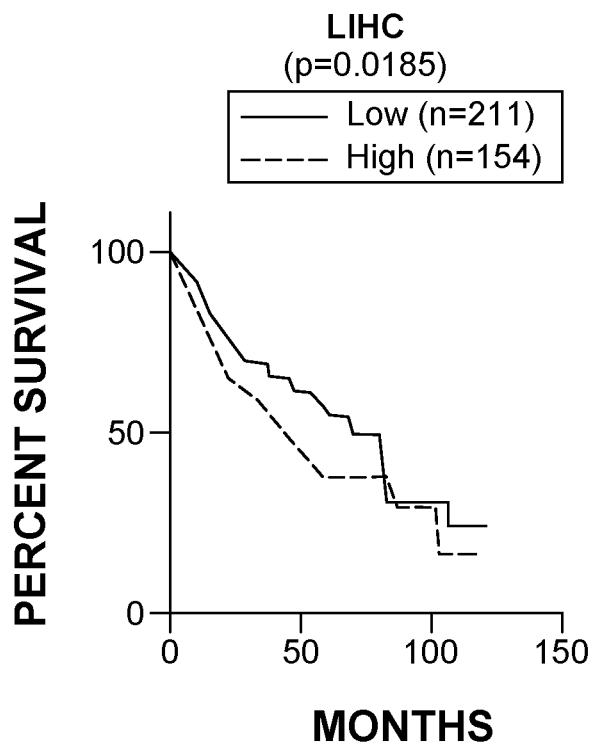
FIG. 15A is a graph showing the correlation between PCSK9 mRNA levels and survival rates in human liver hepatocellular carcinoma (LIHC).
Figure 15B:
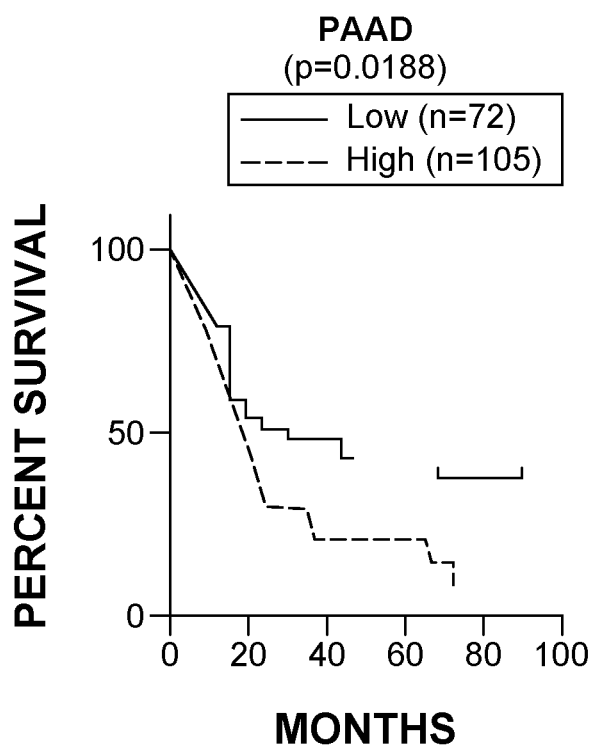
FIG. 15B is a graph showing the correlation between PCSK9 mRNA levels and survival rates in pancreatic adenocarcinoma (PAAD).
Figure 15C:
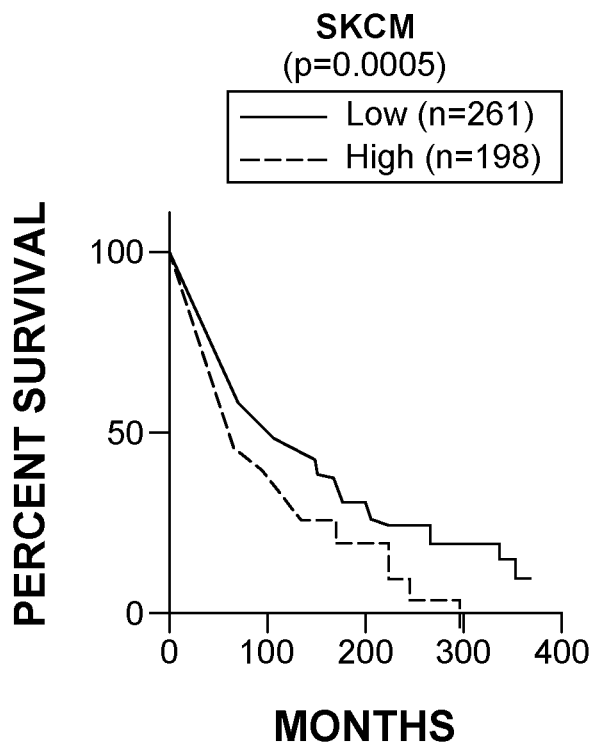
FIG. 15C is a graph showing the correlation between PCSK9 mRNA levels and survival rates in skin cutaneous melanoma (SKCM).
Figure 15D:
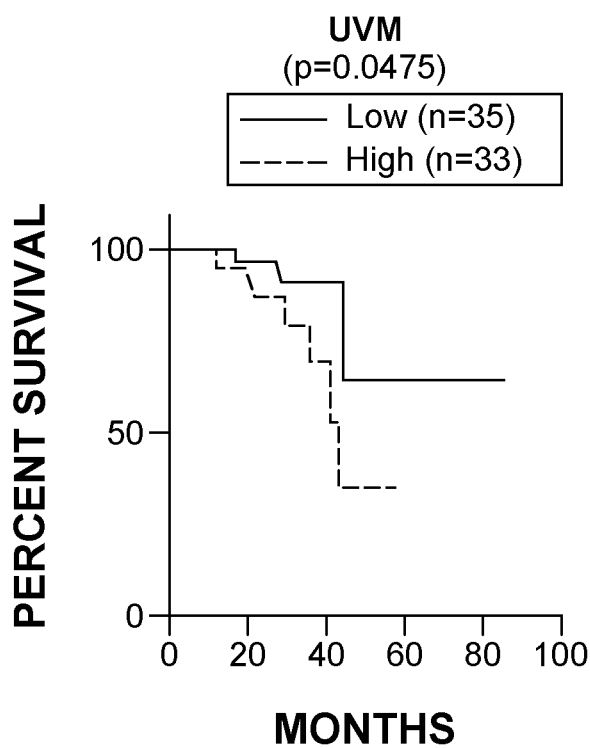
FIG. 15D is a graph showing the correlation between PCSK9 mRNA levels and survival rates in, uveal melanoma (UVM).
Figure 15E:
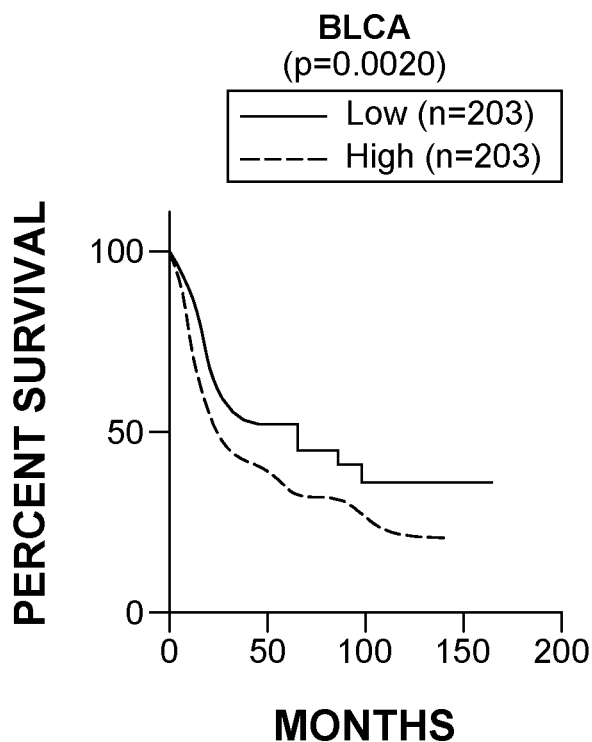
FIG. 15E is a graph showing the correlation between PCSK9 mRNA levels and survival rates in human bladder urothelial carcinoma (BLCA)
Figure 15F:
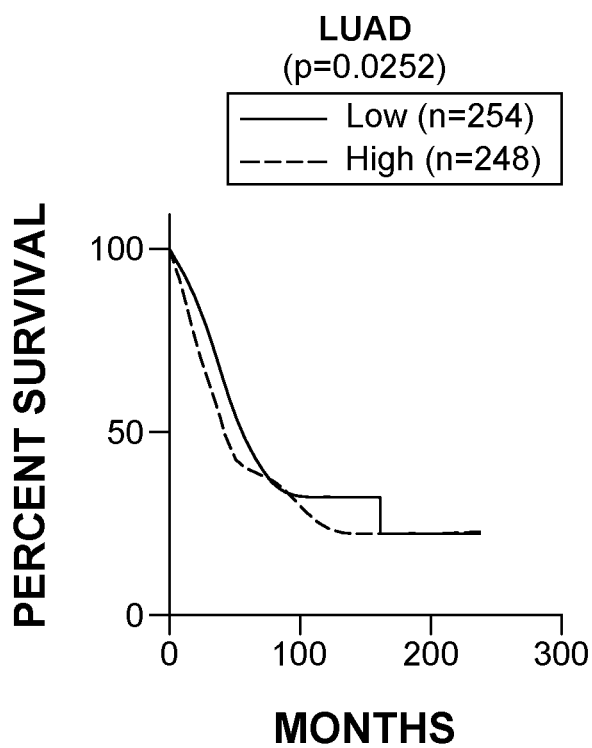
FIG. 15F is a graph showing the correlation between PCSK9 mRNA levels and survival rates in lung adenocarcinoma (LUAD).
Figure 15G:
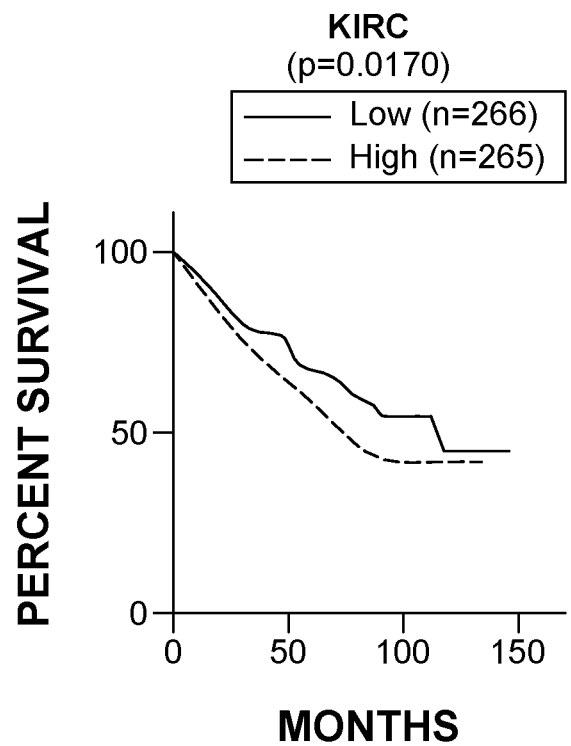
FIG. 15G is a graph showing the correlation between PCSK9 mRNA levels and survival rates in kidney renal clear cell carcinoma (KIRC).
Figure 15H:
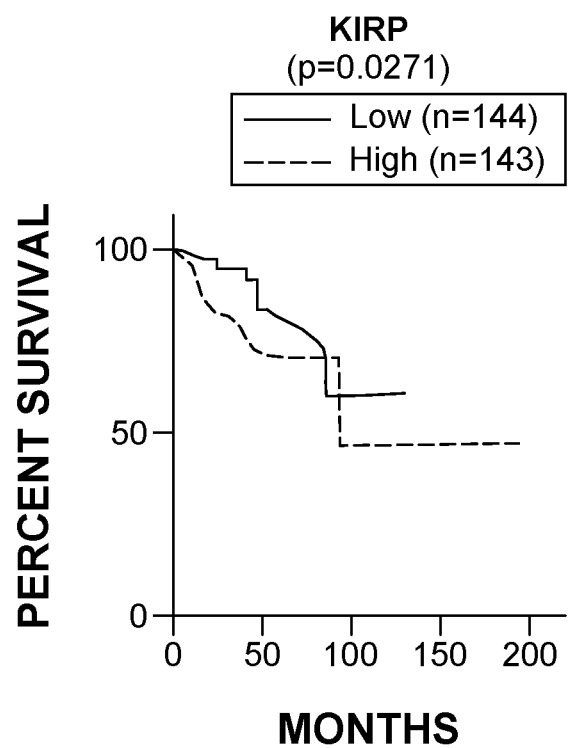
FIG. 15H is a graph showing the correlation between PCSK9 mRNA levels and survival rates in kidney renal papillary cell carcinoma (KIRP)
Figure 15I:
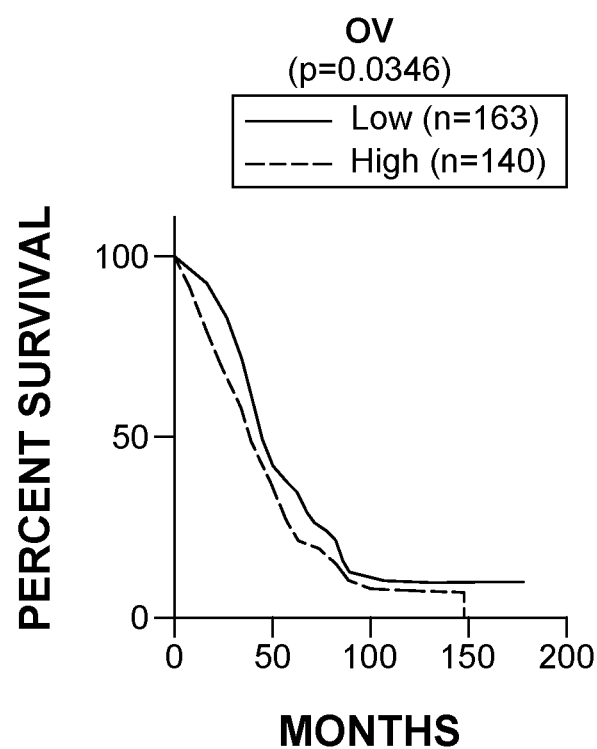
FIG. 15I is a graph showing the correlation between PCSK9 mRNA levels and survival rates in ovarian carcinoma (OV).

Referring now to FIGS. 12A-C and 13A-B, the importance of MHC-I expression levels for immune checkpoint therapy was examined. H2-K1 was over-expressed in the B16F10 melanoma cells and its tumor-forming abilities and response to anti-PD1 therapy was examined. The results indicated that H2-K1 expression could significantly attenuate tumor growth. Furthermore, H2-K1 expression could significantly enhance the efficacy of anti-PD1 therapy of B16F10 tumors (FIGS. 12A-C). After establishing the important role of MHC-I in tumor immunotherapy, whether MHC-I is functionally required in mediating the anti-tumor efficacy of PCSK9 inhibition was examined. H2-K1 KO or H2-K1/PCSK9 double knockout (DKO) B16F10 were generated and their abilities to form tumors in C57BL/6 mice was evaluated. The results indicated that H2-K1 deficiency caused significant increase in tumor growth rates when compared with control. Moreover, it almost completely abolished the tumor-growth delay observed in PCSK9 knockout tumors (FIG. 13A). The results therefore established H2-K1 as an essential downstream factor of PCSK9 in regulating tumor growth.

Referring now to FIGS. 14A-G, the mechanism through which PCSK9 exerts control over cell surface PCSK9 expression was examined. Previously it was reported that cholesterol levels may influence MHC-I recycling, and therefore the possibility that PCSK9 could regulate MHC-I indirectly through LDLR, the key cholesterol regulator that is also an established downstream target of PCSK9, was hypothesized. In order to determine if LDLR levels could regulate MHC-I levels downstream of PCSK9, B16F10 cells with LDLR knockout or LDLR/PCSK9 double knockout were generated. Subsequently, the tumor formation rate from the two cell lines were compared, and the data indicated that LDLR knockout did not diminish the growth suppression caused by PCSK9 deficiency in B16F10 tumors. MHC-I levels of the tumor cells in vivo were then determined by use of flow cytometry. The data indicated that LDLR knockout in B16F10 did not have significant influence on MHC-I expression on the surface of B16F10 cells in vivo. Furthermore, LDLR knockout did not diminish PCSK9 deficiency induced up-regulation of MHC-I surface expression. Whether the MHC-I boosting effect of PCSK9 inhibition was limited to MHC-I was then determined by examining tumor cell surface expression levels of MHC II and PD-L1. The data showed that PCSK9 status had not effect on MHC-II expression and only a very small (but significant) effect in lowering PD-L1 surface expression. In combination with earlier data demonstrating H2-K1 knockout abrogating the effect of PCSK9, the findings support MHC-I being the major downstream target of PCSK9 in regulating tumor growth.

The molecular mechanism of PCSK9-inhibition mediated upregulation of MHC-I cell surface expression was examined. Because of PCSK9's known ability to down-regulate the LDL-R protein through physical interaction and endocytosis into the lysosome for the degradation of the latter, whether PCSK9 could associate with MHC-I directly was examined. Results show that co-expressed PCSK9 and H2-K$^d$ could form a complex in B16F10 cells, as evidenced by the presence of H2-K$^d$ in the anti-PCSK9 immunoprecipitate (FIG. 10G). To further examine the relationship between the two proteins, immunofluorescence co-staining of H-2K$^d$ and PCSK9 were carried out in B16F10 cells. In the absence of PCSK9 co-expression, many H2-K$^d$ proteins were found to locate outside of the lysosome (FIG. 10H). However, in the presence of PCSK9 co-expression, H2-K$^d$ and PCSK9 co-localize to a high degree (FIG. 10H). More importantly, there was widespread colocalization of the proteins to the lysosome (FIG. 10H). The results therefore suggest that PCSK9 down-regulate MHC-I surface levels in a manner similar to its negative regulation of LDL-R.

Referring now to FIG. 15A-I, PCSK9-associated survival analysis for nine TCGA human cancer patient cohorts, including human liver hepatocellular carcinoma (LIHC), pancreatic adenocarcinoma (PAAD), skin cutaneous melanoma (SKCM), uveal melanoma (UVM), human bladder urothelial carcinoma (BLCA), lung adenocarcinoma (LUAD), kidney renal clear cell carcinoma (KIRC), kidney renal papillary cell carcinoma (KIRP), and ovarian carcinoma (OV) was carried out. Results showed that the patients with high PCSK9 mRNA expression had worse survival rates than those with low PCSK9 expression, consistent with findings of PCSK9's ability to restrain MHC-I surface expression in mice.

Figure 16:
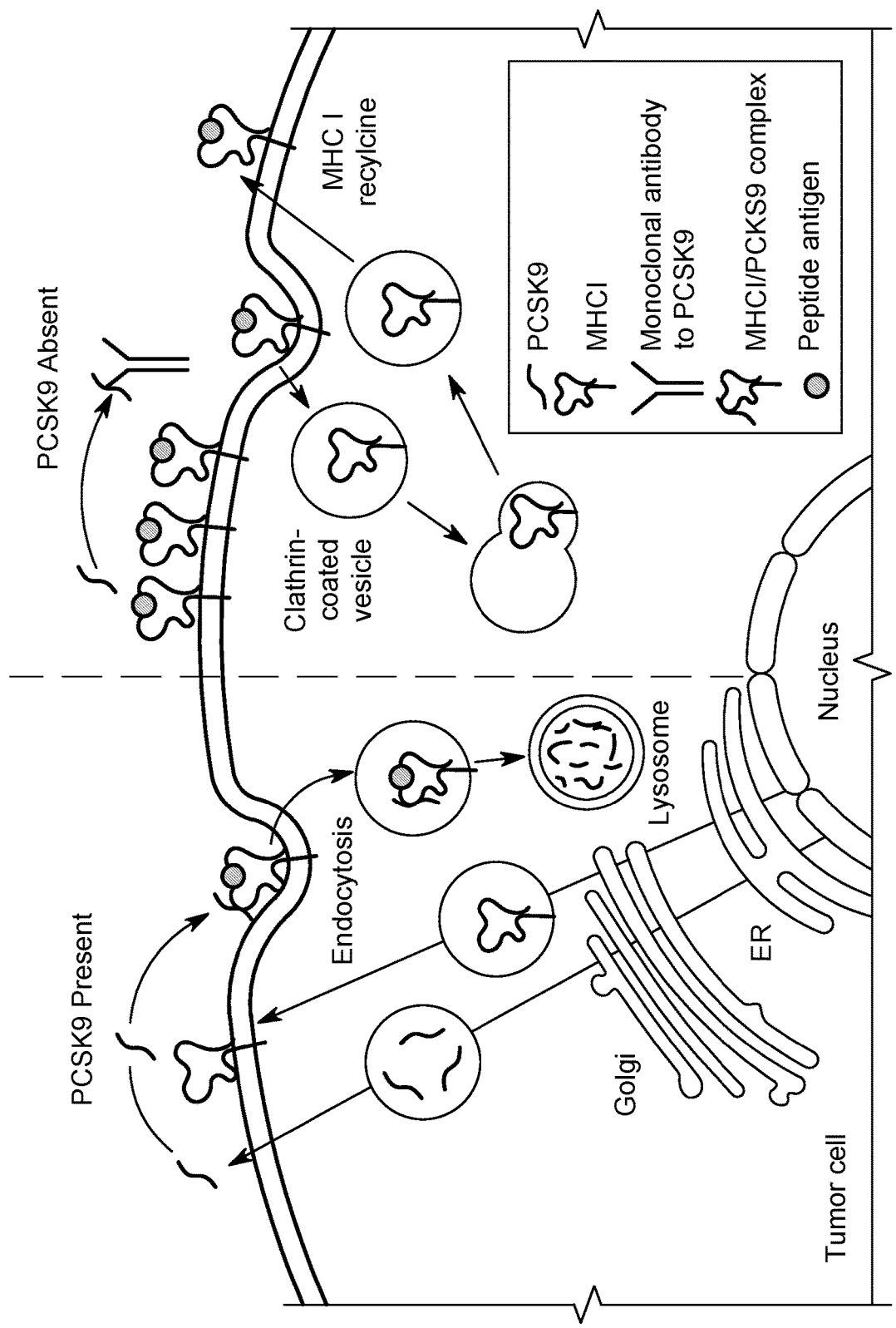
FIG. 16 is a schematic diagram illustrating PCSK9-mediated degradation of MHC-I in the lysosome.

Referring now to FIG. 16, in the presence of PCSK9, MHC-I is transported into the lysosome and degraded (left panel). In the absence of PCSK9, either because of antibody mediated neutralization or genetic deletion, MHC-I levels on the surface remains high and is thus able to present tumor-specific peptic antigens more efficiently to T cells (right panel).

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or any combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The teachings of the disclosure provided herein can be applied to other systems, not necessarily the system described above. The elements and acts of the various embodiments described above can be combined to provide further embodiments.

These and other changes can be made to the disclosure in light of the above Detailed Description. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features, or aspects of the disclosure with which that terminology is associated. In general, the terms used in the following claims should not be construed to limit the disclosure to the specific embodiments disclosed in the specification, unless the above Detailed Description section explicitly defines such terms. Accordingly, the actual scope of the disclosure encompasses not only the disclosed embodiments, but also all equivalent ways of practicing or implementing the disclosure under the claims.

The terms used in this specification generally have their ordinary meanings in the art, within the context of the disclosure, and in the specific context where each term is used. Certain terms that are used to describe the disclosure are discussed above, or elsewhere in the specification, to provide additional guidance to the practitioner regarding the description of the disclosure. For convenience, certain terms may be highlighted, for example using capitalization, italics and/or quotation marks. The use of highlighting has no influence on the scope and meaning of a term; the scope and meaning of a term is the same, in the same context, whether or not it is highlighted. It will be appreciated that same element can be described in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions will control.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example reference to "an additive" can include a plurality of such additives, and so forth.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments +/−20%, in some embodiments, +/−10%, in some embodiments +/−5%, in some embodiments +/−1%, in some embodiments +/−0.5%, and in some embodiments, +/−0.1%, from the specified amount, as such variations are appropriate in the disclosed products and methods.

What is claimed is:

1. A method for treating cancer in an individual comprising:
    administering to the individual a therapeutically effective amount of a PCSK9 inhibitor, wherein the PCSK9 inhibitor comprises an antagonistic antibody against PCSK9; and administering to the individual at least one immune checkpoint inhibitor.

2. The method of claim 1, wherein the PCSK9 inhibitor is administered prior to the administration of at least one immune checkpoint inhibitor.

3. The method of claim 1, wherein the PCSK9 inhibitor is administered after the administration of at least one immune checkpoint inhibitor.

4. The method of claim 1, wherein the PCSK9 inhibitor is administered concurrently with the at least one immune checkpoint inhibitor.

5. The method of claim 1, wherein the at least one immune checkpoint inhibitor is selected from the group consisting of anti-PD1 antibodies, anti-PDL1 antibodies, anti-CTLA4 antibodies, anti-LAG3 antibodies, anti-TIM3 antibodies, anti-TIGIT antibodies, and combinations thereof.

6. The method of claim 1, wherein the at least one immune checkpoint inhibitor comprises an anti-PDA-1 antibody.

7. A method for treating cancer in an individual comprising:
    administering to the individual a therapeutically effective amount of a PCSK9 inhibitor, wherein the PCSK9 inhibitor comprises an antagonistic antibody against PCSK9 and the antagonistic antibody is Repatha (also known as Amgen 145 and evolocumab); and
    administering to the individual at least one immune checkpoint inhibitor.

8. The method of claim 1, wherein the antagonistic antibody is Praluent (also known as REGN 727 [Regeneron] and SAR236553 [Sanofi]).

9. The method of claim 1, wherein the antagonistic antibody is LY3015014 (also known as Frovocimab [Lilly]).

10. The method of claim 1, wherein the antagonistic antibody is RN316 (also known as bococizumab [Pfizer]).

11. The method of claim 1, wherein the antagonistic antibody is 1D05-IgG2 [Merck].

12. The method of claim 1, wherein the antagonistic antibody is 1B20 [Merck].

13. The method of claim 1, wherein the antagonistic antibody is RG7652 [Roche/Genentech].

14. The method of claim 1, wherein the antagonistic antibody is LGT209 [Novartis].

15. The method of claim 1, wherein the antagonistic antibody is MEDI-4166 [Astrazeneca].

16. The method of claim 1, wherein the cancer comprises breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, uterine cervical cancer, endometrial carcinoma, salivary gland carcinoma, mesothelioma, kidney cancer, vulval cancer, pancreatic cancer, thyroid cancer, hepatic carcinoma, skin cancer, melanoma, brain cancer, neuroblastoma, myeloma, head cancer, neck cancer, acute lymphoblastic leukemia, acute myeloid leukemia, Ewing sarcoma, or peripheral neuroepithelioma, and combinations thereof.

17. The method of claim 16, wherein the cancer comprises colon cancer.

18. The method of claim 7, wherein the at least one immune checkpoint inhibitor comprises an anti-PD1 antibody.

19. The method of claim 18, wherein the cancer comprises colon cancer.

20. The method of claim 8, wherein the at least one immune checkpoint inhibitor comprises an anti-PD1 antibody.

21. The method of claim 20, wherein the cancer comprises colon cancer.

* * * * *

SEQUENCE LISTING

```
<160> NUMBER OF SEQ ID NOS: 12

<210> SEQ ID NO 1
<211> LENGTH: 20
<212> TYPE: RNA
<213> ORGANISM: Artificial Sequence
<220> FEATURE:
<223> OTHER INFORMATION: Synthesized

<400> SEQUENCE: 1
acucugugac augaagcaug                                                      20

<210> SEQ ID NO 2
<211> LENGTH: 20
<212> TYPE: RNA
<213> ORGANISM: Artificial Sequence
<220> FEATURE:
<223> OTHER INFORMATION: Synthesized

<400> SEQUENCE: 2
ccccagacag cgucaaauga                                                      20

<210> SEQ ID NO 3
<211> LENGTH: 20
<212> TYPE: RNA
<213> ORGANISM: Artificial Sequence
<220> FEATURE:
<223> OTHER INFORMATION: Synthesized

<400> SEQUENCE: 3
cccgguaaga cccccaucug                                                      20

<210> SEQ ID NO 4
<211> LENGTH: 20
<212> TYPE: RNA
<213> ORGANISM: Artificial Sequence
<220> FEATURE:
<223> OTHER INFORMATION: Synthesized
```

<400> SEQUENCE: 4
ccggggauac cucaccaaga                                              20

<210> SEQ ID NO 5
<211> LENGTH: 58
<212> TYPE: DNA
<213> ORGANISM: Artificial Sequence
<220> FEATURE:
<223> OTHER INFORMATION: Synthesized

<400> SEQUENCE: 5
cctccataga agacaccgac tctagaggat ccgccaccat gggcacccac tgctctgc    58

<210> SEQ ID NO 6
<211> LENGTH: 79
<212> TYPE: DNA
<213> ORGANISM: Artificial Sequence
<220> FEATURE:
<223> OTHER INFORMATION: Synthesized

<400> SEQUENCE: 6
ttgtaatcca gaggttgatt gtcgactcac agatcctctt cagagatgag tttctgttcc    60
tgaacccagg aggcctttg                                                79

<210> SEQ ID NO 7
<211> LENGTH: 61
<212> TYPE: DNA
<213> ORGANISM: Artificial Sequence
<220> FEATURE:
<223> OTHER INFORMATION: Synthesized

<400> SEQUENCE: 7
cctccataga agacaccgac tctagaggat ccgccaccat gtggacggcg gcggacatgg    60
c                                                                   61

<210> SEQ ID NO 8
<211> LENGTH: 73
<212> TYPE: DNA
<213> ORGANISM: Artificial Sequence
<220> FEATURE:
<223> OTHER INFORMATION: Synthesized

<400> SEQUENCE: 8
ttgtaatcca gaggttgatt gtcgactcac ttgtcatcgt cgtccttgta gtccacttta    60
caatctggga gag                                                      73

<210> SEQ ID NO 9
<211> LENGTH: 20
<212> TYPE: DNA
<213> ORGANISM: Artificial Sequence
<220> FEATURE:
<223> OTHER INFORMATION: Synthesized

<400> SEQUENCE: 9
ccactctcga ccctacatgg                                              20

<210> SEQ ID NO 10
<211> LENGTH: 22
<212> TYPE: DNA
<213> ORGANISM: Artificial Sequence
<220> FEATURE:
<223> OTHER INFORMATION: Synthesized

```
<400> SEQUENCE: 10
ggcccccaaa gtgacattta tt                                        22

<210> SEQ ID NO 11
<211> LENGTH: 21
<212> TYPE: DNA
<213> ORGANISM: Artificial Sequence
<220> FEATURE:
<223> OTHER INFORMATION: Synthesized

<400> SEQUENCE: 11
atgaacgcta cacactgcat c                                         21

<210> SEQ ID NO 12
<211> LENGTH: 21
<212> TYPE: DNA
<213> ORGANISM: Artificial Sequence
<220> FEATURE:
<223> OTHER INFORMATION: Synthesized

<400> SEQUENCE: 12
ccatcctttt gccagttcct c                                         21
```